United States Patent [19]
Miller

[11] Patent Number: 5,451,670
[45] Date of Patent: Sep. 19, 1995

[54] RESTRICTION FRAGMENT LENGTH POLYMORPHISM TEST FOR HAPLOTYPING DOMESTICATED FOWL

[75] Inventor: Marcia M. Miller, Altadena, Calif.

[73] Assignee: City of Hope, Duarte, Calif.

[21] Appl. No.: 865,662

[22] Filed: Apr. 7, 1992

Related U.S. Application Data

[63] Continuation of Ser. No. 688,326, Apr. 22, 1991, abandoned, and a continuation-in-part of Ser. No. 413,301, Sep. 28, 1989, abandoned, said Ser. No. 688,326, is a continuation-in-part of Ser. No. 588,922, Sep. 27, 1990, which is a continuation-in-part of Ser. No. 210,405, Jun. 23, 1988, abandoned, which is a continuation-in-part of Ser. No. 130,529, Dec. 9, 1987, abandoned, which is a continuation-in-part of Ser. No. 68,176, Jun. 30, 1987, abandoned.

[51] Int. Cl.[6] .......................... C07H 21/04; C12Q 1/68
[52] U.S. Cl. .................................... 536/24.31; 435/6
[58] Field of Search ........................ 435/6; 536/24.31

[56] References Cited
PUBLICATIONS

Kaufman et al, Immunogenetics, vol. 30, 1989, pp. 440–451.
Miller et al, Proc. Natl. Acad. Sci. USA, vol. 88, 1991, pp. 4377–4381.

*Primary Examiner*—Mindy B. Fleisher
*Attorney, Agent, or Firm*—Edward S. Irons

[57] ABSTRACT

The major histocompatibility complex (MHC) of domesticated fowl, the B system, is known to contain three subregions which are identified as B-F, B-G and B-L. This invention includes a cDNA clone encoding a B-G antigen of the B system. MHC haplotyping is accomplished by use of novel probes provided by clones to detect restriction fragment length polymorphism (RFLP) patterns typical for various B-G subregion alleles.

Additional information concerning this invention is set forth in the attached manuscript entitled "Hypervariable sequence diversity in Ig V-like and leucine heptad domains in chicken histocompatibility B-G antigens".

8 Claims, 34 Drawing Sheets

```
         10          20          30          40
          |           |           |           |
GAC ATC AGA TGG ATC CAG CAG CGG TCC TCT CGG CTT GTG CAC CAC
Asp Ile Arg Trp Ile Gln Gln Arg Ser Ser Arg Leu Val His His 50          60          70          80          90
      |           |           |           |           |
TAC CGA AAT GGA GTG GAC CTG GGG CAC ATG GAG GAA TAT AAA GGG
Tyr Arg Asn Gly Val Asp Leu Gly His MET Glu Glu Tyr Lys Gly 100         110         120         130
          |           |           |           |
AGA ACA GAA CTG CTC AGG GAT GGT CTC TCT GAT GGA AAC CTG GAT
Arg Thr Glu Leu Leu Arg Asp Gly Leu Ser Asp Gly Asn Leu Asp 140         150         160         170         180
      |           |           |           |           |
TTG CGC ATC ACT GCT GTG ACC TCC TCT GAT AGT GGC TCC TAC AGC
Leu Arg Ile Thr Ala Val Thr Ser Ser Asp Ser Gly Ser Tyr Ser 190         200         210         220
          |           |           |           |
TGT GCT GTG CAA GAT GGT GAT GCC TAT GCA GAA GCT GTG GTG AAC
Cys Ala Val Gln Asp Gly Asp Ala Tyr Ala Glu Ala Val Val Asn 230         240         250         260         270
      |           |           |           |           |
CTG GAG GTG TCA GAC CCC TTT TCT ATG ATC ATC ATC CTT TAC TGG
Leu Glu Val Ser Asp Pro Phe Ser MET Ile Ile Ile Leu Tyr Trp 280         290         300         310
          |           |           |           |
ACA GTG GCT CTG GCT GTG ATC ATC ACA CTT CTG GTT GGG TCA TTT
Thr Val Ala Leu Ala Val Ile Ile Thr Leu Leu Val Gly Ser Phe 320         330         340         350         360
      |           |           |           |           |
GTC GTC AAT GTT TTT CTC CAT AGA AAG AAA GTG GCA CAA GAG CAG
Val Val Asn Val Phe Leu His Arg Lys Lys Val Ala Gln Glu Gln 370         380         390         400
          |           |           |           |
AGA GCT GAA GAG AAA AGA TGC AGA GTT GGT GGA GAA AGC TGC AGC
Arg Ala Glu Glu Lys Arg Cys Arg Val Gly Gly Glu Ser Cys Ser 410         420         430         440         450
      |           |           |           |           |
ATT GGA GAG AAA AGA TGC AGA GTT GGC GGA ACA AGC AGC GCA ATC
Ile Gly Glu Lys Arg Cys Arg Val Gly Gly Thr Ser Ser Ala Ile 460         470         480         490
          |           |           |           |
GAA GCA AAG AGA TGC AAT GTT GGA CAA ACA CGT TCT AAA CTG GAG
Glu Ala Lys Arg Cys Asn Val Gly Gln Thr Arg Ser Lys Leu Glu 500         510         520
      |           |           |
GAA AGA CAG AGC AAG TGG AGA TTG GAA TTC
Glu Arg Gln Ser Lys Trp Arg Leu Glu Phe
```

FIG. 6

```
                3         9         15        21        27        33        39        45
                |         |         |         |         |         |         |         |
  1  GAC ATC AGA TGG ATC CAG CAG CGG TCC TCT CGG CTT GTG CAC CAC
 46  TAC CGA AAT GGA GTG GAC CTG GGG CAG ATG GAG GAA TAT AAA GGG
 91  AGA ACA GAA CTG CTC AGG GAT GGT CTC TCT GAT GGA AAC CTG GAT
136  TTG CGC ATC ACT GCT GTG ACC TCC TCT GAT AGT GGC TCC TAC AGC
181  TGT GCT GTG CAA GAT GGT GAT GCC TAT GCA GAA GCT GTG GTG AAC
226  CTG GAG GTG TCA GAC CCC TTT TCT ATG ATC ATC CTT TAC TGG ACA
271  GTG GCT CTG GCT GTG ATC ATC ACA CTT CTG GTT GGG TCA TTT GTC
316  GTC AAT GTT TTT CTC CAT AGA AAG AAA GTG GCA CAG AGC AGA GAG
361  CTG AAG AGA AAA GAT GCA GAG TTG GTG GAG AAA GCT GCA GCA TTG
406  GAG AGA AAA GAT GCA GAG TTG GCG GAA CAA GCA GCG CAA TCG AAG
451  CAA AGA GAT GCA ATG TTG GAC AAA CAC GTT CTA AAA CTG GAG GAA
496  AAG ACA GAC GAA GTG GAG ATT GGA ATT C
```

FIG. 7

```
               3         9        15        21        27        33        39        45
               |         |         |         |         |         |         |         |
  1   CGG TGA ACA GAT GGA GAG AAG GAA TGC AAA GTT GGA GGC AGC AGC
 46   TGT AAA ACT GGG ACA CAA AGC TAA AGA ATC AGA GAA ACA GAA ATC
 91   GGA GCT GAA GGA GCG CCA TGA GGA GAT GGC AGA ACA AAC TGA AGC
136   AGT GGT GGT AGA AAC TGA AGA ATA GGA AAA ACC ATC TGA AGA ATC
181   AGA TTG AGA GAT GAA CTG CGC CTC ACA ATA AGC ACA GGA GTT AAG
226   CTT CTT AGA TCA ATA ACT GCA CAG CAT ACA AAA CCA CAA TAA CTC
271   AAA CAG AGT AAG GAG GAG CCA GTG TTT GTG TTG AGT GAG AAC ACT
316   GCA GTT CTG TCA GCC AAA GCT GCC TGA GGG ACC GCC CAA TTG AGG
361   GTG TGT GAC CTC CAA CTC AAA TCC AGT TGG AAG AAA GAA ACC ATA
406   GAA AGG AAG GAA AGG GGA GGA AGA CAG AGA TCC TGG AAG AGA TAT
451   GGG CAT TTG GGG AAA TAG TGT GAT CAT GTA TCA GGC TTT GTG GAC
496   ATC TAA TGA ATA TGT CAT GCT TTT GTA ACT ACA AGC ATG CAC GCA
541   GAA ACA AAG GTA GAA AAC TGC TTT GGG TGT TAG CAC TGT TCT CTG
586   TCA CTA TAT AAT AAA GAA TAC CTG CTG ATG GCA ATG GAA CAA AAA
631   AAA A
```

FIG. 11

```
           3         9        15        21        27        33        39        45
           |         |         |         |         |         |         |         |
   1   ATC CGT TCG AGC TCT CTC CTC CTA CAG CTG CTG CCC TCA TAT TCT
  46   CCC CAC ACT TCT TCC CCA TAT TCT TTC CAA ATC CTC TTC CCC ATC
  91   TCC TCC ACC GTC TCT TTC TCA GAG TCC TTC CTC TCT CTC CCT AAA
 136   TTC TTC CCC CCT CCT CTC CTC CAG CAC AGA TGC GCT TCA CAT CGG
 181   GAT GCA ACC ACC CCA GTT TCA CCC TCC CCT GGA GGA CCC TCC TGC
 226   CTT ATC TCG TGG CTC TGC ACC TCC TCC AGC CGG GAT CAG CCC AGC
 271   TCA GGG TGG TGG CGC CGA GCC TCC GTG TCA CTG CCA TCG TGG GAC
 316   AGG ATG TCG TGC TGC GCT GCC ACT TGT GCC CTT GCA GGG ATG CTT
 361   GGA GAT TGG ACA TCA GAT GGA TCC TGC AGC GGT CCT CTG GTT TTG
 406   TGC ACC ACT ATC AAA ATG GAG TGG ACC TGG GGC AGA TGG AGG GAT
 451   ATA AAG GGA GAA CAG AAC TGC TCA GGG ATG GTC TCT ATG ATG GAA
 496   ACC TGG ATT TGC GCA TCA CTG CTG TGA GCA CCT CCG ATA GTG GCT
 541   CAT ACA GCT GTG CTG TGC AGG ATG GTG ATG GCT ATG CAG ACG CTG
 586   TGG TGG ACC TGG AGG TGT CAG ATC CCT TTT CCC AGA TCG TCC ATC
 631   CCT GGA AGG TGG CTC TGG CTG TGG TCG TCA CAA TTC TCG TTG GGT
 676   CAT TTG TCA TCA ATG TTT TTC TCT GTA GGA AGA AAG CGG CAC AGA
 721   GCA GAG AGC TGA GTG AGT CCT TCC AGC CCC TTC CAC CAC CAA AGT
 766   CCC TTT AAT GGA ACT GAT AGA AGA CTG CAG AGT GCT GGG TTT ATG
 811   CCT TGT GCT GGG GCC ATG GGA TCT ATG GGA CCT TGG GAT GTG TTG
 856   GGG CCG TGG GAT GTG CTG GGG TCG TGG GAT CTG TCA ACC CTG ATT
 901   GAT CCA CTT CAG AAC TCT TGC CCA ATC GGT TCC TTC CGA TTC ATT
 946   TAA CTC CTT CTT GAG GCC AAA GTG GTC ATT GGC CAC ATC CCA TAA
 991   AAA AGG GTT TGG GGT CAG GGT GTG GGA GCT GAT CGC ATG GAA ACG
1036   TGT CCC CTC TGA CCA TGC ATT TCA TTT GCT TCT ATT TTG CAG AGA
1081   GAA AAG ATG CAG CGT TGG CGG AAC TAG ATG AGA TAT CGG GTT TAA
```

FIG. 12A

```
1126  GTG CTG AAA ATC TGA AGC AAT TAG CTT CAA AAC TGA ACG AAA ATG
1171  CTG ACG AAG TGG AGG ATT GCA ATT CAG AGC TGA AGA AAG ACT GTG
1216  AAG AGA TGG GTT CTG GCG TTG GAG ATC TGA AGG AAC TGG CTG CAA
1261  AAT TGG AGG AAT ATA TTG CAG TGA ATC GGA GAA GGA ATG TAA AGT
1306  TGA ATA ATA TAG CTG CCA AAC TGG CAC AAC AAA CTA AAG AAT TGG
1351  AGA AAC AGC ATT CAC AGT TCC ACA GAC ACT TTC AGC GTA TGG ATT
1396  TAA GTG CTG TAA ACC AGA AGA AAC TGG TTA CAA AAC TGG AGG AAC
1441  ACT TTG AAT GGA TGG AGA GAA GGA ATG TAA AGT TGG AGA TAC CAG
1486  CTG TAA TAC TGG GGC AAC AAG CTA AAG AAT CAG AGA AAC AGA AAT
1531  CGG AGC TGA AGG AGC GCC ATG AGG AGA TGG CAG AAC AAA CTG AAG
1576  CAG TGG TGG TAG ATA CTG AAG AAG CGG AAA AAC CAT CTG AAG AAT
1621  TGG ATT GAG AGA TGA ACT GCG CCT CAC AGT AAC CAC AGG AGT TAA
1666  GCT TCA TAG ATC AAT GAC TGC ACA GCA TAC AAA AAC CAC GAT ACC
1711  TCA AAC AGA GCA AGG AAA TCC ACA GCG AGA ACA AGA GGA GCC AGT
1756  GTT TGT GTT GAG TGA GAA CAC TGC AGT TCT
```

FIG.12B

```
          3         9        15        21        27        33        39        45
          |         |         |         |         |         |         |         |
   1  TTC TGC CCT CAT ATT CTC CCC ACA CTT CTT CCC CAT ATT CTT TCC
  46  AAA TCC TCT TCC CCA TCT CCT CCA TCG TCT CCT TCT CAG AGT CCT
  91  TCC TCT CTC TCC CTA AAT TCT TCC CCC CTC CTC TTC TCC AGC ACA
 136  GAT GGC CTT CAC ATC GGG CTG CAA CCA CCC CAG TTT CAC CCT CCC
 181  CTG GAG GAC CCT CCT GCC TTA TCT CGT GGC TCT GCA CCT CCT CCA
 226  GCC GGG ATC AGC CCA GAT CAC GGT GGT GGC ACC GAG CCT CCG TGT
 271  CAC TGC CAT CGT GGG ACA GGA TGT TGT GCT GCG CTG CCA CTT GTC
 316  CCC ATG CAA GGA TGT TCG GAA TTC AGA CAT CAG ATG GAT CCA GCA
 361  GCG GTC CTC TCG GCT TGT GCA CCA CTA CCG AAA TGG AGT GGA CCT
 406  GGG GCA GAT GGA GGA ATA TAA AGG GAG AAC AGA ACT GCT CAG GGA
 451  TGG TCT CTC TGA TGG AAA CCT GGA TTT GCG CAT CAC TGC TGT GAC
 496  CTC CTC TGA TAG TGG CTC CTA CAG CTG TGC TGT GCA AGA TGG TGA
 541  TGC CTA TGC AGA AGC TGT GGT GAA CCT GGA GGT GTC AGA CCC CTT
 586  TTC TAT GAT CAT CCT TTA CTG GAC AGT GGC TCT GGC TGT GAT CAT
 631  CAC ACT TCT GGT TGG GTC ATT TGT CGT CAA TGT TTT TCT CCA TAG
 676  AAA GAA AGT GGC ACA GAG CAG AGA GCT GAA GAG AAA AGA TGC AGA
 721  GTT GGT GGA GAA AGC TGC AGC ATT GGA GAG AAA AGA TGC AGA GTT
 766  GGC GGA ACA AGC AGC GCA ATC GAA GCA AAG AGA TGC AAT GTT GGA
 811  CAA ACA CGT TCT AAA ACT GGA GGA AAA GAC AGA CGA AGT GGA GAA
 856  CTG GAA TTC AGT GCT GAA AAA AGA CAG TGA AGA GAT GGG TTA TGG
 901  CTT TGG AGA TCT GAA GAA ACT GGC TGC AGA ACT GGA GAA ACA CTC
 946  TGA AGA GAT GGG GAC AAG GGA TTT AAA GTT GGA GCG ACT AGC TGC
 991  CAA ACT GGA ACA TCA AAC TAA AGA ATT GGA GAA ACA GCA TTC ACA
1036  GTT CCA GAG ACA CTT TCA GAA TAT GTA TTT AAG TGC TGG AAA ACA
1081  GAA GAA AAT GGT TAC AAA ACT GGA GGA ACA CTG TGA ATG GAT GGT
1126  GAG AAG GAA TGT AAA GTT GGA GAT ACC AGC TGT AAA AGT GGG GCA
```

FIG.13A

```
1171  ACA AGC TAA AGA ATC AGA GGA ACA GAA ATC GGA GCT GAA GGA GCA
1216  CCA TGA GGA GAC GGG GCA ACA AGC TAA AGA ATC AGA GAA ACA GAA
1261  ATC GGA GCT GAA GGA GCG CCA TGA GGA GAT GGC AGA ACA AAC TGA
1306  AGC AGT GGT GGT AGA AAC TGA AGA ATA GGA AAA ACC ATC TGA AGA
1351  ATT GGA TTG AGA GAT GAA CTG CGC CTC GCA GTA ACC ACA GGA GTT
1396  AAG CTT CAT AGA TCA ATA ACT GCA CAG CAT ACA AAA CCA CAA TAA
1441  CTC AAA CAG GGT AAG GAG GAG CCA GTG TTT GTG TTG AGT GAG AAC
1486  ACT GCA GTT CTG TCA GCC AAA GCT GCC TGA GGG ACC GCC CAA TTG
1531  AGG GTG TGC GAC CTC AAC TC AAA GCC AAT GGA AG AAA GAA ACC
1576  ATA GAA AGG AAG AAA AGG GGA GGA AGA CAG AGA TCC TGG AAG AGA
1621  TAT GGG CAT TTG GGG AAA TAG TGT GAC CAT GTA TCA GGC TTT GTG
1666  GAC ATC TAA CGA ATA TGT CAT GTT TTT GTA AAT ACA AGC ATG CAC
1711  GCA GAA ACA AAG GGA GAA AAC TGC TTT GGG TGT TAG CAC TGT TCT
1756  CTG TCC CTA TAT AAT AAA GAA TAC CTG CTG ATG GCA AAA AAA AAA
1801  AAA AAA AAA AAA AAA A
```

FIG. 13B

```
               3         9        15        21        27        33        39        45
               |         |         |         |         |         |         |         |
   1   AAA TGA AGA CTT CAG GAT CCT TCC ATA AAA GCT ATC AGT TTG ACT
  46   TCA GAG AGG GCT ATT CTC GGT GTT TGC AAG AAG CTT TCC ATC GTC
  91   TCC TTC TCA GAG TCC TTC CTC TCT CTC CCT AAA TTC TTC CCC CCT
 136   CCT CTT CTC CAG CAC AGA TGG CCT TCA CAT CGG GCT GCA ACC ACC
 181   CCA GTT TCA CCC TCC CCT GGA GGA CCC TCC TGC CTT ATC TCG TGG
 226   CTC TGC ACC TCC TCC AGC CGG GAT CAG CCC AGA TCA CGG TGG TGG
 271   CAC CGA GCC TCC GTG TCA CTG CCA TCG TGG GAC AGG ATG TTG TGC
 316   TGC GCT GCC ACT TGT CCC CAT GCA AGG ATG TTC GGA ATT CAG ACA
 361   TCA GAT GGA TCC AGC AGC GGT CCT CTC GGC TTG TGC ACC ACT ACC
 406   GAA ATG GAG TGG ACC TGG GGC AGA TGG AGG AAT ATA AAG GGA GAA
 451   CAG AAC TGC TCA GGG ATG GTC TCT CTG ATG AAC CTG GAT TTG C
 496   GCA TCA CTG CTG TGA CCT CCT CTG ATA GTG GCT CCT ACA GCT GTG
 541   CTG TGC AAG ATG GTG ATG CCT ATG CAG AAG CTG TGG TGA ACC TGG
 586   AGG TGT CAG ACC CCT TTT CTA TGA TCA TCC TTT ACT GGA CAG TGG
 631   CTC TGG CTG TGA TCA TCA CAC TTC TGG TTG GGT CAT TTG TCG TCA
 676   ATG TTT TTC TCC ATA GAA AGA AAG TGG CAC AGA GCA GAG AGC TGA
 721   AGA GAA AAG ATG CAG AGT TGG TGG AGA AAG CTG CAG CAT TGG AGA
 766   GAA AAG ATG CAG AGT TGG CGG AAC AAG CAG CGC AAT CGA AGC AAA
 811   GAG ATG CAA TGT TGG ACA AAC ACG TTC TAA AAC TGG AGG AAA AGA
 856   CAG ACG AAG TGG AGA ATT GGA ATT CAG TGC TGA AAA AAG ACA GTG
 901   AAG AGA TGG GTT ATG GCT TTG GAG ATC TGA AGA AAC TGG CTG CAG
 946   AAC TGG AGA AAC ACT CTG AAG AGA TGG GGA CAA GGG ATT TAA AGT
 991   TGG AGC GAC TAG CTG CCA AAC TGG AAC ATC AAA CTA AAG AAT TGG
1036   AGA AAC AGC ATT CAC AGT TCC AGA GAC ACT TCA GAA TA TGT ATT
1081   TAA GTG CTG GAA AAC AGA AGA AAA TGG TTA CAA AAC TGG AGG AAC
1126   ACT GTG AAT GGA TGG TGA GAA GGA ATG TAA AGT TGG AGA TAC CAG
```

FIG. 14A

```
1171  CTG TAA AAG TGG GGC AAC AAG CTA AAG AAT CAG AGG AAC AGA AAT
1216  CGG AGC TGA AGG AGC ACC ATG AGG AGA CGG GGC AAC AAG CTA AAG
1261  AAT CAG AGA AAC AGA AAT CGG AGC TGA AGG AGC GCC ATG AGG AGA
1306  TGG AAC AAA CTG AAG CAG TGG TGG TAG AAA CTG AAG AAT AGG AAA
1351  AAC CAT CTG AAG AAT TGG ATT GAG AGA TGA ACT GCG CCT CGC AGT
1396  AAC CAC AGG AGT TAA GCT TCA TAG ATC AAT AAC TGC ACA GCA TAC
1441  AAA ATC ACA ATA ACT CAA ACA GGG TAA GGA GGA GCC AGT GTT TGT
1486  GTT GAG TGA GAA CAC TGC AGT TCT GTC AGC AAA GC TGC CTG AGG
1531  GAC CGC CCA ATT GAG GGT GTG CGA CCT CCA ACT CAA AGC CAA TTG
1576  GAA GAA AGA AAC CAT AGA AAG GAA GAA AAG GGG AGG AAG ACA GAG
1621  ATC CTG GAA GAG ATA TGG GCA TTT GGG GAA ATA GTG TGA CCA TGT
1666  ATC AGG CTT TGT GGA CAT CTA ACG AAT ATG TCA TGT TTT TGT AAA
1711  TAC AAG CAT GCA CGC AGA AAC AAA GGG AGA AAA CTG CTT TGG GTG
1756  TTA GCA CTG TTC TCT GTC CCT ATA TAA TAA AGA ATA CCT GCT GAT
1801  GGC AAT GGA AAA AAA AAA AAA A
```

FIG. 14B

```
              3         9        15        21        27        33        39        45
              |         |         |         |         |         |         |         |
   1   ATC CGC TCG AGC TCT CTC CTC CTA CAG TTT CTG CCC TCA TAT TCT
  46   CCC CAC ACT TCT TCC CCA TAT TCT TTC CAA ATC CTC TTC CCC ATC
  91   TCC TCC ATC GTC TCC TTC TCA GAG TCC TTC CTC TCT CTC CCT AAA
 136   TTC TTC CCC CCT CCT CTT CTC CAG CAC AGA TGG CCT TCA CAT CGG
 181   GCT GCA ACC ACC CCA GTT TCA CCC TCC CCT GGA GGA CCC TCC TGC
 226   CTT ATC TCG TGG CTC TGC ACC TCC TCC AGC CGG GAT CAG CCC AGA
 271   TCA CGG TGG TGG CAC CGA GCC TCC GTG TCA CTG CCA TCG TGG GAC
 316   AGG ATG TTG TGC TGC GCT GCC ACT TGT CCC CAT GCA AGG ATG TTC
 361   GGA ATT CAG ACA TCA GAT GGA TCC AGC AGC GGT CCT CTC GGC TTG
 406   TGC ACC ACT ACC GAA ATG GAG TGG ACC TGG GGC AGA TGG AGG AAT
 451   ATA AAG GGA GAA CAG AAC TGC TCA GGG ATG GTC TCT CTG ATG GAA
 496   ACC TGG ATT TGC GCA TCA CTG CTG TGA CCT CCT CTG ATA GTG GCT
 541   CCT ACA GCT GTG CTG TGC AAG ATG GTG ATG CCT ATG CAG AAG CTG
 586   TGG TGA ACC TGG AGG TGT CAG ACC CCT TTT CTA TGA TCA TCC TTT
 631   ACT GGA CAG TGG CTC TGG CTG TGA TCA TCA CAC TTC TGG TTG GGT
 676   CAT TTG TCG TCA ATG TTT TTC TCC ATA GAA AGA AAG TGG CAC AGA
 721   GCA GAG AGC TGA GTG AGT CCT TCC ATC CCC ATC ACC AAC CA AAG
 766   TCC CTT TAA TGG AAC TGA CAG CAG ACT GCA GAG TGC TGG GTT ATG
 811   CCA TGT GCT GGG GCC ATG AGC TAT GTT GAG GCT TTG GAA TGT GTT
 856   GGG GTT GTG GGA TGT ACT GGG GTC GTG GGA TGT GTT ATT CCT GGC
 901   TGA TTC ACG TGG AAA AAC CTT TCA CAA TCG GTT CCT TCC AGT TTG
 946   TTT AAT TCC TTC TTG GGC CCA AAG TGG TCA TTG GAC TCC TCC CAG
 991   AAA AAA GGG TTT GGG GTC AGG GTG TGA GAG CTG ATG GCA CGG AAA
1036   CGT GTC CCC TCT GAC CAT GCA TTT CAT TTG CTT CTA TTT TGC AGA
1081   GAG AAA AGA TGC AGA GTT GGG TAA GTC TCC TTC CCT AAA GCG AGG
1126   GAA TTC AGG GTG TCC CCA TGG CAT CAG CCG TGG AAT TAG TAG CTG
1171   TCC TCT CTG ACA ATT CAC TGC TCT GCT CTT TCC TTT CCA GTG GAG
1216   AAA GCT GCA GCA TTG GGT GAG TTA TAT TCC CCA AGC CAA AGT ACT
1261   TTG GGT CTT CCC ATT GGA AGT TAT TTC CTC AGA CCA TCC TTT CTG
1306   TTG TGT TTG CTT TGG CAT CAT GTT AGT AAA ATG CCT TCT TGG GAC
1351   CAA AGT GGT CAT TGG CCA CTT CCC AGA AAA AAA GGT TTG GGG TCA
1396   GGG TGT GGG AGC TGA TGG CAT GGA AAC ATG TTC CCT CTG ACC ATG
1441   CAT TTC CTT TGC TTC TTT TTC CAG AGA GAA AAG ATG CAG AGT TGG
1486   CGG AAC AAG CAG CGC AAT CGA GTG AGT CTC CCC CTC CAT TTT TAT
```

FIG.15A

```
1531  TAT TTT TAA ATG TTC AGC CTC CGG TAG CTG TGG GAT GAG ATG TTC
1576  CTC TCA TCA TAC ACT GAC TCT GCT TTT CCT TTG CAG AGC AAA GAG
1621  ATG CAA TGT TGG ACA AAC ACG TTC TAA AAC TGG GTG AGT CCT CAC
1666  TCC CAA ATT ATA AAG CAA AGG GTT CTG CCT GTG TGA GCT GTG GGA
1711  TCA GAC GTT CCT CTC ATC GTG CAT TGC TTT TCT CTT TCT TTT TCA
1756  GAG GAA AAG ACA GAC GAA GTG GAG AAT TGG AAT TCA GTG CTG AGT
1801  AAG TTG CAG TCA CTG AAC TGA GGG AAT GTG GGG TCT TCC TAA GGG
1846  ACT GCG TAG GGG AGA AGT TCC CAT GCA CTG CTT TTC TCT TTC TTT
1891  TCC AGA AAA AGA CAG TGA AGA GAT GGG TTA TGG CTT TGG AGA TCT
1936  GAG TAA GTC TCC CTC CCA ACA TGG AAG GAA TTT ATG GTC TTA GCA
1981  TGG GAT CAG CCA TGG GAT GAT CAT CTG ACC CCT CTC ATC ATG CAA
2026  TTC ATA TTT GTT CCT TTT GCA GAG AAA CTG GCT GCA GAA CTG GAG
2071  AAA CAC TCT GAA GAG ATG GGG ACA AGG GAT TTA AAG TTG GAG CGA
2116  CTA GCT GCC AAA CTG GAA CAT CAA ACT AAA GAA TTG GAG AAA CAG
2161  CAT TCA CAG TTC AGA GAC ACT TTT CAG AAT ATG TAT TTA AGT GCT
2206  GGA AAA CAG AGT AAG TCT CCC TCC CTG CAC AGA AGG AAC TTA CGG
2251  TTT TCC CAT GGG ATC AGC CAT GGG ACG ATC ATC CGA CTC TTC TCA
2296  TCA TGA ATT TCG TCT TTC TTT CTT TTG CAG AGA AAA TGG TTA CAA
2341  AAC TGG AGG AAC ACT GTG AAT GGA TGG TGA GAA GGA ATG TAA AGT
2386  TGG AGA TAC CAG CTG TAA AAG TGG GGC AAC AAG CTA AAG AAT CAG
2431  AGG AAC AGA AAT CGG AGC TGA AGG AGC ACC ATG AGG AGA CGG GGC
2476  AAC AAG CTA AAG AAT CAG AGA AAC AGA AAT CGG AGC TGA AGG AGC
```

FIG.15B

```
2521  GCC ATG AGG AGA TGG CAG AAC AAA CTG AAG CAG TGG TGG TAG AAA
2566  CTG AAG AAT AGG GTG AGT CTT TCC CAA ACC AAA GCA ATA CGG GGT
2611  TTC CCA TGG CAT GAC AAG CTG TCC CAC CTC AGC ATC CGT TCC TTT
2656  TTC TTT CTT TTC CAG AAA AAC CAT CTG AAG AAT TGG ATT GAG AGA
2701  TGA ACT GCG CCT CGC AGT AAC CAC AGG AGT TAA GCT TCA TAG ATC
2746  AAT AAC TGC ACA GCA TAC AAA ACC ACA ATA ACT CAA ACA GGG TAA
2791  GGA GGA GCC AGT GTT TGT GTT GAG TGA GAA CAC TGC AGT TCT GTC
2836  AGC CAA AGC TGC CTG AGG GAC CGC CCA ATT GAG GGT GTG CGA CCT
2881  CCA ACT CAA AGC CAA TTG GAA GAA AGA AAC CAT AGA AAG GAA GAA
2926  AAG GGG AGG AAG ACA GAG ATC CTG GAA GAG ATA TGG GCA TTT GGG
2971  GAA ATA GTG TGA CCA TGT ATC AGG CTT TGT GGA CAT CTA ACG AAT
3016  ATG TCA TGT TTT TGT AAA TAC AAG CAT GCA CGC AGA AAC AAA GGG
3061  AGA AAA CTG CTT TGG GTG TTA GCA CTG TTC TCT GTC CCT ATA TAA
3106  TAA AGA ATA CCT GCT GAT GGC AAA AAA AA
```

FIG. 15C

```
         3         9        15        21        27        33        39        45
         |         |         |         |         |         |         |         |
   1  CGA TGT TCG GAA TTC AGA CAT CAG ATG GAT CCA GCT GCG GTC CTC
  46  TAG GAT TGT GCA CCA CTA CCA AAA TGG AGA GGA CCT GGA TCA GAT
  91  GGA GGA ATA TGA AGG GAG AAC AGA ACT GCT CAG GGA TGG TCT CTC
 136  TGA TGG AAA CCT GGA TTT GCG CAT CAC TGC TGT GAG CTC CTC TGA
 181  CAG TGG CTC GTA CAG CTG TGC TGT GCA AGA TGA TGA TGG CTA TGC
 226  AGA AGC TGT GGT GAA CCT GGA GGT GTC AGA TCC CTT TTC CCA GAT
 271  CGT CCA TCC CTG GAA GGT GGC TCT GCC TGT GGT CGT CAC AAT TCT
 316  CGT TGG GTC ATT TGT CAT CAT TGT TTT TCT CTA TAG GAA GAA AGT
 361  GGC ACA GAG CAG AGA GCT GAA GGG AAA AGA TGC AGC ACT GGC GGA
 406  ACT ACC TGC GAT ATT GGG TGT ATG TAC TGC AAA TTT GAA GAT CCT
 451  AGC TTC AAA ACT GAT GAA ACA AAT GGA AAA ATT GGA GAT TCA GAA
 496  TTC ACT CTT GAA GAA ACG GTA TGA GAT TAC GGA GGA ACT GGC TGC
 541  AGA TCT GGA GGA ACA TCT TGC TGA GAA GGA TTT AAG CAC TGC AGA
 586  TCT GAA GCT ACT AGC TGC AAA ACT GGT GGA ACA AAG AGA AGC AGT
 631  GGA GGA ACG GGA TTC ACA GCT GAG GAA ACA GTA TGA AAA GTT GGG
 676  TTC GCG TGC TAC AAA TCT GAA GAC ACA ACT AAA AAA GTT GGA GAA
 721  CGA AAT TGA AGA AGT GGA GAA ACA CCT TAA AAA GAT TGG TAT ACG
 766  TGC TCC TAA TCT GAA GCT ACA CAT GGC AGA ACT GGT GGA TCA AGC
 811  TGA AGC AGT GGA GAA ACG GAA ATC AGA GCT GAA GAG CTA TTT GAC
 856  AAA TAT AGG TTT ACG TGC TGC AGA GCT GAA AAA ATA CAT TGC AGC
 901  ACT GGA GAA ACG AAT TGA AGC ATT GGA AAC TAA AGA ATT GGA ACA
 946  ACC ATC TAA AGA ACA GGA TTG AAA GAT GAA CTG CGC CTC ACA GTA
 991  ACC ACA GGA GTT AAG CTT CAT AGA CTG CAG ACT GCA CAG GAT AGC
1036  AAC ATC GCC ATA ACG CAA AGC AAG CAA GGA AAT CCA CAC GGG GAA
1081  CAA GAG GAG CCA GTG TTT GTA TTG AGT GAG AAC ACT GCA GTT CTG
1126  CAA GCC ACA GCT GCC TGA GGG ACC AGC AAA CTG AGG GTG TGT GAC
1171  CTC CAT CTC AAA TCC AGT TGG AAG AAA GAC ACC ATA GAA AAG AAG
1216  ACT ACA AGA GGA AGA CAG AGA TCC TGG AAA AGG GAC AGA CAT TTT
1261  GGG AAT GAA CAT GGC CAT GTA TCA GGG TTT GAG GAA TTC TAA TGA
1306  ATA TGT AAG GCT TCT GGA AAT ATA AAC ATG CAC ACA GAA GTA AAG
1351  GTA GAA AAC TGC TTT GGG TGT TAA CAC TGT TCT CTA TCA CAA TAT
1396  AAT AAA GAA ATA CCT GCT GAT GGC GAT GGA AAA GAA AAA AAA AAA
1441  AAA AAA AAA
```

```
       ----,----+----,----+----,----+----,----+----,----+----,
   1   AAAGGAGTGAGTTGTGTACAGGGGGGTTAAATGCTTTATAGACAA            45
  46   GAAAGAAATTGCTCTAAAAGAGACTTATTCATCATCATCATCATC            90
  91   TTCCTCCTCCTCTTCTTCCTCTTCTTCGTCCTCTTCATCCTCTTC           135
 136   GTCTTCGTCCTCATCTTCCTCTTCTTCCTTCTTCTTCTTGCTCTT           180
 181   CTCGGCCTTGGCAACTACTTTTTTGCCTGCATCAACCTTCCCTTT           225
       ----,----+----,----+----,----+----,----+----,----+----,
 226   GGCCCGGTATGCAGCGATATCCTTCTCAGTCTCCTTCCTCTCTCT           270
 271   CCTTGGCCCAACTCCTCCCCCCTCCTCTTCTCCAGCACAGATGGC           315
 316   CTTCACATCGAGCTGCAACCACCCCAGTTTCACCCTCCCCTGGAG           360
 361   GACCCTCCTGCCTTATCTCGTGGCTCTGCACCACCTCCAGCCGGG           405
 406   ATCAGCCCAGCTCAGGGTGGTGGCACCGAGCCTCCGTGTCACTGC           450
       ----,----+----,----+----,----+----,----+----,----+----,
 451   CATTGTGGGACAGGACGTCGTCTGCGCTGTCACTTGTCTCCTTGC           495
 496   AAGAATGCTTGGAATTCAGACATCAGATGGATCCAGCACCGTTCC           540
 541   TCTAGGATTGTGCACCACTACCAAGACGGAGTGGACCTGGAGCAG           585
 586   ATGGAGGAATATAAAGGGAGGACAGAACTGCTCAGGGATGGTCTC           630
 631   TCTGATGGAAACCTGGATTTGCGCATCACTGCTGTGAGCACCTCT           675
       ----,----+----,----+----,----+----,----+----,----+----,
 676   GATAGTGGCTCATACAGCTGTGCTGTGCAGGATGATGATGGCTAT           720
 721   GCAGAAGCTTTGGTGGAGCTGGAGGTGTCAGATCCCTTTTCCCAG           765
 766   ATCGTCCATCCCTGGAAGGTGGCTCTGGCTGTGATCGTCACAATT           810
 811   CTGGTTGGGTCATCGGTCATCATTGTTTTTCTCTGTAGAAAGAAA           855
 856   GAGAGAAAAGATGGAGAGTTGGCGGAACAAGCTGAAATACTGGAG           900
       ----,----+----,----+----,----+----,----+----,----+----,
 901   AGAAAAGATGCAATGTTGACGGAACAAGCTGAAACACTGGAGAAA           945
 946   AAAGATGTAATGTTGAAGGAACAAGCTATGATAGCGGAATCAAAT           990
 991   GCTGAAGATCTGAAGAAACTGGCTGCGAAACTGGAGAAACACTCT          1035
1036   GAAGAGATGGGGACAAGGGATTTAAAGTTGGATAAATTAGCTGCC          1080
1081   AAACTGGAACATCAAACTAAAGAATTGGAGAAACAGAAATCGGAG          1125
       ----,----+----,----+----,----+----,----+----,----+----,
1126   CTGAAGAGTCACTTTCAGTATATGGATTTCAATGCTGGAAAACAG          1170
1171   AAGAAAATGGTTACAAAACTGGAGGAACACTATGAATGGATGGTG          1215
1216   ACAAGGAATGTAAAATTGGAGATACCAGCTATAAAAGTGGGGCAA          1260
1261   CAAGCTAAAGAATCAGAGGAACAGAAATCGGAGCTGAAGGAGCAC          1305
1306   CATGAGGAGATGGGGCAACAAGCTAAAGAATCAGAGGAACAGAAA          1350
       ----,----+----,----+----,----+----,----+----,----+----,
1351   TCGGAGCTGAAGGAGCACCATGAGGAGATGGGGCAACAAGCTAAA          1395
1396   GAATCAGAGGAACAGAAATCGGAGCTGAAGGAGCACCATGAGGAG          1440
1441   ATGGGGCAACAAGCTAAAGAATCAGAGGAACAGAAATCGGAGCTG          1485
1486   AAGGAGCACCATGAGGAGATGGGGCAACAAGCTAAAGAATCAGAG          1530
1531   GAACAGAAATCGGAGCTGAAGGAGCACCATGAGGAGATGGGGCAA          1575
       ----,----+----,----+----,----+----,----+----,----+----,
1576   CAAGCTAAAGAATCAGAGGAACAGAAATCGGAGCTGAAGGAGCAC          1620
1621   CATGAGGAGATGGGGCAACAAGCTAAAGAATCAGAGGAACAGAAA          1665
1666   TCGGAGCTGATGGTAGAAACTGAAGAAGCAGAAAAACCATCTGAA          1710
1711   GAATCAGATTGAGAGATGAACTGCGCCTCCCAATAAGCACAGGAG          1755
1756   TTAAGCTTCATAGATCAATGACTGTACAGCAAACAAAAACCACGA          1800
       ----,----+----,----+----,----+----,----+----,----+----,
1801   TAACTCAAACAGAGCAAGGAAATCCACAGCGAGAACAAGAAGAGC          1845
1846   CAGTGTTTGTGTTGAGTGAGAACACTGCAGTTCTGTCAGCCAAAG          1890
1891   CTGTCTGAGGGACCGCCAAATTGAGGGTGTCGAACCTCCAACTCA          1935
1936   AAGCCAATTGGAAGAAAGAAACCATAGAAAGGAAGAAAAGGGGAG          1980
1981   GGAGACAGAGATCCTGGAAAAGATATGGGCATTTGGGGAAATAGT          2025
       ----,----+----,----+----,----+----,----+----,----+----,
2026   GTGACCATGTATCAGGCTTTATGGAAATCTAACAAATATGTCATG          2070
2071   GTTTTGTAAATACAAGCATGCACGCAGAAACAAAGGTAGAAAACT          2115
2116   GCTTTGGGTGTTAGCACTGTTCTCTGTCCCTATATAATAAAGAAT          2160
2161   ACCTGCTGATGGCAAAAAAAAAAAAAAAAA                         2188
```

FIG. 18

```
        ----,----+----,----+----,----+----,----+----,
   1    TTGCAAGAATGCTTGGAGCTTAGATATCAGATGGATCCAGCTGCG    45
  46    GTCCTCTGGTTTTGTGCACCACTACCGAAATGGAGAGGACCTGGA    90
  91    GCAGATGACAGAATATAAAGGGAGAACAGAACTGCTCAGGAAGGG   135
 136    TCTTTCTGATGGAAACCTGGATTTGCGCATCACTGCTGTGAGCAC   180
 181    CTCCGATAGTGGCTCATACAGCTGTGTTGTGCAAGACGATGATGG   225
        ----,----+----,----+----,----+----,----+----,
 226    CTATGCAGAAGCGTTGGTGGAGCTGGAGGTGTCAGATCCCTTTTC   270
 271    CCAGATCGTCCATCCCTGGAAGGTGGCTCTGGCTGTGATCGTCAC   315
 316    AATTCTGGTTGGGTCATTTGTCATCATTGCTTTTCTCTATAGGAA   360
 361    GAAAGCGACACAGAGCAGAGAGCTGAAAAGAAAAGATGCAATGTT   405
 406    GGGAAGAAAAGATGCAGTGCTGGAGGAACTACCTGCGATATTAGA   450
        ----,----+----,----+----,----+----,----+----,
 451    TTCAAGTGCTGCAAATCTGAAGATACTAGCTTCAAAACTGGTGAA   495
 496    ACAAACTGAAAAATTGGACATACGGAATTCACTAATGAAGAAACA   540
 541    GTATGAAATGACAGAGAAACAAGCTGCAGAACTGGAGAAACACTT   585
 586    AATAAATACCGATTTAAGTGCTGCAGATCTGAAGATAGCAGCTGC   630
 631    AAAACTGGACAAACAAACTGAAGAACTGGACAAATGGAAATCAGC   675
        ----,----+----,----+----,----+----,----+----,
 676    ACTGAAGATACAATATGAAAAGTTGGGTTTACGTGCTGCAAATCT   720
 721    GAAGACACAAGTTACAGAACTGGCGAAACAAACTGAAGAAGTGGA   765
 766    AAATCACTATGAAGAGATGGGTTTACGTGCTCCTAATCTGAAGAA   810
 811    AAATATAGTAGAACTGGAGAAACAAACTGAGCACGTGGACAATCG   855
 856    GAAATCAGAGCTGAAGAAACAGTATGAAAATTTGGCTTCACATGC   900
        ----,----+----,----+----,----+----,----+----,
 901    TTCAGAGCTGAAGAAACAAGCTGAAGTACTGGAGGAACAAGCTGA   945
 946    ACAACTGGAGATTCAGAATTCACTGTTGAAGATACGCAATAAACA   990
 991    TAGGGAGAGAAAGAATGAAATGTTGGAGAAACAAACTGTAGAACA  1035
1036    GGAACAAACTGAAGAATGGGCAGAATCTAAAAAATCGGTGGTTGA  1080
1081    AACTAAAGAATTGGAACAACCATCTAAAGAACAGGATTGAGAGAT  1125
        ----,----+----,----+----,----+----,----+----,
1126    GAACTGCGCCTCACAGTAACCACAGGAGTTAAGCTTCATGGACTG  1170
1171    CTGACTGCACAGGATAGCAACACCGCCATAATGCAAAGCGAGCAA  1215
1216    GGAAATCCACAGCGAAAACAAGAGGAGCCAGTGTTTGTGTTGAGT  1260
1261    GAGAACACTGCAGTTCCATGAGCCAAACCTGCCTGAGGGACCGCC  1305
1306    CAATTGAGGGTGTGCGACCTCCAACTCAAAGCCAATTGGAAGAAA  1350
        ----,----+----,----+----,----+----,----+----,
1351    GAAACCATAGAAAGGAAGACTACAAGAGGAAGACAGAGATCCTGG  1395
1396    AAAAGGGATAGACATTTTGGGATTTAACATGGCCATGTATCAGGG  1440
1441    TTTGAGGAATTCTAACGTATATATAAGGCTTTTGGAAATATAAAC  1485
1486    AT                                             1487
```

FIG. 19

```
        ----,----+----,----+----,----+----,----+----,
   1    GGATGATCATCCGACTCTTCTCATCATAAATTCGTCTTCTTCTTT    45
  46    GCAGAGAAACTGGTTACAAAACTGGGTGAGTCCAACCTCCCAAAC    90
  91    TAAATTAAAAGCAGTCAGACTTTGTGAGCTGTGGGATGAGACGTT    135
 136    CTTCTCATCATGTGCTGCTTTCCTTTTACTTTTCCAGAGGAACAC    180
 181    TTTGAATGGATGGGTGAGTCTCCCCTCCCAAATTAAAAATGTTGG    225
        ----,----+----,----+----,----+----,----+----,
 226    GGTCTTCCTGTGTGAGCTGTGGGATGAGCTGTTCCTCCCATCATG    270
 271    CACTGGTTCTAATTTTCCTTTGCAGAGAGAAGGAATGTAAAGTTG    315
 316    GGTGAGTCTTCTTCCCCAACCAAAGGGATTTGGGGTCTTCCATGG    360
 361    GATCAGCCATGGGATGATAACCTGAACCTTATCACATATTTCTTA    405
 406    TTTGTTCTTTTTGCAGAGATACCAGATCTGTAATACTGGGTGAGT    450
        ----,----+----,----+----,----+----,----+----,
 451    CCTCCCTCCCAAATTAAATACAAAAGGGGATCTGCCTGTGTGAGC    495
 496    TGTGGGATGAGATGTTCCTCTCATCACGCATTATTTTCTCTTTCT    540
 541    TTTCCAGGGCAACAAGCTAAAGAATCAGGTGAGTCTTCTTCCCTG    585
 586    TCCCAAAGGACTATGGGTTTCCCATGGGATGACAAGCTGTGCCAC    630
 631    CTCCTCACGAGGTGCTTCTTCTTTCTTTTTTGCAGAGAAACAGAA    675
        ----,----+----,----+----,----+----,----+----,
 676    ATCGGAGCTGAGTAAGTTGCAGTCACTGAACTGAGGGAATGTGGG    720
 721    GTCTTCCCAAAGTCTTGTGTATGGGATGAAAAATCCCCTCTGACC    765
 766    ATGCACTGCTTTTCTCCTCCTTTGCCAGAGGAGCGCCATGAGGAG    810
 811    ATGGGTGAGTCTCCCCTCCCATATTAAAATCGTTGGGGTCTTCCT    855
 856    GTGTGAGCTGTGAGATGAGATGTTCCTCTCATCATGCGATGCTTT    900
        ----,----+----,----+----,----+----,----+----,
 901    TCTCTCTTTTCCAGCAGAACAAACTGAAGCAGTGGGTGAGTCTTT    945
 946    GTCCCCAACCCAAAGGAATATGGGGCAATCCATGGGATGACAAGC    990
 991    TGTCCCATCTCATCGTGCATTGCTTTCCTATTCCTTTTTTCTAGT    1035
1036    GGTAGATACTGAAGAAGCGGGTGAGTCTTTCCCAAACCAAAGCAA    1080
1081    TACGGGGTTTCCCATGGCATGACAAGCTGTCCCACCTCAGCATCC    1125
        ----,----+----,----+----,----+----,----+----,
1126    GTTGTTTTTCTCTTTCTTTTCCAGAAAAACCATCTGAAGAATTGG    1170
1171    ATTGAGAGATGAACTGCGCCTCACAGTAACCACAGGAGTTAAGCT    1215
1216    TCATAGATCAATGACTGCACAGCATACAAAAACCACGATACCTCA    1260
1261    AACAGAGCAAGGAAATCCACAGCGAGAACAAGAGGAGCCAGTGTT    1305
1306    TGTGTTGAGTGAGAACACTGCAGTTCTGTCAGCCAAAGCTGCCTG    1350
        ----,----+----,----+----,----+----,----+----,
1351    AGGGACCGCCAAACTGAGGGTGTGCGACCTCCAACTCAAAGCCAA    1395
1396    TTGGAAGAAAGAAACCATAGAAAGGAAGGAAAGGGGAGGAAGACA    1440
1441    GAGATCCTGGAAGAGATATGGGCATTTGGGGAAATAGTGTGACCA    1485
1486    TGTATCAGGCTGTGTGGACATCTAACGAATATGTCATGTTTTTGT    1530
1531    AAATACAAGCATGCACTCAGAAACAAAGGTAGAAAACTGCTTTGG    1575
        ----,----+----,----+----,----+----,----+----,
1576    GTGGTAACACTGTTCTCTGTCAAAATATAATAAAGAATACCTGCT    1620
1621    GATGGTAATGGATCATTGATTGTGAGCAGTTATTGGGGTTTGGTT    1665
1666    CCATGAAACAGGCTGAGTCTTCTTCCCAGAAACAAAGCAACGTGG    1710
1711    GCTCTATCGGATAACAAGCCGACCCTTCTCACCATGCACTGCTAT    1755
1756    TCCAGCACAACAAGGCTCTCTCCAGGAAGCTAAAAAGGGATAAAA    1800
        ----,----+----,----+----,----+----,----+----,
1801    TAAATTAATAGGAAAGAAATACACAAAAACAAGAAAATTTAAAAA    1845
1846    AGAATACTCCAAAAAATCTATAATTATTACAATAAAAACTTTAAA    1890
1891    AAAACACACCAACCTTCCACCCTGGGGGAGCACCAATGACAGCCT    1935
1936    TTTGTGCCCCATCGCGGTTTTATGAGAACAGCCACACACTTCAGA    1980
1981    GCTGACCCCGTGAGCCCCACAGTGGGGGGACCTCCCACAGTGGGT    2025
```

FIG. 20A

```
2026 GGACCTCCTCCACAACCACCCCCATCACTCACATTGAATGCCCAA 2070
2071 AGAAACAACAGCCCCAAAGGTTCCTCCTGGTGCTTCAGCCGCGTG 2115
2116 TGTTCCTCATTCTGCTGTGCTGATGGTGATCATTAACCCAACAGC 2160
2161 TCATTAACCAGGTTATGGCTCAGGTGCGTGCTGCTGAACAAGCTT 2205
2206 GGAGCCTAAAATGGTTCCTGCACACATCCCAGGGGACGGCCCTCC 2250

2251 ACCTTTCACTCCCCGCCATTACAGCTCTCCTTAATCAGAGGAATA 2295
2296 CAGATTCCATGCACTGAGTGCACTGAGCCATCGCCCACCTTCCCT 2340
2341 ACAAACACCTCCTGGTCCCCACAAACCCTCACTGTGGGAAGAGGG 2385
2386 GCTCTGGGGGGGTCACAGGGACAAACATTTAATAATTCCTGTATT 2430
2431 AATGGTTGATTAACTTAAAAATCTGTACTGATCAAATAAACTGCC 2475

2476 ACCCCTTGGGCATAGCTCAGAGCATGCTCATGGAGTACAGCCCAC 2520
2521 AGCTTTCCTCTGTGCTAGGGCAATGCTTCTCCTGGGTCCATGTTC 2565
2566 ATCCTGGGTGGATGCAGAGCCCCAGGGTGGTACATGAAACTGCAA 2610
2611 TGGGATGTCAGTGTTCAGAGTTCTCCAACCGTCTGCCCCATTGCC 2655
2656 AAAGGGGTAAAGTTCCTCGGAGCAGATTACCACACCCTGGAGCTG 2700

2701 GGCAAAGGTTGACGCTGGGCAAAGGTAGAAGCTGGGCATAGCTGC 2745
2746 ACGTTTCCTGCAGCTCAGGTGAGGGATTTCTGTCTCTGTGGGGCT 2790
2791 CCTTGTAGGGGAAATCCTTGGGGGGTCATCTGCTCTGCCTCACAG 2835
2836 CCTGTGAGGAGCACTGGCACTGCCCAAGGCAGTGGTGGCTGTGCT 2880
2881 CATGGAACTGATGTTTGAGTGACCCCATCCCCTCCTCTCCTGGTG 2925

2926 GCTGTAACCCTCTGGCCCCTCTCCTCCTACAGCTCCTTCCTGCAT 2970
2971 ATTCTTCCTCAACTTTTTCTAAATCTTCTTTCCAAATCTTCTACC 3015
3016 CCATCTGCTCCAGCACCTCCTTCTCCATCTCCTTCCCCAAACTCC 3060
3061 TCCTTATATCCCCTTCCCCAATCTCCTTCACCCACCTCCTTCTCC 3105
3106 TATCATCTTCTCTCATCTTTTACCATTTTCTACCCACCTTCTGCC 3150

3151 CCATCTCCTCCATCATATCCTTCTCAGTCTCCTTCCTCTCTCTCC 3195
3196 TTTCCCCAACTCCTTCCCCCCTCCTCTTCTCCAGCACAGATGGCC 3240
3241 TTCACATCGAGCTGCAACCACCCCAGTTTCACCCTCCCCTGGAGG 3285
3286 ACCCTCCTGCCTTATCTCGTGGCTCTGCACCACCTCCAGCCGGGA 3330
3331 TCAGGTAGGGGTCCTGTGGGGCTGCTGTGCCTGGCACACGTGTTG 3375

3376 CTATGGGGTGGGGGAGCCGCCATGGGGCAGGGAGGACACAAGTCC 3420
3421 AGCCCCCAGCCCCACTTGGGTTTCACTTTCACTTTGGTAATTCCA 3465
3466 TGATAGATGCCATTTTGGGTAGAATTTCTGTCTCTTCTTCACCTC 3510
3511 TGCCACACGGTGTGAGTGGGCTCCCACCCCCAGCAATCCTTCCCC 3555
3556 CTCTCTCCTGATCCCTCCCCACTGCTTTTACACCAGATGGAGCAC 3600

3601 ACACCAACTCACCCTGTGCCGCTCCATGCCCCACATTAACACAG 3645
3646 ACACCATCTCACCATCTCTCCGTGCCCTTCGCATTGCCCAGCCCA 3690
3691 GCTCAGGGTGGTGGCACCGAGCCTCCGTGTCACTGCCATTGTGGG 3735
3736 ACAGGACGTCGTCTGCGCTGTCACTTGTCTCCTTGCAAGAATGCT 3780
3781 TGGAATTCAGACATCAGATGGATCCAGCACCGTTCCTCTAGGATT 3825

3826 GTGCACCACTACCAAGACGGAGTGGACCTGGAGCAGATGGAGGAA 3870
3871 TATAAAGGGAGGACAGAACTGCTCAGGGATGGTCTCTCTGATGGA 3915
3916 AACCTGGATTTGCGCATCACTGCTGTGAGCACCTCTGATAGTGGC 3960
3961 TCATACAGCTGTGCTGTGCAGGATGATGATGGCTATGCAGAAGCT 4005
4006 TTGGTGGAGCTGGAGGTGTCAGGTCAGTGGCTGGGGTGACGTCTC 4050
```

FIG. 20B

```
      ----,----+----,----+----,----+----,----+----,
4051  CAGGTGTCCCTGGGTTTGTGGGTCCCACCCAACCTCTGTCCATCC  4095
4096  TCATCCTCACGTCCATGGATGGAGAGCTGAAGGACAGCAGCCTTT  4140
4141  GGAAGAGGTCAGGGCTGAATTGTTTTATGAGATGCTGGAATTAGA  4185
4186  GCGGACACACGGTGTGATTTGGGGAATAGACTGCATGGATGAGGT  4230
4231  GGTTGGGTTGGATTTCTGGGATGGGTTTCTCCATGTATCAGTGGC  4275
      ----,----+----,----+----,----+----,----+----,
4276  AGTGGGCACACGATGCTGAGCAGCTCCTCCGCCTGTGCCAATATG  4320
4321  GGGACGCTGCCATTGTGTGTCACTGTTCCCTGCTCACTGCTCCTT  4365
4366  CTGAACAGGTGAATTCCGTTACCTTTTCCTTGGGAACAGGACTAC  4410
4411  AAAAAAGGTCTAGGGAAAAGGGTCTAGCAGGTAGGGACCTTCCAC  4455
4456  CGAGACCGACACTAGCAGTGTTAAGACCAACCCAGTAGCCAGTAG  4500
      ----,----+----,----+----,----+----,----+----,
4501  TAACAAAAAGAGACATCTTTCTTTCCACTCAACTCGTACCTCCCC  4545
4546  TACCTCGTGTCCTTCCACAACACGTACCTGTCCTTACCAGCCCCA  4590
4591  CCACGACTCGAGTCCAGGTGTCTCCATGTGTCCTCCTGCTTCCCT  4635
4636  CTAAAAAGGACTCTAAGGGTCACGAGTAATTTATTGAAAAGGGAA  4680
4681  AGAAAAACCCTTACTTCCTTCCTTTTTTTCCCCACACCCACCCTT  4725
      ----,----+----,----+----,----+----,----+----,
4726  CTATCCTTACACCGACATCCGTCCACCTTTCA               4757
```

FIG. 20C

| | | | |
|---|---|---|---|
| bg14 (1816 bp) | vs | bg28 (523 bp) | 99.8% |
| | | bg32.1 (634 bp) | 94.6 |
| | | bg3 (1822 bp) | 97.2 |
| | | bg8 (3134 bp) | 93.5 |
| | | bg11 (1785 bp) | 90.3 |
| | | bg17 (1449 bp) | 77.6 |
| | | gi9 (2188 bp) | 88.8 |
| | | gi11 (1487 bp) | 78.6 |

FIG. 21

```
bg14          P  A  V  K  V  G  Q  Q  A  K  E  S  E  E  Q  K  S  E
              |  |  |  |  |  |  |  |  |  |  |  |  |  |  |  |  |  |
B-G Peptide 1 P  A  V  K  L  G  Q  Q  A  K  E  S (G) K  Q  K (S)(A)
              |  |  |  |  |  |  |  |  |  |  |  |  |  |  |  |  |  |
bg11          P  A  V  I  L  G  Q  Q  A  K  E  S  E  E  Q  K  S  E bg14          E  M  G  T  R  D  L  K  L  E  R  L  A  A  K  L  E
              |  |  |  |  |  |  |  |  |  |  |  |  |  |  |  |  |
B-G Peptide 2 N (S) G  V  A  D  L  K  E  L  A (S) E  L  Y  D  E
              |  |  |  |  |  |  |  |  |  |  |  |  |  |  |  |  |
bg11          G  S  G  V  A  D  L  K  L  A  A  K  L  E  Y  I  A
```

FIG. 22

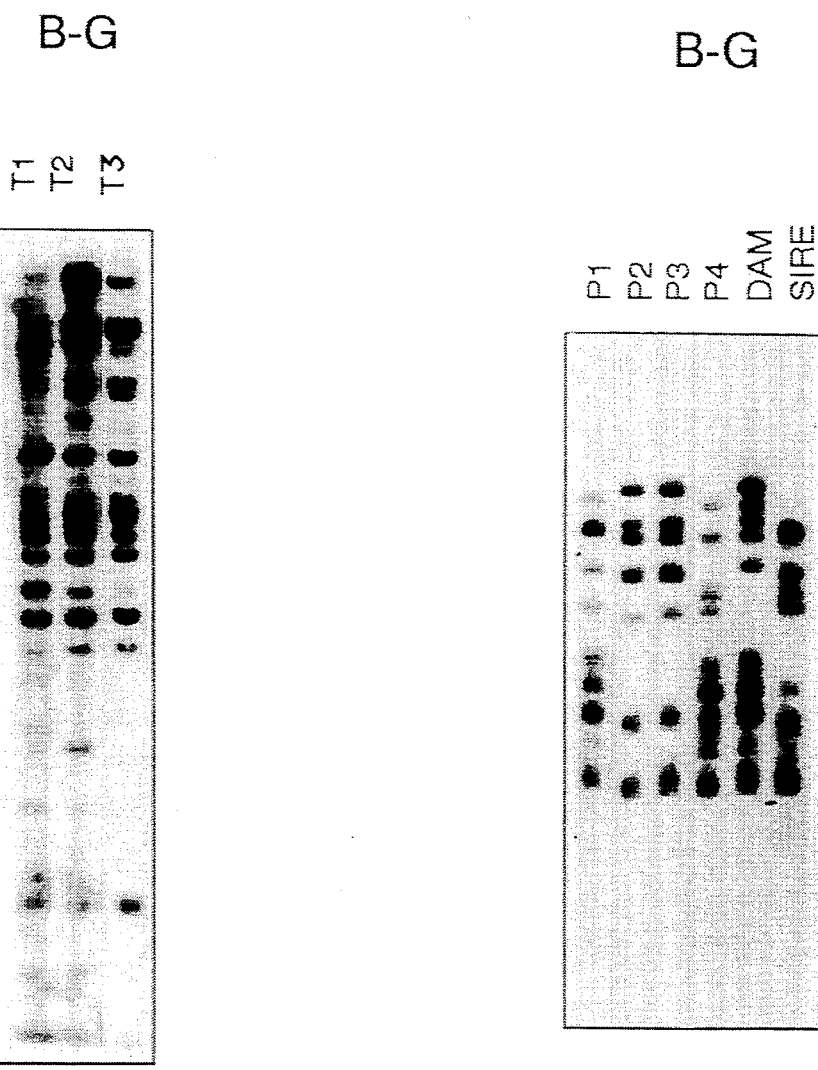
FIG.23 bg11 and Sst I
FIG.24 bg 32.1 and Pvu II

```
       ----,----+----,----+----,----+----,----+----,----+
   1 CTGGGTCAGATCTCCCGGCTTCATTTCTCTCCATCCCTGGGGTCCCCTCC   50
  51 TCCCGTCTGACTGCTGGAGGGCGGATGATCACCCCCTGTCTGCACCCCTC  100
 101 CCTGCGCTATCTGCAGCCCTTCAGATGCACCGCACCCCATTTGCACTCCC  150
 151 TGCCCCCCCTTTGTACACATGGGGGGGATATCAGCCCTCCTCCTTCCACC  200
 201 CACCCGTATCAGAGCCGCTGTGCTGCTGAGGGAGGCGGATGGGACGGCTG  250
       ----,----+----,----+----,----+----,----+----,----+
 251 CATCGCTCCCCCTCAGCTTCACAGAGCTGCTTTGCTGCGGGTTTTGGCTG  300
 301 CAATTCGGACCCTCTAAGAATGATCCCTCGTTGTGAGACTCCGCTGCAAA  350
 351 GCTGATCCGTTCGAGCTCTCCTCCTACAGCTGCTGCCCTCATATTCTCCC  400
 401 CACACTTCTTCCCCATATTCTTTCCAAATCCTCTTCCCCATCTCCTCCAC  450
 451 CGTCTCTTTCTCAGAGTCCTTCCTCTCTCCCTAAATTCTTCCCCCCTC   500
       ----,----+----,----+----,----+----,----+----,----+
 501 CTCTCCTCCAGCACAGATGCGCTTCACATCGGGATGCAACCACCCCAGTT  550
 551 TCACCCTCCCCTGGAGGACCCTCCTGCCTTATCTCGTGGCTCTGCACCTC  600
 601 CTCCAGCCGGGATCAGGTAGGGTCCTGTGGGCTGCTGTGCCTGGCACA    650
 651 GGTGTTGCTGTGGGTGGGGAGCAGCCATGGGGCAGGGAGGACCCATGT    700
 701 CCAGCACCCAGCCTCGCTTGGGTTTCTCTTTCACTTGGGCTATTTCATGA  750
       ----,----+----,----+----,----+----,----+----,----+
 751 AATGTGTGATTTCGGGTGGAATTTCTGTCCCTTCTTCACCTCCACCACAC  800
 801 GGTGTGAGTGGGCTCCCACCCCCAGCAATCCTTGCCCACTCCCTCCTGAT  850
 851 CCCTCCCCACTGCTTTTACATGGGATGGAGCACACACCAACTAACCCTGT  900
 901 GCCGCTCCATGCCCCCACATTAACACAGCCACCATCTCACCATCTCTTCG  950
 951 TGCCCTTCTCATTGCCCAGCCCAGCTCAGGGTGGTGGCGCCGAGCCTCCG 1000
       ----,----+----,----+----,----+----,----+----,----+
1001 TGTCACTGCCATCGTGGGACAGGATGTCGTGCTGCGCTGCCACTTGTGCC 1050
1051 CTTGCAAGGATGCTTGGAGATTGGACATCAGATGGATCCTGCAGCGGTCC 1100
1101 TCTGGTTTTGTGCACCACTATCAAAATGGAGTGGACCTGGGGCAGATGGA 1150
1151 GGAATATAAAGGGAGAACAGAACTGCTCAGGGATGGTCTCTATGATGGAA 1200
1201 ACCTGGATTTGCGCATCACTGCTGTGAGCACCTCCGATAGTGGCTCATAC 1250
       ----,----+----,----+----,----+----,----+----,----+
1251 AGCTGTGCTGTGCAGGATGGTGATGGCTATGCAGACGCTGTGGTGGACCT 1300
1301 GGAGGTGTCAGGTCAGTGGCTGGGGTGATGTCTCCAGGTGTCCCTGGGCT 1350
1351 TGTGTGTCCCCTACCGACCTCTGTCCATCCTCATCCTCACATCCTAGGAT 1400
1401 GGAGAACTGAAGGACAGCAGCCTTTGGAAGAGCTCAGGGCTGAACAGCTC 1450
1451 CATGAGATGCTGGAGTTGGATCGGGCACATGGTGTAATTTGAAAATGGAT 1500
       ----,----+----,----+----,----+----,----+----,----+
1501 ATGCATGGATGAGGTGGTTGGGTTGGGTTTCTGGGATGGGTTTCTCCACG 1550
1551 TCTCAGTGGCAGTGGGCACACGATGCTGAGCAGCTCCTCCGCCTGTGCCA 1600
1601 ATATGGGACGCTGCCATTGTGTGTCACTGCTCCCTGGTTGTTGTCCCTT  1650
1651 CGGGTTCTGTGATCTCCAGAAGTCGAAGTCGTGTTTGTCCACATAAGGCA 1700
1701 GTGGAAAAAGGAACCCTTGTCCTGATGTCTTTTCCAGATCCCTTTTCCCA 1750
       ----,----+----,----+----,----+----,----+----,----+
1751 GATCGTCCATCCCTGGAAGGTGGCTCTGGCTGTGGTCGTCACAATTCTCG 1800
1801 TTGGGTCATTTGTCATCAATGTTTTTCTCTGTAGGAAGAAAGGTGAGCTG 1850
1851 AGAGCGGAGGGGATGGAGCACAGGGAGGTGTTGTGCATGGACAGGGATGG 1900
1901 TCGGGGTGGTGCTGAGCTCTGGTGTACAGAGGTACACAGGAGGAGAAAGG 1950
1951 GAGATTTTCCTGACATTCCCACTGCCCATTAAATAACATTGCCTTTCTT  2000
       ----,----+----,----+----,----+----,----+----,----+
2001 TTGGGGAAATGAAGGAGGAAAAAAGAAGTGTGGGTGGGCAGATAGGAAA  2050
2051 GTGGGTGGACCGTGGGGCAGGTGGAAAGGTCCAGACCTCGGGACGTCCCC 2100
2101 AAACCAAGCTGCCCTGCTGACTACCTCTTCCTCCAATTTGTTTTCCAGCG 2150
2151 GCACAGAGCAGAGAGCTGAGTGAGTCCTTCCAGCCCCTTCCACCACCAAA 2200
```

FIG.25A

```
2201 GTCCCTTTAATGGAACTGATAGAAGACTGCAGAGTGCTGGGTTTATGCCT 2250
2251 TGTGCTGGGGCCATGGGATCTATGGACCTTGGGATGTGTTGGGGCCGTG 2300
2301 GGATGTGCTGGGGTCGTGGGATCTGTCAACCCTGATTGATCCACTTCAGA 2350
2351 ACTCTTGCCCAATCGGTTCCTTCCGATTCATTTAACTCCTTCTTGAGGCC 2400
2401 AAAGTGGTCATTGGCCACATCCCAGAAAAAAGGGTTTGGGGTCAGGGTGT 2450
2451 GGGAGCTGATCGCATGGAAACGTGTCCCCTCTGACCATGCATTTCATTTG 2500
2501 CTTCTATTTTGCAGAGAGAAAAGATGCAGCGTTGGGTAAGTCTCCTCCCC 2550
2551 ATATGTGAGGGAATTCAGGGTGTCCCCATGGCATCAGCAGTGGGATGAGC 2600
2601 AGCTGTCCGCTCTGACCATGCACTGCTCTGCTCTTTCTTTTCCAGCGGAA 2650
2651 CTAGATGAGATATCGGGTGAGTCTCCATTCCCAATTGTATTCTTTCAAAT 2700
2701 GTTCTGCCTTGGGGAGCTGTGGGATAGGATGTTCTTCTCACCATGCACTG 2750
2751 ATTCTACCTTTCCATTGCAGGTTTAAGTGCTGAAAATCTGAGTAAGTGTC 2800
2801 CCTCCTGACACTGAAGGAATTTGGGGTATTCCCATGGGATCAGCCATTGA 2850
2851 ATGAAAACATGGCCCCCTCTCTTCATGCATTTCCTATTTCTTACCTTTGC 2900
2901 AGAGCAATTAGCTTCAAAACTGAGTGAGTGCTCACTCCCAAACTCAAAGT 2950
2951 AAAGAGAGTCTGCCTGTGTGAGCTGTGGGATGAGATGTTCCACTCATCGT 3000
3001 GCATTGCTTTTCTCTTTATTTTCCAGACGAAAATGCTGACGAGTGGGTGA 3050
3051 GTCTACATTCACTAATGCAAAGAAATATGGGGTCTCCCAAGGGATGACAA 3100
3101 GCGTGTCCCGCATCATCATTTGGTGCTTCTTCTGTCTTTTTTTTTGCAGA 3150
3151 GGATTGCAATTCAGAGCTGAGTAAGTTGCAGTCACTGAACTGAGGGAATG 3200
3201 TGGGGTCTTCCCAAGGGACAGTGCATGGGATGAAAAATCCCCTCTGACCA 3250
3251 TGCACTGCTTTTCTCTTTCTTTCCCAGAGAAAGACTGTGAAGAGATGGGT 3300
3301 GAGTCCCCCCCCCCAAAATTAAACGTTGGGGTCCTCATGTGGAGCTGTGG 3350
3351 ATGAGATGTCCTCTCATCACGCACTGTTTCTACATTTCTTTGCAGGTTCT 3400
3401 GGCGTTGCAGATCTGAGTAAGTCTCCCCTACCAGCACGGAAGGAATTTGT 3450
3451 GGTCTTCCCATGGGATCAGCCATGGGACTGATCATCTGAGCCCTCTCATC 3500
3501 ATGCATTTCATATTCGTTCCTTTTGCAGAGGAACTGGCTGCAAAATTGGG 3550
3551 TGAGTGTTGCCTCCCAAATTAAATTAAAAAAGGGGTCTGCCTGGGCTCG 3600
3601 CTGTGGGATAGGATCTTCCTCTCACTGTGTGTTGCTTTTCCCTTTCTTTT 3650
3651 CCAGAGGAATATATTGCAGTGAATCGTGAGTCTCCCCTCCGAAATTATAA 3700
3701 ATGCTGGGGAAATCTTGTGTGCGATCGTGGGTAGAGCTCTTCCTCTCATC 3750
3751 ATGCACTGTTTCTGCTTTTCCTTTGCAGGGAGAAGGAATGTAAAGTTGAG 3800
3801 TGAGTCTCTCTTCCCAAACCAAACAGATTTGGGGTCTTCCCATGGGATCA 3850
3851 GCCATGGGATGATAATCTAACCCTACTCATCATGCATTTCTTATTGGTTC 3900
3901 CTTTGGCAGATAATATAGCTGCCAAACTGGGTGAGTCCCCCCTCACAGAT 3950
3951 TACATAAAAAATGGGGTCTGCCTGTGTGAGCTGTGGGATGAGATGTTCCT 4000
4001 CTCATCATGTACTACTTTTCTCTTCCTTTTCCAGCACAACAAACTAAAGA 4050
4051 ATTGGGTGAGTCTTCTTTCCCCAAACAAAGAAATACGGGATTCCCATGGG 4100
4101 ATGACAAGCTGTGCCACCTCATCATGCCCTGTTTTTTCTGTCCTTTTTGC 4150
4151 AGAGAAACAGCATTCACAGTTCCGTAAGTTGCAGTCACTAAACTGAAGGA 4200
4201 ATGTGGGGTCTTCCCAAAGTCCTGCATACGGGATGAAAAATCCCCTCTGA 4250
```

FIG. 25B

```
       ----,----+----,----+----,----+----,----+----,----+
4251 CCATGCACTGCTTTTCTCTTTCTATTCCAGACAGACACTTTCAGCGTATG 4300
4301 GGTGAGTCTCTCCCCCCCAAATTAAAAACGCTGGGGGCATCCTATGGGAG 4350
4351 CTGTGGGATGAGATTTTCCTCTCATCACACACTCCTTCTGCTTTTCCATT 4400
4401 GCAGATTTAAGTGCTGTAAACCAGAGTAAGTCTCCCTCCCTGCACAGAAG 4450
4451 GAACTTCCAGTTTTCCCATGGGATCAGCCATGGGATGATCATCCGACTCT 4500
       ----,----+----,----+----,----+----,----+----,----+
4501 TCTCATCATAAATTCGTCTTCTTCTTTGCAGAGAAACTGGTTACAAAACT 4550
4551 GGGTGAGTCCAACCTCCCAAACTAAATTAAAAGCAGTCAGACTTTGTGAG 4600
4601 CTGTGGGATGAGACGTTCTTCTCATCATGTGCTGCTTTCCTTTTACTTTT 4650
4651 CCAGAGGAACACTTTGAATGGATGGGTGAGTCTCCCCTCCCAAATTAAAA 4700
4701 ATGTTGGGGTCTTCCTGTGTGAGCTGTGGGATGAGCTGTTCCTCCCATCA 4750
       ----,----+----,----+----,----+----,----+----,----+
4751 TGCACTGGTTCTAATTTTCCTTTGCAGAGAGAAGGAATGTAAAGTTGGGT 4800
4801 GAGTCTTCTTCCCCAACCAAAGGGATTTGGGGTCTTCCATGGGATCAGCC 4850
4851 ATGGGATGATAACCTGAACCTTATCACATATTTCTTATTTGTTCTTTTTG 4900
4901 CAGAGATACCAGCTGTAATACTGGGTGAGTCCTCCCTCCCAAATTAAATA 4950
4951 CAAAAGGGGATCTGCCTGTGTGAGCTGTGGGATGAGATGTTCCTCTCATC 5000
       ----,----+----,----+----,----+----,----+----,----+
5001 ACGCATTATTTTCTCTTTCTTTTCCAGGGCAACAAGCTAAAGAATCAGGT 5050
5051 GAGTCTTCTTCCCTGTCCCAAAGGACTATGGGTTTCCCATGGGATGACAA 5100
5101 GCTGTGCCACCTCCTCACGAGGTGCTTCTTCTTTCTTTTTGCAGAGAAA 5150
5151 CAGAAATCGGAGCTGAGTAAGTTGCAGTCACTGAACTGAGGGAATGTGGG 5200
5201 GTCTTCCCAAAGTCTTGTGTATGGGATGAAAAATCCCCTCTGACCATGCA 5250
       ----,----+----,----+----,----+----,----+----,----+
5251 CTGCTTTTCTCCTCCTTTGCCAGAGGAGCGCCATGAGGAGATGGGTGAGT 5300
5301 CTCCCCTCCCATATTAAAATCGTTGGGGTCTTCCTGTGTGAGCTGTGAGA 5350
5351 TGAGATGTTCCTCTCATCATGCGATGCTTTTCTCTCTTTTCCAGCAGAAC 5400
5401 AAACTGAAGCAGTGGGTGAGTCTTTGTCCCCAACCCAAAGGAATATGGGG 5450
5451 CAATCCATGGGATGACAAGCTGTCCCATCTCATCGTGCATTGCTTTCCTA 5500
       ----,----+----,----+----,----+----,----+----,----+
5501 TTCCTTTTTTCTAGTGGTAGATACTGAAGAAGCGGGTGAGTCTTTCCCAA 5550
5551 ACCAAAGCAATACGGGGTTTCCCATGGCATGACAAGCTGTCCCACCTCAG 5600
5601 CATCCGTTGTTTTCTCTTTCTTTTCCAGAAAAACCATCTGAAGAATTGG 5650
5651 ATTGAGAGATGAACTGCGCCTCACAGTAACCACAGGAGTTAAGCTTCATA 5700
5701 GATCAATGACTGCACAGCATACAAAAACCACGATACCTCAAACAGAGCAA 5750
       ----,----+----,----+----,----+----,----+----,----+
5751 GGAAATCCACAGCGAGAACAAGAGGAGCCAGTGTTTGTGTTGAGTGAGAA 5800
5801 CACTGCAGTTCTGTCAGCCAAAGCTGCCTGAGGGACCGCCAAACTGAGGG 5850
5851 TGTGCGACCTCCAACTCAAAGCCAATTGGAAGAAAGAAACCATAGAAAGG 5900
5901 AAGGAAAGGGGAGGAAGACAGAGATCCTGGAAGAGATATGGGCATTTGGG 5950
5951 GAAATAGTGTGACCATGTATCAGGCTGTGTGGACATCTAACGAATATGTC 6000
       ----,----+----,----+----,----+----,----+----,----+
6001 ATGTTTTTGTAAATACAAGCATGCACTCAGAAACAAAGGTAGAAAACTGC 6050
6051 TTTGGGTGGTAACACTGTTCTCTGTCAAAATATAATAAAGAATACCTGCT 6100
6101 GATGGTAATGGATCATTGATTGTGAGCAGTTATTGGGGTTTGGTTCCATG 6150
6151 AAACAGGCTGAGTCTTCTTCCCAGAAACAAAGCAACGTGGGCTCTATCGG 6200
6201 ATAACAAGCCGACCCTTCTCACCATGCACTGCTATTCCAGCACAACAAGG 6250
```

FIG.25C

```
       ----,----+----,----+----,----+----,----+----,----+
6251 CTCTCTCCAGGAAGCTAAAAAGGGATAAAATAAATTAATAGGAAAGAAAT 6300
6301 ACACAAAAACAAGAAAATTTAAAAAAGAATACTCCAAAAAATCTATAATT 6350
6351 ATTACAATAAAAACTTTAAAAAAACACACCAACCTTCCACCCTGGGGGAG 6400
6401 CACCAATGACAGCCTTTTGTGCCCCATCGCGGTTTTATGAGAACAGCCAC 6450
6451 ACACTTCAGAGCTGACCCCGTGAGCCCCACAGTGGGGGACCTCCCACAG 6500
       ----,----+----,----+----,----+----,----+----,----+
6501 TGGGTGGACCTCCTCCACAACCACCCCATCACTCACATTGAATGCCCAA 6550
6551 AGAAACAACAGCCCCAAAGGTTCCTCCTGGTGCTTCAGCCGCGTGTGTTC 6600
6601 CTCATTCTGCTGTGCTGATGGTGATCATTAACCCAACAGCTCATTAACCA 6650
6651 GGTTATGGCTCAGGTGCGTGCTGCTGAACAAGCTTGGAGCCTAAAATGGT 6700
6701 TCCTGCACACATCCCAGGGGACGGCCCTCCACCTTTCACTCCCCGCCATT 6750
       ----,----+----,----+----,----+----,----+----,----+
6751 ACAGCTCTCCTTAATCAGAGGAATACAGATTCCATGCACTGAGTGCACTG 6800
6801 AGCCATCGCCCACCTTCCCTACAAACACCTCCTGGTCCCCACAAACCCTC 6850
6851 ACTGTGGGAAGAGGGGCTCTGGGGGGGTCACAGGGACAAACATTTAATAA 6900
6901 TTCCTGTATTAATGGTTGATTAACTTAAAAATCTGTACTGATCAAATAAA 6950
6951 CTGCCACCCCTTGGGCATAGCTCAGAGCATGCTCATGGAGTACAGCCCAC 7000
       ----,----+----,----+----,----+----,----+----,----+
7001 AGCTTTCCTCTGTGCTAGGGCAATGCTTCTCCTGGGTCCATGTTCATCCT 7050
7051 GGGTGGATGCAGAGCCCCAGGGTGGTACATGAAACTGCAATGGGATGTCA 7100
7101 GTGTTCAGAGTTCTCCAACCGTCTGCCCCATTGCCAAAGGGGTAAAGTTC 7150
7151 CTCGGAGCAGATTACCACACCCTGGAGCTGGGCAAAGGTTGACGCTGGGC 7200
7201 AAAGGTAGAAGCTGGGCATAGCTGCACGTTTCCTGCAGCTCAGGTGAGGG 7250
       ----,----+----,----+----,----+----,----+----,----+
7251 ATTTCTGTCTCTGTGGGCTCCTTGTAGGGGAAATCCTTGGGGGGTCATC 7300
7301 TGCTCTGCCTCACAGCCTGTGAGGAGCACTGGCACTGCCCAAGGCAGTGG 7350
``` end of C:\DNADATA\MILLER\G-114FIN.SEQ(LEND,REND)

FIG.25D

RESTRICTION FRAGMENT LENGTH POLYMORPHISM TEST FOR HAPLOTYPING DOMESTICATED FOWL

This application is a continuation of Ser. No. 07/688,326 filed Apr. 22, 1991 (abandoned) which is a continuation-in-part of Ser. No. 588,922 filed Sep. 27, 1990, which is a continuation-in-part of Ser. No. 210,405 filed Jun. 23, 1988 (abandoned) which is a continuation-in-part of Ser. No. 130,529 filed Dec. 9, 1987 (abandoned) which is a continuation-in-part of Ser. No. 068,176 filed Jun. 30, 1987 (abandoned). This application is also a continuation-in-part of Ser. No. 413,301 filed Sep. 28, 1989 (abandoned).

Each of applications Ser. Nos. 210,405 (abandoned); 130,529 (abandoned); 413,301 (abandoned); and 588,922 is incorporated herein by reference.

FIELD OF THE INVENTION

This invention relates to restriction fragment length polymorphism pattern tests useful to genotype domesticated fowl for the major histocompatibility B-G loci. The invention also relates to the use of certain B-G polypeptides to impart immunity to or to control the susceptibility of domesticated fowl to various diseases.

BACKGROUND OF THE INVENTION

In domesticated fowl the major histocompatibility complex (MHC) which is associated with the regulation of immune recognition and immune response is called the B system. Resistance to Marek's disease is closely related to the domesticated fowl MHC. Resistance to other diseases, general fitness, and productivity also appear to be influenced to some extent by MHC haplotype.

MHC haplotyping of chickens is presently done by hemagglutination assay which relies on the production of specific antisera. The assay in itself is technically simple. However, the production of the antisera and the interpretation of the assays require a highly trained individual. The MHC haplotypes present in commercial strains of chickens are usually a trade secret known only to individual breeders. Isolation of cloned gene sequences from the B system provides a means of developing alternative methods for MHC haplotyping of birds and for determining the genotype at particular loci within the B system. The interpretation of results is generally simpler and more uniform since typing by restriction fragment length polymorphism patterns is no longer dependent upon alloantisera which often require selective absorptions with blood samples from genetically-defined animals to delineate haplotype specificity.

SUMMARY OF THE INVENTION

The B system of histocompatibility in domesticated fowl is known to contain three subregions which are identified as B-F, B-G and B-L. B-F, B-G and B-L are described as subregions because multiple genes of each type are present within the region of the B system. This invention includes cDNA clones encoding B-G antigens of the B system. MHC haplotyping is accomplished by use of novel probes provided by these clones to detect restriction fragment length polymorphism (RFLP) patterns typical for various B-G alleles present at the multiple loci within the B-G subregion.

Genetic recombination within the B system of the chicken is rare. For that reason, while the probes of this invention screen for the B-G genes, additional genes also of importance to disease resistance may be located in regions within and closely adjacent to the B system and genetically and physically linked to the B-G type. Other genes of mostly unknown function are located within the MHC as well.

DESCRIPTION OF THE FIGURES

FIG 1A is a Coomassie-blue stained SDS-8% polyacrylamide gel containing the following protein samples: 1 μg purified B-G21 antigen (lane 1); 40 μg of total cell protein from a λbg28 lysogen grown in the presence of IPTG (lane 2); 40 μg of total cell protein from a λgt11 lysogen grown in the presence of IPTG (lane 3); 40 μg of total cell protein from λbg28 lysogen grown in the absence of IPTG (lane 4); and protein size markers (marked MK) with their respective molecular weights given to the left in kilodaltons (kDa).

FIG. 1B is a parallel immunoblot. The same protein samples were subjected to SDS-polyacrylamide gel electrophoresis as in FIG. 1A and then were electrophoretically transferred to a hybridization membrane. The proteins were reacted with B-G antigen-directed antiserum that had been affinity purified against bg28-β-galactosidase fusion protein. Bound antibodies were detected with $^{125}$I-Protein A and the above autoradiogram was the result of an overnight exposure with an intensifying screen at −70° C. The white arrowheads mark the position of the bg28-β-galactosidase fusion protein. The dark arrowheads mark the positions of the two polypeptides of B-G21 antigen.

FIG. 2A is an autoradiogram which was the result of a 16-hour exposure. FIG. 2B is an autoradiogram which was the result of a 1-hour exposure.

Figure 2A:
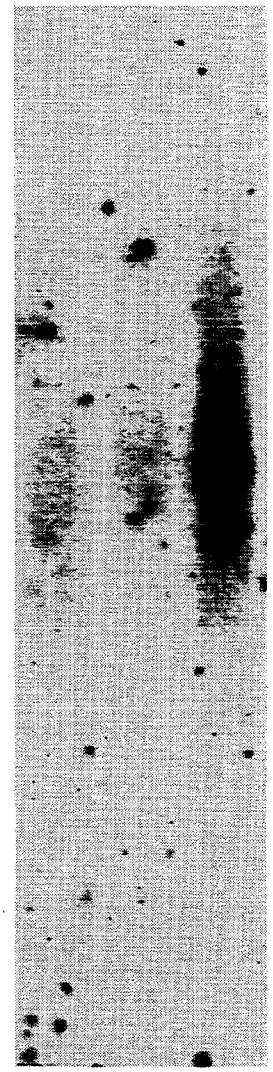
FIGS. 2A and 2B are Northern analyses of poly(A)+ RNA from embryonic tissues. Poly(A)+ RNA samples (1 μg each) from the brain (BR), gizzard (GI), and erythrocytes B (ER) were subjected to formaldehyde agarose gel electrophoresis, transferred to a hybridization membrane, and hybridized with either $^{32}$P-labeled bg28 insert (A) or a $^{32}$P-labeled β-actin probe (B).
Figure 2B:
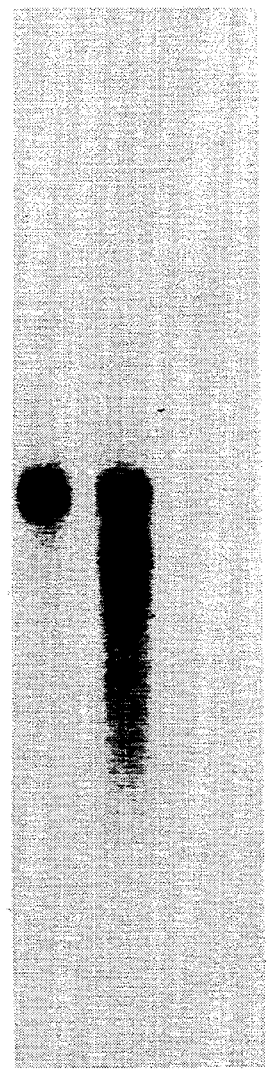

The 16 hour exposure of FIG. 2B revealed an actin mRNA species in the erythrocyte RNA sample (data not shown).

Figure 3:
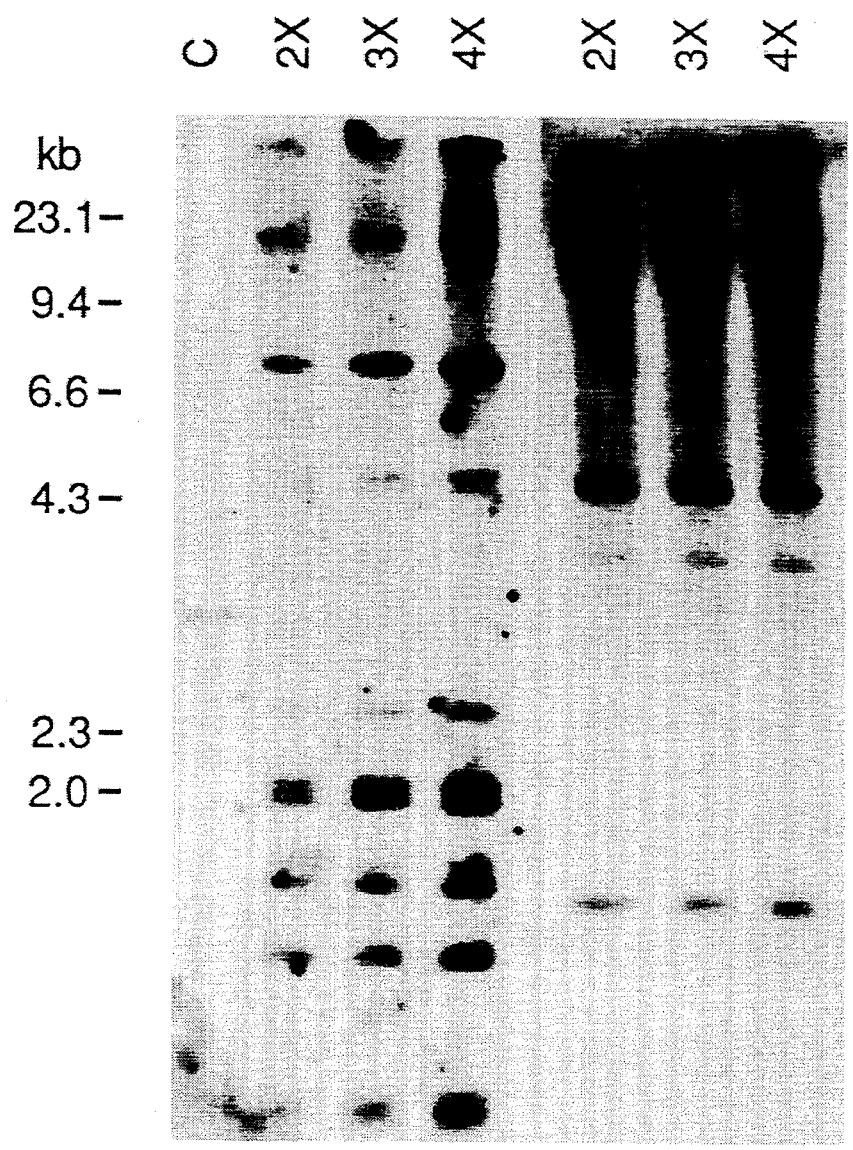

FIG. 3. Southern analyses of chicken genomic DNA from birds disomic, trisomic, or tetrasomic for the B system-bearing microchromosome. PvuII-digested genomic DNA (5 μg each) from chickens either disomic (2×), trisomic (3×), or tetrasomic (4×) for the B-complex microchromosome were subjected to electrophoresis on an 0.8% agarose gel and hybridized within the gel to either $^{32}$P-labeled λbg28 insert (left 4 samples) or a $^{32}$P-labeled β-actin probe (right 3 samples). The lane marked C contained 10 pg of HindIII-linearized Bluescript plasmid containing the bg28 insert. On the left are molecular size markers (in kilobase pairs) based on a HindIII digest of phage λ. The above autoradiograms were the result of an overnight exposure.

Figure 4:
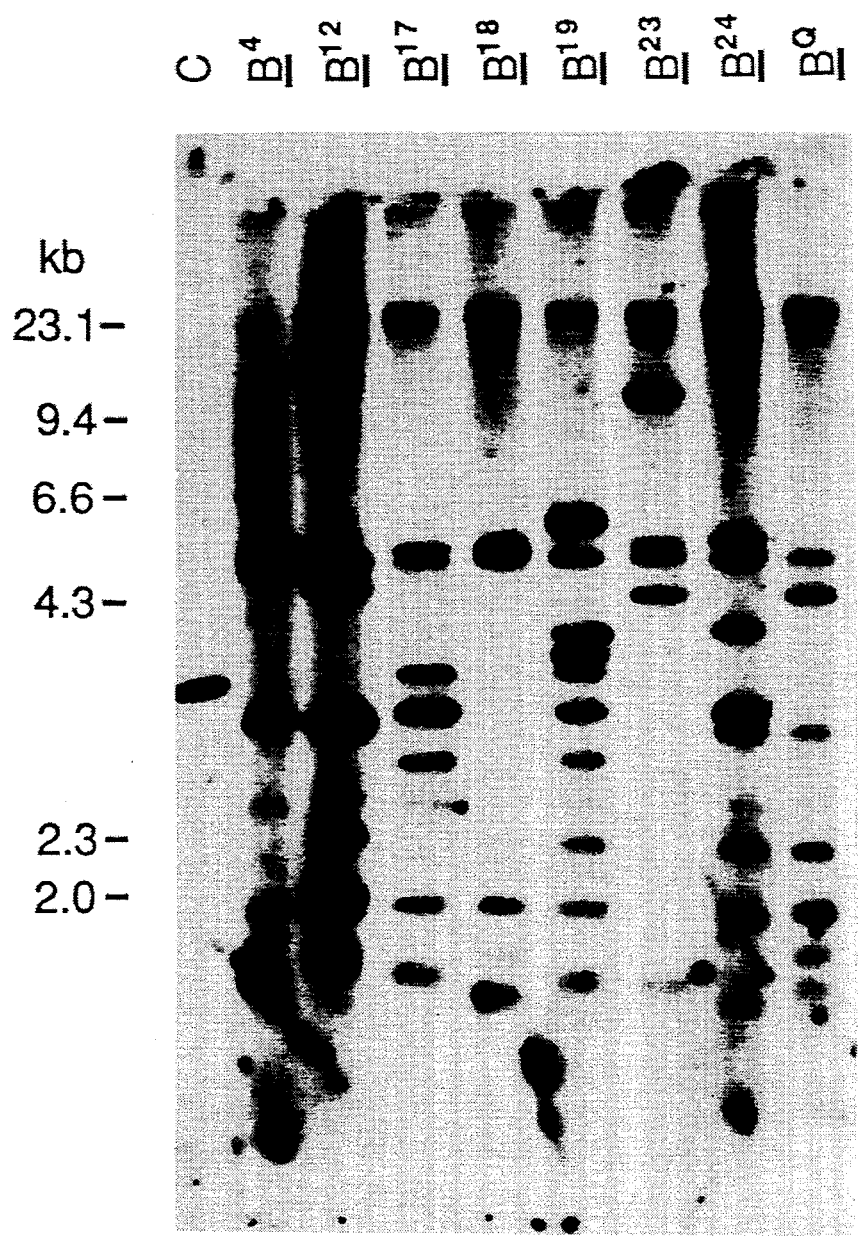

FIG. 4. Hybridization of the bg28 insert to restriction digests of chicken genomic DNA from birds of different B haplotypes. PvuII-digested genomic DNA (5 μg each) from chickens of different B haplotypes were subjected to electrophoresis on an 0.8% agarose gel and hybridized within the gel to $^{32}$P-labeled bg28 insert. DNA samples are labeled according to their respective B haplotype (see Table 1). The lane marked C contained 10 pg of HindIII-linearized Bluescript plasmid containing the bg28 insert. On the left are molecular size markers (in kilobase pairs) based on a HindIII digest of phage λ. The above autoradiogram was the result of an overnight exposure.

Figure 5:
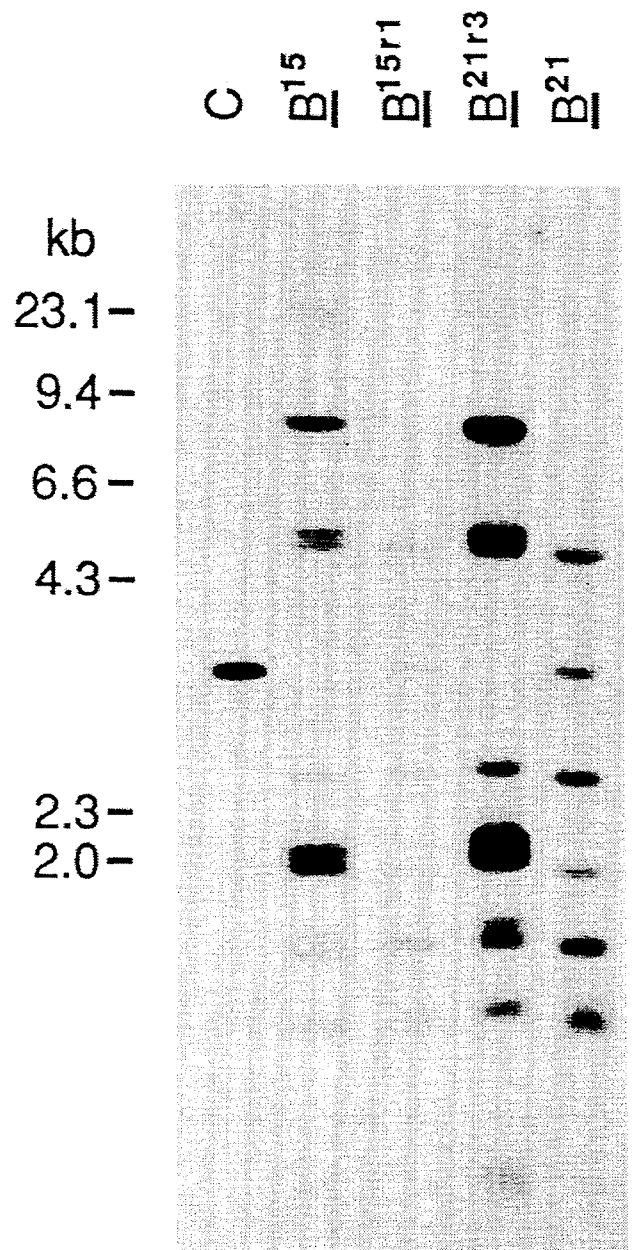

FIG. 5. Hybridization of the bg28 insert to restriction digests of chicken genomic DNA from birds of B-region recombinant haplotype. PvuII-digested genomic DNA (5 μg each) from chickens of either the parental $B^{15}$ and $B^{21}$ haplotypes or the recombinant $B^{15r1}$ and $B^{21r3}$ haplotypes were subjected to electrophoresis on an 0.8% agarose gel and hybridized within the gel to 32P-labeled bg28 insert. DNA samples are labeled according to their respective haplotype (see Table 1). The lane marked C contained 10 pg of HindIII-linearized Bluescript plasmid containing the bg28 insert. On the left are molecular size markers (in kilobase pairs) based on a HindIII digest of phage λ. The above autoradiogram was the result of an overnight exposure.

FIG. 6 (SEQ. ID. NO. 1) Partial nucleotide sequence of the bg28 insert and the corresponding amino-acid sequence, determined by the dideoxy-chain-termination method of nucleotide sequencing on one strand only of bg28 cloned cDNA.

FIG. 7 (SEQ. ID. NO. 2) Nucleotide sequence of the bg28 insert, determined by the dideoxy-chain-termination method of nucleotide sequencing of both strands of bg28 cloned cDNA.

Figure 8:
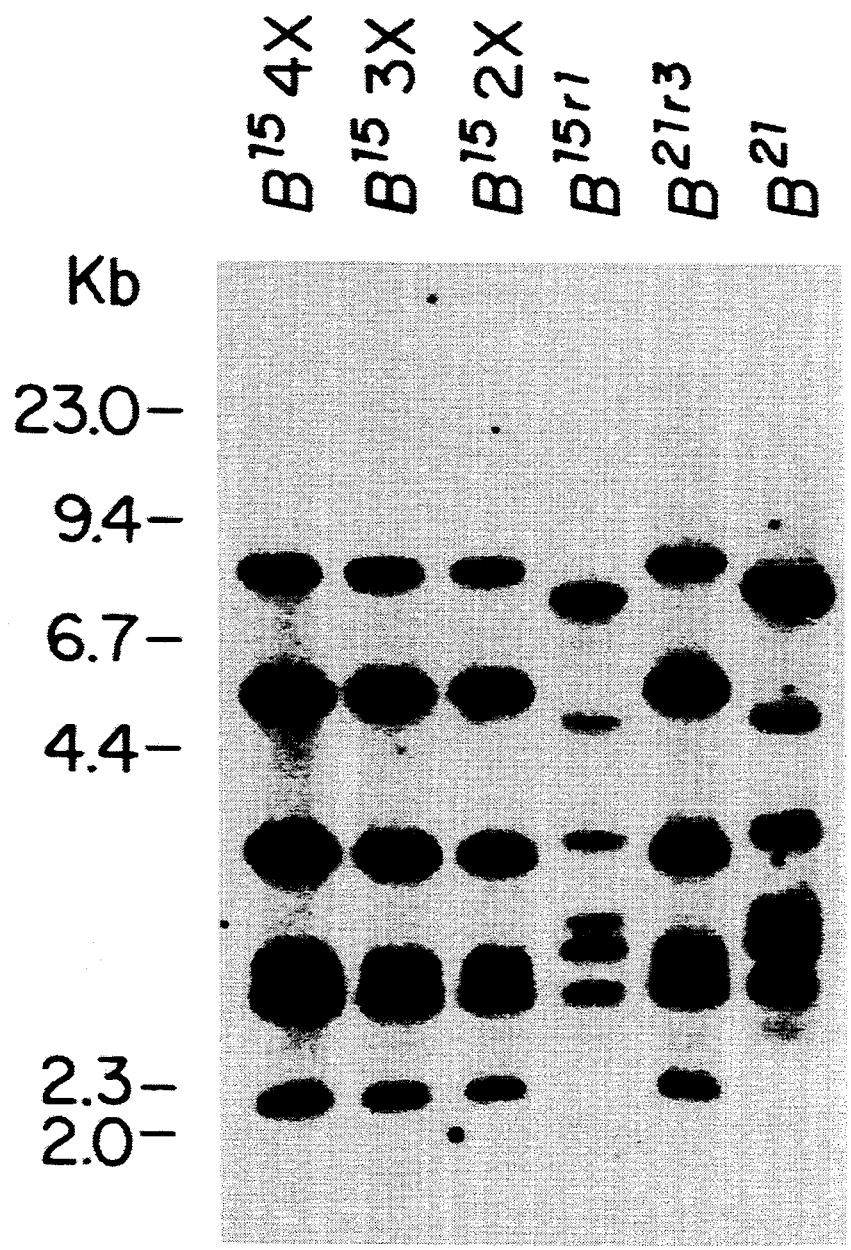

FIG. 8. Southern blot analyses of hybridization between bg32.1 and chicken genomic DNA. DNA samples are from birds of $B^{15}$ haplotype disomic (2×), trisomic (3×) and tetrasomic (4×) for the B system-bearing microchromosome and from birds of $B^{15r1}$, $B^{21r3}$, and $B^{21}$ haplotypes. Pvu II-digested genomic DNA samples (5 μg each) were subjected to electrophoresis in an 0.8% agarose gel and hybridized within the gel to 32P-labeled bg32.1 insert. On the left are molecular size markers (in kilobase pairs) based on a Hind III digestion of phage λ. The autoradiogram is the result of an overnight exposure.

Figure 9A:
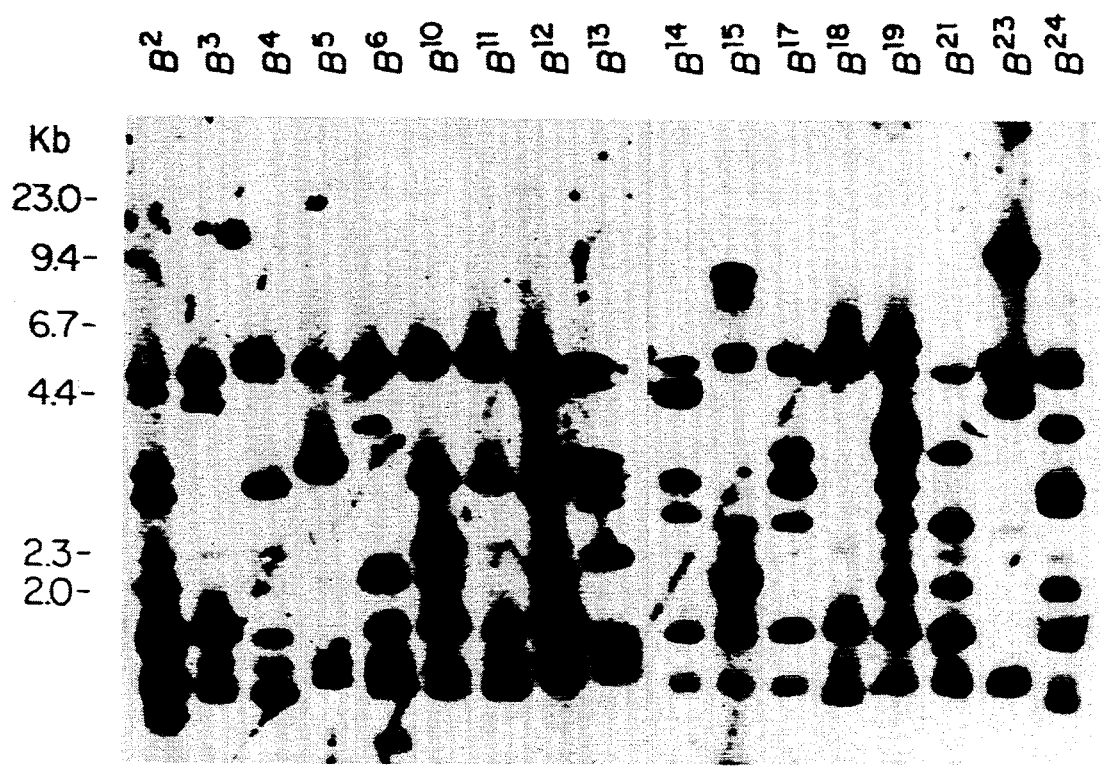
Figure 9B:
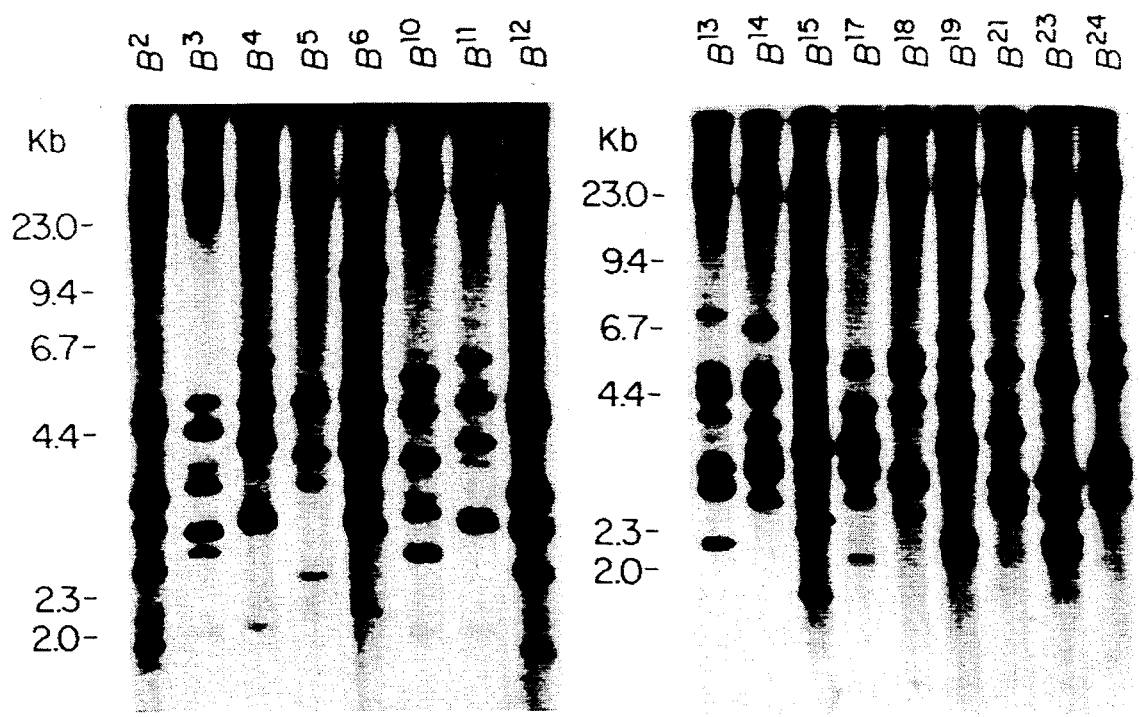

FIGS. 9A and 9B. Hybridization of the bg28 (A) and bg32.1 (B) probes to restriction digests of chicken genomic DNA from birds of 17 standard haplotypes. Pvu II-digested genomic DNA (5 μg each sample) were subjected to electrophoresis in an 0.8% agarose gel and hybridized within the gel to the 32P-labeled probes. DNA samples are labeled according to their respective B haplotype (see Table 3). Molecular size markers (in kilobase pairs) are based on a Hind III digestion of phage λ. The autoradiograms are the result of overnight exposures.

Figure 10:
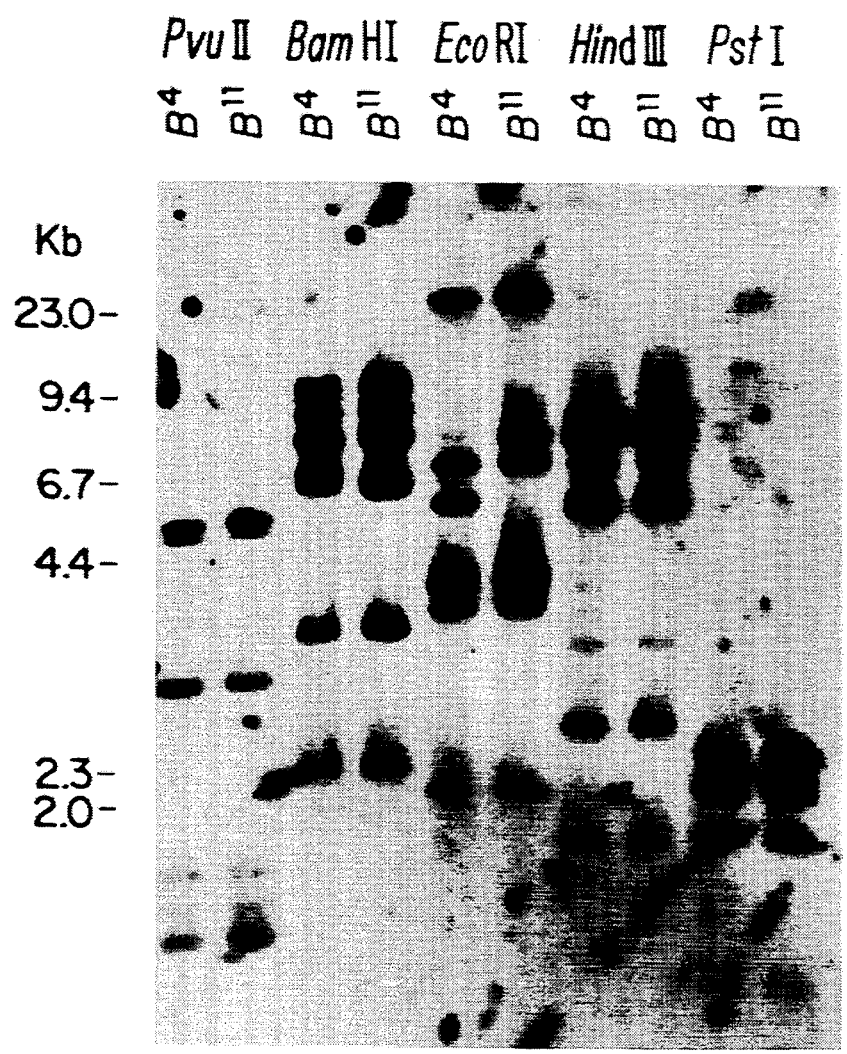

FIG. 10. Hybridization of the bg28 probe to genomic DNA (5 μg each lane) from birds of $B^4$ and $B^{11}$ haplotypes digested with Pvu II, Bam HI, Eco RI, Hind III and Pst I. On the left are molecular size markers (in kilobase pairs) based on a Hind II digestion of phage λ. The autoradiogram is the result of an overnight exposure.

FIG. 11. (SEQ. ID. NO. 3) Nucleotide sequence of bg32.1.

FIG. 12. (SEQ. ID. NO. 4) Nucleotide sequence of bg11.

FIG. 13. (SEQ. ID. NO. 5) Nucleotide sequence of bg14.

FIG. 14. (SEQ. ID. NO. 6) Nucleotide sequence of bg3.

FIG. 15. (SEQ. ID. NO. 7) Nucleotide sequence of bg8.

FIG. 16. (SEQ. ID. NO. 8) Nucleotide sequence of bg17.

FIG. 17. (SEQ. ID. NO. 9) Nucleotide sequence of gi6.

FIG. 18. (SEQ. ID. NO. 10) Nucleotide sequence of gi9.

FIG. 19. (SEQ. ID. NO. 11) Nucleotide sequence of gi11.

FIG. 20. (SEQ. ID. NO. 12) Nucleotide sequence of a 4.757 Kb fragment of chicken genomic DNA to which all the cDNA clones will hybridize under stringent conditions (in overnight aqueous solution hybridizations at 65° C. in 5× SSPE, 5× Denhardt's, 1% SDS, 100 ug/ml salmon sperm DNA, 32P-labeled denatured probe, followed by a 65° C. stringent wash in 0.5× SSC).

FIG. 21. Percent similarity among the bg cDNA clone sequences as exemplified by comparison of all clones to bg14 using the ALIGN program in the DNA-STAR.

FIG. 22 (SEQ. ID. NO. 13) Comparison of the peptide sequence of two B-G 21 peptides with the predicted amino acid sequences of bg14 and bg11 cDNA clones.

FIG. 23. Hybridization of the bg11 probe to restriction digests of turkey genomic DNA from three inbred lines. Sst 1-digested DNA samples (10 ug each sample) were subjected to electrophoresis in an 0.8% agarose gel, alkaline transferred by positive pressure displacement into a hybridization membrane (NEN Gene Screen), baked for 1 hour at 80° C., briefly UV crosslinked. Hybridization was carried out at 60° C. in aqueous solution overnight (5× SSPE, 5× Denhardt's, 1% SDS, 100 ug/ml salmon sperm DNA, 32P-labeled denatured probe). Wash conditions were as follows: (a) a room temperature wash for 5 min. in 2× SSC (sodium chloride/sodium citrate), (b) followed by 60° C. stringent temperature wash for 30 min. in 0.5× SSC+1% SDS (sodium dodecyl sulfate) and (c) a second room temperature wash for 5 min. in 2× SSC to remove the SDS before an overnight exposure of film to the membrane.

FIG. 24. Hybridization of the bg32.1 probe to restriction digests of pheasant DNA samples (10 ug each digested with Pvu II) from a family of pheasants (dam, sire and four progeny) in which B haplotypes have been defined by serological methods. Conditions of hybridization and washing are identical to those provided in FIG. 22 (SEQ. ID. NO. 13).

FIG. 25 (SEQ. ID. NO. 14). Sequence of a complete B-G gene. Included is a portion of the DNA upstream from the transcription start site.

DETAILED DESCRIPTION OF THE INVENTION

Pursuant to this invention, probes are provided by cloning of cDNA fragments from genes found within the B-G subregion of the MHC of a domesticated fowl, e.g., a chicken. With these probes, the presence of multiple alleles within the B-G subregion, a subregion of the B region encompassing multiple B-G loci, is demonstrated through homologous DNA hybridization of the B-G gene sequences in genomic DNA cut with a restriction enzyme, electrophoresed and analyzed in a Southern hybridization carried out either directly in the agarose matrix of the electrophoretic gel or in hybridization-membranes into which the DNA has been transferred. RFLP patterns which appear to be typical for each of a plurality of B-G alleles are described. Probes subsumed by the invention including synthetic oligonucleotide probes synthesized based on the sequences of the B-G cDNA clones described herein provide a new means of haplotyping chickens and other domesticated fowl including poultry (principally in the Order Galliformes) and game birds (principally in the Orders Anseriformes and Galliformes).

In one embodiment of the invention, a cDNA clone bg28 for a B-G antigen of the chicken major histocompatibility complex (MHC) was isolated by screening of a lambda gt11 cDNA library constructed from chicken embryo erythroid cell poly(A+) RNA. The identity of the cDNA clone as one encoding a B-G antigen was confirmed (1) by demonstrating that the clone is complementary to an erythroid cell-specific messenger RNA, (2) by obtaining the predicted patterns of hybridization of the clone with restriction endonuclease digested genomic DNA from inbred, MHC recombinant and polysomic chicken lines, and (3) by demonstrating the specific reactivity of antibodies monospecific for the fusion protein of this clone with B-G antigen protein.

Screening of the lambda gt11 cDNA library. A previously described lambda gt11 library, 1/ the M library prepared from gradient-fractionated poly (A)+ erythroid cell RNA was screened essentially as described previously. 2/ Overnight cultures of *E. coli* strain Y1088 3/ were infected with 50,000 plaque-forming units of recombinant lambda gt11, suspended in top agarose, and plated on 150 mm TYE-plates. Two plates were prepared for each of five aliquots of the amplified M library. The rabbit antiserum prepared against purified B-G21 was preabsorbed by the addition of 4 mg/ml ovalbumin, and by mixing 250 μl of the antiserum with Y1088 cells from a 10 ml overnight culture, spun down and resuspended in 10 ml of G buffer (TBS containing 0.1% gelatin). After 30 minutes incubation on ice, the cells were spun out and the antibody containing solution was then poured onto the surface of a 150 mm plate containing confluently lysed Y1088 cells infected with wild type lambda gt11. After an additional 30 minutes incubation on this plate (with rocking), the antibody containing solution was collected and the debris removed by centrifugation. It was then diluted to a final volume of 125 ml with GT and added to the filters. The additional steps in screening are as previously described (Moon, et al., 1985). Approximately 100 plaques were found to react positively with the rabbit anti-β-G21 serum. Thirty of these were picked for a second screening, the majority of which were again positive on the second screening. From these, six clones of varying intensity of reactivity with the antiserum were picked for further study. Three of these were subcloned.
1/ See Moon, et al., *J.Cell Biol.* 100:152-160 (1985).
2/ See Young, et al., *Proc.Nat.Acad.Sci.* 80:1194-1198 (1983).
3/ See Young, et al., *Science* 222:778-782 (1983).

Subcloning lambda gt11 inserts into M13 and Bluescript. cDNA inserts were obtained from recombinant clones of lambda gt11 by digestion with EcoR1. Insertion into the M13 and Bluescript (Stratagene) vectors was carried out by mixing the digested recombinant clones with the new vector in a ratio of 3:1 and religating. Recombinant colonies were selected using X-gal plates. The subclone with the longest insert 0.5 kb in size, designated bg28, was selected for further analysis.

Figures 1A, 1B:
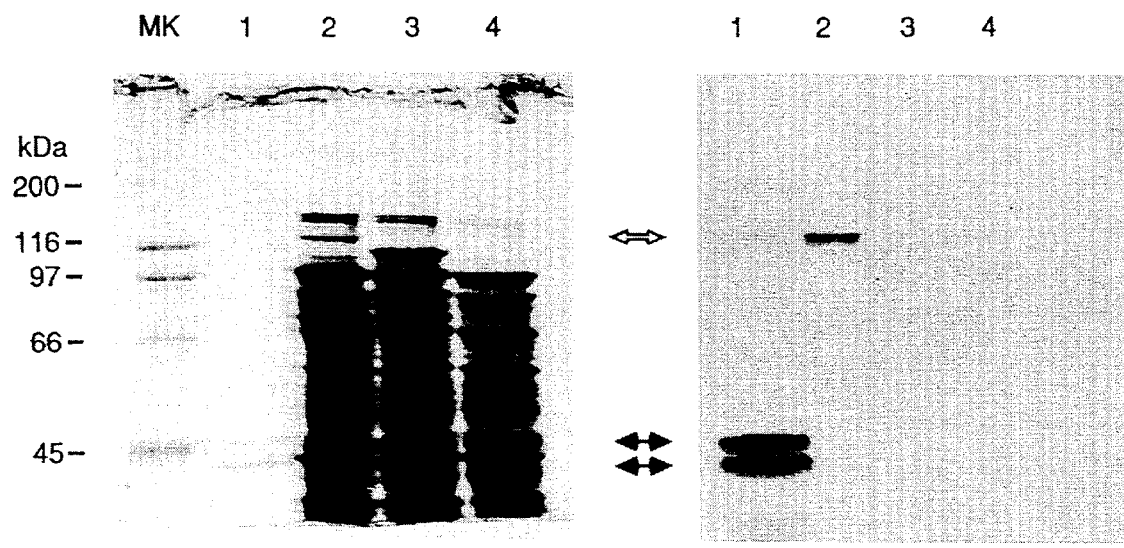
FIGS. 1A and 1B are immunblots of B-G21 antigen and λbg28 lysogen proteins reacted with antibodies specific to the bg28-β-galactosidase fusion protein.

Antiserum 7 used in identifying those clones was prepared against purified B-G21 antigen and was demonstrated to be specific for B-G antigens and for bg28 fusion protein in Western blot preparations. The presence of antibodies within this antiserum which recognize epitopes shared by the fusion protein product and B-G21 protein was also demonstrated. Antibodies affinity-purified with the bg28 lysogen lysate were found to bind to B-G21 antigen in immunoblots. See FIG. 1.

Preparation of fusion protein B-G28. *E. coli* strain Y1089 (supF) 4/ were infected with the lambda gt11 recombinant clones, colonies replica plated and lysogens selected as previously described. 5/ One lysogen, grown up in an overnight culture, was inoculated into 25 ml TYE media and incubated at 32° C. to an OD$_{600}$ of 0.6. The cells were then heat shocked at 42° C. for 20 minutes, IPTG added to a final concentration of 10 mM, and incubation continued at 37° C. for two hours. Parallel cultures of the lambda gt11 wild type and an uninduced culture of the lysogen were prepared to serve as controls. The cultures were harvested by pelleting the cells, resuspending in PBS and 0.1% phenyl methyl sulfonyl fluoride (PMSF). The cells were lysed by sonication, the cellular debris removed by centrifugation, and the resulting supernatants were used as a source of the bg28 fusion protein.
4/ See Young, et al., *Science* 222:778-782 (1983).
5/ See Cox et al., *J.Cell Biol.* 100:1548-1557 (1985).

Hybridization of bg28 cDNA insert to transcripts from erythroid and nonerythroid cells. Poly(A)+ RNA was isolated from different tissues of 14-day chick embryos. The RNA samples were subjected to denaturing agarose gel electrophoresis, capillary blotted into hybridization membranes and hybridized with $^{32}$P-labeled bg28 cDNA insert. Only for the erythroid cells, the only cells known to carry B-G antigen, was a hybridizing mRNA species found (FIG. 2A). The lack of hybridization seen for other tissues were not due to RNA degradation since the same samples were shown to hybridize to a β-actin probe in a parallel hybridization experiment (FIG. 2B). Bursa poly(A)+ RNA was similarly analyzed with both probes and was found to hybridize to only the β-actin probe (data not shown). The size of the erythroid mRNA that hybridized to the bg28 insert was 2.1 kb, which is sufficiently long to encode a protein of 48 kDa.

Hybridization of bg28 to genomic DNA from chickens differing at the B system loci. Additional evidence for the identity of bg28 as a cDNA clone from the B-G region of the chicken MHC are provided by the patterns of hybridization of this clone to restriction endonuclease-digested genomic DNA from chickens differing in MHC haplotype, as shown in Table 1.

TABLE 1

| Sources of Blood Samples Used in Southern Analyses | | | | |
|---|---|---|---|---|
| B Haplotype[1/] | B-G Allele | Line | Figure | Source |
| B[15] | B-G[15] | diploid | 3 | Cornell[a] |
| B[15] | B-G[15] | trisomic | 3 | Cornell[a] |
| B[15] | B-G[15] | tetrasomic | 3 | Cornell[a] |
| B[4] | B-G[4] | CC | 4 | Basel[b] |
| B[12] | B-G[12] | CB | 4 | Basel[b] |
| B[17] | B-G[17] | UCD-003 | 4 | Davis[c] |
| B[18] | B-G[18] | UCD-253 | 4 | Davis[c] |
| B[19] | B-G[19] | UCD-235 | 4 | Davis[c] |
| B[23] | B-G[23] | UNH-105 | 4 | DeKalb[d] |
| B[24] | B-G[24] | UNH-105 | 4 | DeKalb[d] |
| B[Q] | B-G[Q] | UCD-001 | 4 | Davis[c] |
| B[15] | B-G[15] | UCD-315 | 5 | Davis[c] |
| B[15rl] | B-G[21] | — | 5 | Basel[e] |
| B[21] | B-G[21] | UCD-330 | 5 | Davis[c] |

TABLE 1-continued

Sources of Blood Samples Used in Southern Analyses

| B Haplotype[1] | B-G Allele | Line | Figure | Source |
|---|---|---|---|---|
| $B^{21r3}$ | $B\text{-}G^{15}$ | — | 5 | Basel[e] |

[1] Assignment of haplotype based on Chicken MHC Nomenclature Workshop; see Briles, et al., Immunogenetics 15: 441–447 (1982).
[a] Bloom, et al., J.Heredity 76:146–154 (1985).
[b] Hasek, et al., Folia biol. (Praha), 12:335–341 (1966).
[c] Abplanalp, Inbred lines as genetic resources of chickens. Proceedings of the Third World Congress of Genetics Applied to Livestock Production, Lincoln, Nebraska, Vol. X, pp. 257–268 (1986).
[d] Briles, et al., Immunogenetics 15:449–452 (1982).
[e] Koch, et al., Tissue Antigens 21:129–137 (1983).

A first line of evidence supporting the designation of bg28 as a MHC clone was obtained by the analysis of genomic DNA from disomic, trisomic and tetrasomic chickens of $B^{15}$ haplotype. The recent demonstration of a linkage between the major histocompatibility (B) complex and the nucleolar organizer on a microchromosome in the chicken 6/ has made it possible to select polysomics of a single haplotype. As would be expected if the bg28 clone were an MHC element, an increasing intensity of hybridization was obtained between the probe genomic DNA prepared from diploid, trisomic and tetrasomic birds. See FIG. 3, three samples on left. In contrast, hybridization of an actin probe is uniform across the three samples. See FIG. 3, three samples on right.

6/ See Bloom, et al., J. Heredity 76:146–154 (1985).

In the second set of Southern hybridizations, bg28 was hybridized with PvuII-digested DNA from eight lines of chickens differing at the MHC (see FIG. 4), restriction fragment length polymorphisms would be predicted if the clone is indeed from this region of the chicken genome. Antigens of the chicken MHC have been demonstrated previously to be polymorphic both immunologically 7/ and biochemically. A polymorphic pattern of restriction fragment lengths is evident when bg28 is used as a probe.

7/ See Briles, et al., Immunogenetics 15:441–447 (1982).

The third line of evidence from genomic DNA studies for the designation of bg28 as a chicken MHC clone, and for its identity with the B-G subregion is provided by the pattern of hybridization of this clone with DNA from MHC recombinant haplotypes. Substantially reciprocal recombinants, designated as $B^{15r1}$ and $B_{21r3}$ which are B-G21-B-F15 and B-G15-B-F21, respectively provide a means of further testing the bg28 clone for assignment to the B-G subregion. As would be predicted, the restriction fragment length pattern of hybridization of this probe with both recombinants produces a pattern indicating that the B-G subregion is that which has been cloned. See FIG. 5.

Sequence of the bg28 and comparison of the amino acid composition translated sequence with the amino acid composition of purified protein. bg28 was subcloned into M13mp19 and the entire insert sequenced in one direction by the dideoxy-chain-termination method. Translation of this nucleotide sequence and its complement into peptide sequence in all six reading frames produced only one peptide without internal stop codons. See FIGS. 6 (SEQ ID NO. 1) and 7 (SEQ ID NO. 2). Two nucleotide sequences of bg28 are presented. The first determination was made by sequencing only one strand of the cloned fragment, and the second was a full sequence determination on both strands. The two sequences determinations are 99% identical. The differences between the first and second determinations are minor, they consist of: (1) a change from G>C at position 72, (2) the deletion of ATC at positions 258–260, (3) the deletion of A at position 354, (4) the insertion of A at position 490, and (5) the transposition of GC to CG at positions 506–507. The differences are of such a minor nature that probes of either sequence would provide identical RFLP patterns in Southern hybridizations. As Table 2 shows, the amino acid composition of this peptide (genotype unknown) compares well with the amino acid composition of the B-G21.

TABLE 2

Amino Acid Composition Comparison

| | B-G21 antigen | Translated bg28 | Ratio |
|---|---|---|---|
| Ala | 41 | 11 | 3.7 |
| Cys | 6 | 5 | 1.2 |
| Phe | 37 | 13 | 2.85 |
| His | 12 | 4 | 3 |
| Ile | 17 | 10 | 1.7 |
| Lys | 48 | 8 | 4.2 |
| Leu | 48 | 15 | 3.2 |
| Met | 8 | 2 | 4 |
| Asx (Asn or Asp) | 39 | 14 | 2.8 |
| Pro | 17 | 1 | 17 |
| Glx (Gln or Glu) | 70 | 21 | 3.3 |
| Arg | 31 | 18 | 1.7 |
| Ser | 24 | 17 | 2.1 |
| Thr | 19 | 7 | 2.7 |
| Val | 30 | 17 | 1.8 |
| Trp | — | 3 | — |
| Tyr | 13 | 5 | 2.6 |
| TOTAL | 431 | 167 | 2.6 |

A second cDNA probe useful in this invention and identified as bg32.1 was also subcloned into Blue-script and purified from the vector prior to labeling by random priming.

The bg32.1 is a 650 bp cDNA clone isolated from a lambda gt11 expression library made erythroid from erythrocyte mRNA 8/ by cross-hybridization with bg32, a clone originally obtained screening the same library with antibodies prepared against purified B-G 21 antigen as described above. Under conditions of high stringency, the bg32 and bg32.1 fragments fail to hybridize with the previously described bg28 clone. However, as demonstrated previously with bg28, the bg32.1 clone can be assigned to B system-bearing microchromosome and further assigned to the B-G subregion on the basis of the patterns of hybridization with DNA from birds polysomic for the B system bearing microchromosome and with DNA from MHC recombinant haplotypes (FIG. 8). The intensity of hybridization of the bg32.1 probe to the DNA of polysomic birds increases proportionate to the copy number of the B system bearing microchromosome. The bg32.1 probe can be further assigned to the B-G subregion on the basis of the pattern of hybridization with DNA from B system recombinants derived from two independent recombinant events which produced essentially reciprocal rearrangements of the B-F/B-L and B-G subregions in $B^{15}$ and $B^{21}$ haplotypes. The pattern of hybridization with DNA of the recombinants matches that of the B-G subregion contributing parental haplotype (FIG. 8). The nucleotide sequence of λbg32.1 is shown by FIG. 11 (SEQ ID NO. 3).

8/ Moon, R. T., et al., J. Cell Biol. 100:152–160 (1985).

High molecular weight DNA was isolated from blood samples collected from birds of known B system haplotype carried in several different flocks (see Table 3).

TABLE 3

B-G Genotypes Analyzed

| B-G Allele | B Haplo-Type | Illus-Line | Sample Status | Figure(s) Illustrating | Size | Source |
|---|---|---|---|---|---|---|
| B-G$^2$ | B$^2$ | RPRL-15.7-2* | C+ | 2 | 3 | East Lansing# |
| B-G$^2$ | B$^2$ | RPRL-15.6-2 | I,C | — | 3 | East Lansing |
| B-G$^2$ | B$^2$ | UCD-331 | I,C | — | 3 | Davis |
| B-G$^2$ | B$^2$ | Reference Stock | S | — | 1 | DeKalb |
| B-G$^3$ | B$^3$ | UCD-313 | I,C | 2 | 2 | Davis |
| B-G$^4$ | B$^4$ | PR-CC* | I,C | 2,3 | 1 | Basel |
| B-G$^5$ | B$^5$ | RPRL-15.151-5* | I | 2 | 2 | East Lansing |
| B-G$^6$ | B$^6$ | G-B2* | I | 2 | 1 | Athens |
| B-G$^{10}$ | B$^{10}$ | Reference Stock* | S | 2 | 2 | DeKalb |
| B-G$^{11}$ | B$^{11}$ | Wis 3* | S | 2,3 | 2 | DeKalb |
| B-G$^{12}$ | B$^{12}$ | PR-CB* | I,C | 2 | 1 | Basel |
| B-G$^{12}$ | B$^{12}$ | RPRL 15.C-12 | I,C | — | 2 | East Lansing |
| B-G$^{13}$ | B$^{13}$ | G-B1* | I | 2 | 1 | Athens |
| B-G$^{13}$ | B$^{13}$ | RPRL 15.p-13 | I,C | — | 2 | East Lansing |
| B-G$^{14}$ | B$^{14}$ | UCD-316 | I,C | 2 | 2 | Davis |
| B-G$^{15}$ | B$^{15}$ | RPRL-151$_5$-15* | I,C | 2 | 2 | East Lansing |
| B-G$^{15}$ | B$^{15}$ | Polysomic | S | 1 | 9 | Ithaca |
| B-G$^{15}$ | B$^{15}$ | UCD-254 | I,C | 4 | 2 | Davis |
| B-G$^{15}$ | B$^{15}$ | UCD-011 | I | — | 2 | Davis |
| B-G$^{15}$ | B$^{15}$ | UCD-057 | I | — | 2 | Davis |
| B-G$^{15}$ | B$^{15}$ | UCD-035 | I | — | 1 | Davis |
| B-G$^{15}$ | B$^{21r3}$, R$^{5'}$, | UCD-386 | I,R | — | 2 | Basel/Davis |
| B-G$^{15}$ | B$^{15}$ | UCD-396(BN) | I | — | 1 | Davis |
| B-G$^{17}$ | B$^{17}$ | UCD-003* | I,C | 2,4 | 4 | Davis |
| B-G$^{18}$ | B$^{18}$ | UCD-253* | I,C | 2 | 2 | Davis |
| B-G$^{19}$ | B$^{19}$ | RPRL.15.P-19* | I,C | 2 | 2 | East Lansing |
| B-G$^{19}$ | B$^{19}$ | UCD-335 | I,C | 2 | 2 | Davis |
| B-G$^{21}$ | B$^{21}$ | RPRL.15N-21* | I,C | 2 | 3 | East Lansing |
| B-G$^{21}$ | B$^{21}$ | UCD-330 | I,C | 1 | >20 | Davis |
| B-G$^{21}$ | B$^{21}$ | UCD-100 (Australorp) | I | — | 5 | Davis |
| B-G$^{21}$ | B$^{21}$ | Ref. Stock | S | — | 1 | DeKalb |
| B-G$^{21}$ | B$^{15rl}$ | R$^4$, UCD-387 | I,R | 1 | 2 | Basel/Davis |
| B-G$^{23}$ | B$^{23}$ | UNH-105* | S | 2 | 1 | DeKalb |
| B-G$^{24}$ | B$^{24}$ | UNH-105* | S | 2 | 1 | DeKalb |
| B-G$^{24}$ | B$^{24}$ | UCD-312 | I | — | 1 | Davis |
| B-G$^C$ | B$^C$ | UCD-342 (Ceylonese X Red Jungle Fowl) | I,C | — | 1 | Davis |
| B-G$^J$ | B$^J$ | UCD-333 (Red Jungle Fowl) | I | — | 1 | Davis |
| B-G$^O$ | B$^O$ | UCD-104 | I,C | — | 1 | Davis |
| B-G$^Q$ | B$^Q$ | UCD-336 (Red Jungle Fowl) | I | — | 1 | Davis |

* Reference lines used as the type population in standardizing the B system nomenclature (see Briles et al., Immunogenetics 15:441-447 (1982)), although the RPRL samples are now represented by congenic lines.

Samples were taken from one or more individuals of each flock examined. FIGS. 9A and 9B depict patterns of hybridization between bg28 and bg32.1 and Pvu II digested DNA from a single representative from each of the 17 standard haplotypes examined. Multiple DNA restriction fragments, 4-10 per haplotype ranging size from approximately 1 to about 10 Kb are detected by the two probes. Some fragments are common to the patterns produced by both probes. For example, the three largest fragments in the B-G$^{21}$ patterns produced with both probes appear identical. Other fragments are detected only by one or the other of the probes. A number of the restriction fragments appear to be widely shared among the haplotypes, although with the exception of perhaps one fragment of about 5.2 Kb present in Pvu II-digested DNA probed with bg28, none are shared in common across all the haplotypes examined. The B-G subregions are each so different, as reflected in the restriction fragment patterns, that generally the different genotypes can be distinguished readily from each other in a Southern hybridization using this single restriction enzyme and either of the two B-G c-DNA probes. The only exceptions appear to be the patterns produced by DNA from birds of B⁴ and B¹¹ haplotypes. The other important finding is that without exception the restriction fragment patterns were the same for each B-G allele across the samples included in this study including samples obtained from different populations known on the basis of serological typing to carry the same B haplotypes.

In order to distinguish clearly the B-G genotype of B⁴ and B¹¹ birds, it was necessary to employ additional restriction enzymes. Among the digestions with five restriction enzymes only those produced with Eco RI provided patterns clearly differentiating the two B-G genotypes (FIG. 10). It is notable that even with this enzyme the patterns of the two haplotypes differ only by a proportionate shift in the size of two restriction fragments out of the seven fragments produced.

Additional cDNA probes derived from erythrocytic mRNA of B²¹ haplotype useful in this invention and identified as bg11 (FIG. 12) (SEQ ID NO. 4), bg14 (FIG. 13) (SEQ ID NO. 5), bg3 (FIG. 14) (SEQ ID NO. 6), bg8 (FIG. 15) (SEQ ID NO. 7) and bg17 (FIG. 16) (SEQ ID NO. 8), as well as the additional clones gi6 (FIG. 17) (SEQ ID NO. 9), gi9 (FIG. 18) (SEQ ID NO. 10)and gi11 (FIG. 19) (SEQ ID NO. 11) derived from mRNA of the small intestine (also B²¹) were also subcloned into Bluescript, fully sequenced and found to have properties like those of bg28 and bg32.1 when employed in the Southern hybridizations. The strong sequence similarity among all the cDNA clones is depicted in FIG. 20 (SEQ ID NO. 12) where all the cDNA clone sequences are compared to bg14 (a full length cDNA clone having no intronic sequences) using the ALIGN program in DNASTAR. (ALIGN is an algorithm for optimal local alignment of two partially homologous DNA sequences.) These sequences, encompassing full-length (also including introns in some), near the full-length or partial lengths of transcripts for individual B-G polypeptides, all show significant sequence similarity with bg14. Moreover, bg14 shows significant similarity to the nucleotide sequence of a 4,757 Kb fragment of chicken genomic DNA, typifying a segment of genomic DNA to which these B-G cDNA clones would hybridize will hybridize under straight conditions. Using the SEQCOMP program in DNA-STAR (an algorithm appropriate for alignment with very large sequences in a reasonable length of time by time locating regions of perfect match and then optimizing fit) sequences the similarity between the two sequences is 89%.

Analysis of these sequences have provided an understanding of the organization of the B-G transcripts and prediction of the amino acid sequence of the B-G polypeptides. For purposes of illustration the organization of bg14 is described. The fully processed transcript cloned in bg14 is 1816 bp. It contains both 5'- and 3'- noncoding sequences. An open reading frame corresponds to a 398 amino acid polypeptide (including signal peptide) with calculated $M_r$ 45,298. Within the coding region there are sequences for: (a) a N-terminal signal peptide of 34 amino acids, (b) a single extracellular domain (amino acid residues 35-148), (c) a transmembrane domain (residues 149-178), and (d) a cytoplasmic region made up from a series of domains (residues 179-398). The single extracellular domain has properties that identify as highly similar to members of the immunoglobulin gene superfamily. The intracellular domains are characterized by a strong heptad pattern, repeats of seven amino acids the seventh residue of which is nearly always hydrophobic. This pattern is consistent with the primary sequence patterns of molecules α-alpha helical coiled coil conformation. All the cDNA clones are similarly organized. Some are missing portions of the full transcript sequence (for example bg17 is missing a portion of the 5' end and bg11 is missing a small portion at the 3' end) and some contain unprocessed introns (bg8, for example, possesses 9 unprocessed introns; bg11 contains 1). Comparisons of the sequences bg28 and bg32.1 with the sequences of clones full transcripts provide evidence that these probes encompass respectively portions of the 5' end and 3' end of B-G transcripts.

Since none of the transcripts represented in the sequences of these clones are identical, except for bg14 and bg8 which apparently represent the same transcript type and differ only by the presence of intronic sequences with bg8 and a single, silent base difference, there is now evidence for the expression of 8 transcript types, Six of these are from libraries of B²¹ haplotype and the remaining two, bg28 and bg32.1 are from birds of unknown genetic background. Hence the multiple transcript types provide evidence for the expression of alleles are multiple loci within the B-G subregion. Probes derived from these cDNA clones hybridize under stringent conditions (e.g., overnight aqueous hybridization in 5× SSPE, 5× Denhardt's, 1% SDS, 100 ug/ml salmon sperm DNA, ³²P-labeled denatured probe at 65° C. and stringent temperature wash at 65° C. in 0.5× SSC) to multiple bands in Southern hybridizations with genomic DNA from chickens of many different haplotypes, as illustrated by FIGS. 3, 4, 5, 9 (A and B), and 10. Hybridization temperatures and wash temperatures of from about 55° C. to about 70° C. are appropriate.

These sequences and subsequences derived from them for the production of synthetic oligonucleotide probes have the capability for producing RFLP patterns by hybridization with gene sequences in other bird species. Illustrated in FIG. 23 is the hybridization of bg11 under moderately high stringency (overnight aqueous hybridization in 5× SSPE, 5× Denhardt's, 1% SDS, 100 ug/ml salmon sperm DNA, ³²P-labeled denatured probe at 60° C. and stringent temperature wash at 60° C. in 0.5× SSC) and produces polymorphic band patterns with Sst 1 digested genomic from turkeys.

The capability of these probes to produce RFLP patterns in genomic DNA of other bird species is further illustrated by FIG. 24 where bg32.1 hybridizes to multiple, polymorphic bands in genomic DNA from a family of ring-necked pheasants serologically B typed.

---

SEQUENCE LISTING ( 1 ) GENERAL INFORMATION:

( i i i ) NUMBER OF SEQUENCES: 14

( 2 ) INFORMATION FOR SEQ ID NO: 1:

( i ) SEQUENCE CHARACTERISTICS:
    ( A ) LENGTH: 525
    ( B ) TYPE: Nucleic Acid
    ( C ) STRANDEDNESS: Double
    ( D ) TOPOLOGY: Linear ( i i ) MOLECULE TYPE: DNA ( v i ) ORIGINAL SOURCE: Synthetically Prepared ( v i i ) IMMEDIATE SOURCE: Synthetically Prepared ( x i ) SEQUENCE DESCRIPTION: SEQ ID NO: 1:

```
GAC ATC AGA TGG ATC CAG CAG CGG TCC TCT CGG CTT GTG CAC CAC    45
Asp Ile Arg Trp Ile Gln Gln Arg Ser Aer Arg Leu Val His His
 1               5                  10                  15

TAC CGA AAT GGA GTG GAC CTG GGG CAC ATG GAG GAA TAT AAA GGG    90
Tyr Arg Asn Gly Val Asp Leu Gly His MET Glu Glu Tyr Lys Gly
                 20                  25                  30

AGA ACA GAA CTG CTC AGG GAT GGT CTC TCT GAT GGA AAC CTG GAT   135
Arg Thr Glu Leu Leu Arg Asp Gly Leu Ser Asp Gly Asn Leu Asp
                 35                  40                  45

TTG CGC ATC ACT GCT GTG ACC TCC TCT GAT AGT GGC TCC TAC AGC   180
Leu Arg Ile Thr Ala Val Thr Ser Ser Asp Ser Gly Ser Tyr Ser
                 50                  55                  60

TGT GCT GTG CAA GAT GGT GAT GCC TAT GCA GAA GCT GTG GTG AAC   225
Cys Ala Val Gln Asp Gly Asp Ala Tyr Ala Glu Ala Val Val Asn
                 65                  70                  75

CTG GAG GTG TCA GAC CCC TTT TCT ATG ATC ATC ATC CTT TAC TGG   270
Leu Glu Val Ser Asp Pro Phe Ser MET Ile Ile Ile Leu Tyr Trp
                 80                  85                  90

ACA GTG GCT CTG GCT GTG ATC ATC ACA CTT CTG GTT GGG TCA TTT   315
Thr Val Ala Leu Ala Val Ile Ile Thr Leu Leu Val Gly Ser Phe
                 95                 100                 105

GTC GTC AAT GTT TTT CTC CAT AGA AAG AAA GTG GCA CAA GAG CAG   360
Val Val Asn Val Phe Leu His Arg Lys Lys Val Ala Gln Glu Gln
                110                 115                 120

AGA GCT GAA GAG AAA AGA TGC AGA GTT GGT GGA GAA AGC TGC AGC   405
Arg Ala Glu Glu Lys Arg Cys Arg Val Gly Gly Glu Ser Cys Ser
                125                 130                 135

ATT GGA GAG AAA AGA TGC AGA GTT GGC GGA ACA AGC AGC GCA ATC   450
Ile Gly Glu Lys Arg Cys Arg Val Gly Gly Thr Ser Ser Ala Ile
                140                 145                 150

GAA GCA AAG AGA TGC AAT GTT GGA CAA ACA CGT TCT AAA CTG GAG   495
Glu Ala Lys Arg Cys Asn Val Gly Gln Thr Arg Ser Lys Leu Glu
                155                 160                 165

GAA AGA CAG AGC AAG TGG AGA TTG GAA TTC                       525
Glu Arg Gln Ser Lys Trp Arg Leu Glu Phe
                170                 175
```

( 2 ) INFORMATION FOR SEQ ID NO: 2:

( i ) SEQUENCE CHARACTERISTICS:
        ( A ) LENGTH: 523
        ( B ) TYPE: Nucleic Acid
        ( C ) STRANDEDNESS: Double
        ( D ) TOPOLOGY: Linear ( i i ) MOLECULE TYPE: DNA ( v i ) ORIGINAL SOURCE: Synthetically Prepared ( v i i ) IMMEDIATE SOURCE: Synthetically Prepared ( x i ) SEQUENCE DESCRIPTION: SEQ ID NO: 2:

```
GAC ATC AGA TGG ATC CAG CAG CGG TCC TCT CGG CTT GTG CAC CAC    45
```

| | | | | | | | | | | | | | | |
|---|---|---|---|---|---|---|---|---|---|---|---|---|---|---|
| TAC | CGA | AAT | GGA | GTG | GAC | CTG | GGG | CAG | ATG | GAG | GAA | TAT | AAA | GGG | 90 |
| AGA | ACA | GAA | CTG | CTC | AGG | GAT | GGT | CTC | TCT | GAT | GGA | AAC | CTG | GAT | 135 |
| TTG | CGC | ATC | ACT | GCT | GTG | ACC | TCC | TCT | GAT | AGT | GGC | TCC | TAC | AGC | 180 |
| TGT | GCT | GTG | CAA | GAT | GGT | GAT | GCC | TAT | GCA | GAA | GCT | GTG | GTG | AAC | 225 |
| CTG | GAG | GTG | TCA | GAC | CCC | TTT | TCT | ATG | ATC | ATC | CTT | TAC | TGG | ACA | 270 |
| GTG | GCT | CTG | GCT | GTG | ATC | ATC | ACA | CTT | CTG | GTT | GGG | TCA | TTT | GTC | 315 |
| GTC | AAT | GTT | TTT | CTC | CAT | AGA | AAG | AAA | GTG | GCA | CAG | AGC | AGA | GAG | 360 |
| CTG | AAG | ABA | AAA | GAT | GCA | GAG | TTG | GTG | GAG | AAA | GCT | GCA | GCA | TTG | 405 |
| GAG | AGA | AAA | GAT | GCA | GAG | TTG | GCG | GAA | CAA | GCA | GCG | CAA | TCG | AAG | 450 |
| CAA | AGA | GAT | GCA | ATG | TTG | GAC | AAA | CAC | GTT | CTA | AAA | CTG | GAG | GAA | 495 |
| AAG | ACA | GAC | GAA | GTG | GAG | ATT | GGA | ATT | C | | | | | | 523 |

(2) INFORMATION FOR SEQ ID NO: 3:

(i) SEQUENCE CHARACTERISTICS:
        (A) LENGTH: 634
        (B) TYPE: Nucleic Acid
        (C) STRANDEDNESS: Double
        (D) TOPOLOGY: Linear (ii) MOLECULE TYPE: DNA (vi) ORIGINAL SOURCE: Synthetically Prepared (vii) IMMEDIATE SOURCE: Synthetically Prepared (xi) SEQUENCE DESCRIPTION: SEQ ID NO: 3:

| | | | | | | | | | | | | | | |
|---|---|---|---|---|---|---|---|---|---|---|---|---|---|---|
| CGG | TGA | ACA | GAT | GGA | GAG | AAG | GAA | TGC | AAA | GTT | GGA | GGC | AGC | AGC | 45 |
| TGT | AAA | ACT | GGG | ACA | CAA | AGC | TAA | AGA | ATC | AGA | GAA | ACA | GAA | ATC | 90 |
| GGA | GCT | GAA | GGA | GCG | CCA | TGA | GGA | GAT | GGC | AGA | ACA | AAC | TGA | AGC | 135 |
| AGT | GGT | GGT | AGA | AAC | TGA | AGA | ATA | GGA | AAA | ACC | ATC | TGA | AGA | ATC | 180 |
| AGA | TTG | AGA | GAT | GAA | CTG | CGC | CTC | ACA | ATA | AGC | ACA | GGA | GTT | AAG | 225 |
| CTT | CTT | AGA | TCA | ATA | ACT | GCA | CAG | CAT | ACA | AAA | CCA | CAA | TAA | CTC | 270 |
| AAA | CAG | AGT | AAG | GAG | GAG | CCA | GTG | TTT | GTG | TTG | AGT | GAG | AAC | ACT | 315 |
| GCA | GTT | CTG | TCA | GCC | AAA | GCT | GCC | TGA | GGG | ACC | GCC | AAT | TGA | GG | 360 |
| GTG | TGT | GAC | CTC | CAA | CTC | AAA | TCC | AGT | TGG | AAG | AAA | GAA | ACC | ATA | 405 |
| GAA | AGG | AAG | GAA | AGG | GGA | GGA | AGA | CAG | AGA | TCC | TGG | AAG | AGA | TAT | 450 |
| GGG | CAT | TTG | GGG | AAA | TAG | TGT | GAT | CAT | GTA | TCA | GGC | TTT | GTG | GAC | 495 |
| ATC | TAA | TGA | ATA | TGT | CAT | GCT | TTT | GTA | ACT | ACA | AGC | ATG | CAC | GCA | 540 |
| GAA | ACA | AAG | GTA | GAA | AAC | TGC | TTT | GGG | TGT | TAG | CAC | TGT | TCT | CTG | 585 |
| TCA | CTA | TAT | AAT | AAA | GAA | TAC | CTG | CTG | ATG | GCA | ATG | GAA | CAA | AAA | 630 |
| AAA | A | | | | | | | | | | | | | | 634 |

(2) INFORMATION FOR SEQ ID NO: 4:

(i) SEQUENCE CHARACTERISTICS:
        (A) LENGTH: 1785
        (B) TYPE: Nucleic Acid
        (C) STRANDEDNESS: Double
        (D) TOPOLOGY: Linear (ii) MOLECULE TYPE: DNA (vi) ORIGINAL SOURCE: Synthetically Prepared ( v i i ) IMMEDIATE SOURCE: Synthetically Prepared ( x i ) SEQUENCE DESCRIPTION: SEQ ID NO: 4:

| | | | | | | | | | | | | | | |
|---|---|---|---|---|---|---|---|---|---|---|---|---|---|---|
| ATC | CGT | TCG | AGC | TCT | CTC | CTC | CTA | CAG | CTG | CTG | CCC | TCA | TAT | TCT | 45 |
| CCC | CAC | ACT | TCT | TCC | CCA | TAT | TCT | TTC | CAA | ATC | CTC | TTC | CCC | ATC | 90 |
| TCC | TCC | ACC | GTC | TCT | TTC | TCA | GAG | TCC | TTC | CTC | TCT | CTC | CCT | AAA | 135 |
| TTC | TTC | CCC | CCT | CCT | CTC | CTC | CAG | CAC | AGA | TGC | GCT | TCA | CAT | CGG | 180 |
| GAT | GCA | ACC | ACC | CCA | GTT | TCA | CCC | TCC | CCT | GGA | GGA | CCC | TCC | TGC | 225 |
| CTT | ATC | TCG | TGG | CTC | TGC | ACC | TCC | TCC | AGC | CGG | GAT | CAG | CCC | AGC | 270 |
| TCA | GGG | TGG | TGG | CGC | CGA | GCC | TCC | GTG | TCA | CTG | CCA | TCG | TGG | GAC | 315 |
| AGG | ATG | TCG | TGC | TGC | GCT | GCC | ACT | TGT | GCC | CTT | GCA | AGG | ATG | CTT | 360 |
| GGA | GAT | TGG | ACA | TCA | GAT | GGA | TCC | TGC | AGC | GGT | CCT | CTG | GTT | TTG | 405 |
| TGC | ACC | ACT | ATC | AAA | ATG | GAG | TGG | ACC | TTG | GGC | AGA | TGG | AGG | GAT | 450 |
| ATA | AAG | GGA | GAA | CAG | AAC | TGC | TCA | GGG | ATG | GTC | TCT | ATG | ATG | GAA | 495 |
| ACC | TGG | ATT | TGC | GCA | TCA | CTG | CTG | TGA | GCA | CCT | CCG | ATA | GTG | GCT | 540 |
| CAT | ACA | GCT | GTG | CTG | TGC | AGG | ATG | GTG | ATG | GCT | ATG | CAG | ACG | CTG | 585 |
| TGG | TGG | ACC | TGG | AGG | TGT | CAG | ATC | CCT | TTT | CCC | AGA | TCG | TCC | ATC | 630 |
| CCT | GGA | AGG | TGG | CTC | TGG | CTG | TGG | TCG | TCA | CAA | TTC | TCG | TTG | GGT | 675 |
| CAT | TTG | TCA | TCA | ATG | TTT | TTC | TCT | GTA | GGA | AGA | AAG | CGG | CAC | AGA | 720 |
| GCA | GAG | AGC | TGA | GTG | AGT | CCT | TCC | AGC | CCC | TTC | CAC | CAC | CAA | AGT | 765 |
| CCC | TTT | AAT | GGA | ACT | GAT | AGA | AGA | CTG | CAG | AGT | GCT | GGG | TTT | ATG | 810 |
| CCT | TGT | GCT | GGG | GCC | ATG | GGA | TCT | ATG | GGA | CCT | TGG | GAT | GTG | TTG | 855 |
| GGG | CCG | TGG | GAT | GTG | CTG | GGG | TCG | TGG | GAT | CTG | TCA | ACC | CTG | ATT | 900 |
| GAT | CCA | CTT | CAG | AAC | TCT | TGC | CCA | ATC | GGT | TCC | TTC | CGA | TTC | ATT | 945 |
| TAA | CTC | CTT | CTT | GAG | GCC | AAA | GTG | GTC | ATT | GGC | CAC | ATC | CCA | TAA | 990 |
| AAA | AGG | GTT | TGG | GGT | CAG | GGT | GTG | GGA | GCT | GAT | CGC | ATG | GAA | ACG | 1035 |
| TGT | CCC | CTC | TGA | CCA | TGC | ATT | TCA | TTT | GCT | TCT | ATT | TTG | CAG | AGA | 1080 |
| GAA | AAG | ATG | CAG | CGT | TGG | CGG | AAC | TAG | ATG | AGA | TAT | CGG | GTT | TAA | 1125 |
| GTG | CTG | AAA | ATC | TGA | AGC | AAT | TAG | CTT | CAA | AAC | TGA | ACG | AAA | ATG | 1170 |
| CTG | ACG | AAG | TGG | AGG | ATT | GCA | ATT | CAG | AGC | TGA | AGA | AAG | ACT | GTG | 1215 |
| AAG | AGA | TGG | GTT | CTG | GCG | TTG | GAG | ATC | TGA | AGG | AAC | TGG | CTG | CAA | 1260 |
| AAT | TGG | AGG | AAT | ATA | TTG | CAG | TGA | ATC | GGA | GAA | GGA | ATG | TAA | AGT | 1305 |
| TGA | ATA | ATA | TAG | CTG | CCA | AAC | TGG | CAC | AAC | AAA | CTA | AAG | AAT | TGG | 1350 |
| AGA | AAC | AGC | ATT | CAC | AGT | TCC | ACA | GAC | ACT | TTC | AGC | GTA | TGG | ATT | 1395 |
| TAA | GTG | CTG | TAA | ACC | AGA | AGA | AAC | TGG | TTA | CAA | AAC | TGG | AGG | AAC | 1440 |
| ACT | TTG | AAT | GGA | TGG | AGA | GAA | GGA | ATG | TAA | AGT | TGG | AGA | TAC | CAG | 1485 |
| CTG | TAA | TAC | TGG | GGC | AAC | AAG | CTA | AAG | AAT | CAG | AGA | AAC | AGA | AAT | 1530 |
| CGG | AGC | TGA | AGG | AGC | GCC | ATG | AGG | AGA | TGG | CAG | AAC | AAA | CTG | AAG | 1575 |
| CAG | TGG | TGG | TAG | ATA | CTG | AAG | AAG | CGG | AAA | AAC | CAT | CTG | AAG | AAT | 1620 |
| TGG | ATT | GAG | AGA | TGA | ACT | GCG | CCT | CAC | AGT | AAC | CAC | AGG | AGT | TAA | 1665 |
| GCT | TCA | TAG | ATC | AAT | GAC | TGC | ACA | GCA | TAC | AAA | AAC | CAC | GAT | ACC | 1710 |
| TCA | AAC | AGA | GCA | AGG | AAA | TCC | ACA | GCG | AGA | ACA | AGA | GGA | GCC | AGT | 1755 |

| | | | | | | | | | | |
|---|---|---|---|---|---|---|---|---|---|---|
| GTT | TGT | GTT | GAG | TGA | GAA | CAC | TGC | AGT | TCT | 1785 |

( 2 ) INFORMATION FOR SEQ ID NO: 5:

( i ) SEQUENCE CHARACTERISTICS:
        ( A ) LENGTH: 1816
        ( B ) TYPE: Nucleic Acid
        ( C ) STRANDEDNESS: Double
        ( D ) TOPOLOGY: Linear ( i i ) MOLECULE TYPE: DNA ( v i ) ORIGINAL SOURCE: Synthetically Prepared ( v i i ) IMMEDIATE SOURCE: Synthetically Prepared ( x i ) SEQUENCE DESCRIPTION: SEQ ID NO: 5:

| | | | | | | | | | | |
|---|---|---|---|---|---|---|---|---|---|---|
| TTC | TGC | CCT | CAT | ATT | CTC | CCC | ACA | CTT | CTT | 45 |
| CCC | CAT | ATT | CTT | TCC | | | | | | |
| AAA | TCC | TCT | TCC | CCA | TCT | CCT | CCA | TCG | TCT | 90 |
| CCT | TCT | CAG | AGT | CCT | | | | | | |
| TCC | TCT | CTC | TCC | CTA | AAT | TCT | TCC | CCC | CTC | 135 |
| CTC | TTC | TCC | AGC | ACA | | | | | | |
| GAT | GGC | CTT | CAC | ATC | GGG | CTG | CAA | CCA | CCC | 180 |
| CAG | TTT | CAC | CCT | CCC | | | | | | |
| CTG | GAG | GAC | CCT | CCT | GCC | TTA | TCT | CGT | GGC | 225 |
| TCT | GCA | CCT | CCT | CCA | | | | | | |
| GCC | GGG | ATC | AGC | CCA | GAT | CAC | GGT | GGT | GGC | 270 |
| ACC | GAG | CCT | CCG | TGT | | | | | | |
| CAC | TGC | CAT | CGT | GGG | ACA | GGA | TGT | TGT | GCT | 315 |
| GCG | CTG | CCA | CTT | GTC | | | | | | |
| CCC | ATG | CAA | GGA | TGT | TCG | GAA | TTC | AGA | CAT | 360 |
| CAG | ATG | GAT | CCA | GCA | | | | | | |
| GCG | GTC | CTC | TCG | GCT | TGT | GCA | CCA | CTA | CCG | 405 |
| AAA | TGG | AGT | GGA | CCT | | | | | | |
| GGG | GCA | GAT | GGA | GGA | ATA | TAA | AGG | GAG | AAC | 450 |
| AGA | ACT | GCT | CAG | GGA | | | | | | |
| TGG | TCT | CTC | TGA | TGG | AAA | CCT | GGA | TTT | GCG | 495 |
| CAT | CAC | TGC | TGT | GAC | | | | | | |
| CTC | CTC | TGA | TAG | TGG | CTC | CTA | CAG | CTG | TGC | 540 |
| TGT | GCA | AGA | TGG | TGA | | | | | | |
| TGC | CTA | TGC | AGA | AGC | TGT | GGT | GAA | CCT | GGA | 585 |
| GGT | GTC | AGA | CCC | CTT | | | | | | |
| TTC | TAT | GAT | CAT | CCT | TTA | CTG | ACA | GT | GGC | 630 |
| TCT | GGC | TGT | GAT | CAT | | | | | | |
| CAC | ACT | TCT | GGT | TGG | GTC | ATT | TGT | CGT | CAA | 675 |
| TGT | TTT | TCT | CCA | TAG | | | | | | |
| AAA | GAA | AGT | GGC | ACA | GAG | CAG | AGA | GCT | GAA | 720 |
| GAG | AAA | AGA | TGC | AGA | | | | | | |
| GTT | GGT | GGA | GAA | AGC | TGC | AGC | ATT | GGA | GAG | 765 |
| AAA | AGA | TGC | AGA | GTT | | | | | | |
| GGC | GGA | ACA | AGC | AGC | GCA | ATC | GAA | GCA | AAG | 810 |
| AGA | TGC | AAT | GTT | GGA | | | | | | |
| CAA | ACA | CGT | TCT | AAA | ACT | GGA | GGA | AAA | GAC | 855 |
| AGA | CGA | AGT | GGA | GAA | | | | | | |
| CTG | GAA | TTC | AGT | GCT | GAA | AAA | AGA | CAG | TGA | 900 |
| AGA | GAT | GGG | TTA | TGG | | | | | | |
| CTT | TGG | AGA | TCT | GAA | GAA | ACT | GGC | TGC | AGA | 945 |
| ACT | GGA | GAA | ACA | CTC | | | | | | |
| TGA | AGA | GAT | GGG | GAC | AAG | GGA | TTT | AAA | GTT | 990 |
| GGA | GCG | ACT | AGC | TGC | | | | | | |
| CAA | ACT | GGA | ACA | TCA | AAC | TAA | AGA | ATT | GGA | 1035 |
| GAA | ACA | GCA | TTC | ACA | | | | | | |
| GTT | CCA | GAG | ACA | CTT | TCA | GAA | TAT | GTA | TTT | 1080 |
| AAG | TGC | TGG | AAA | ACA | | | | | | |
| GAA | GAA | AAT | GGT | TAC | AAA | ACT | GGA | GGA | ACA | 1125 |
| CTG | TGA | ATG | GAT | GGT | | | | | | |
| GAG | AAG | GAA | TGT | AAA | GTT | GGA | GAT | ACC | AGC | 1170 |
| TGT | AAA | AGT | GGG | GCA | | | | | | |
| ACA | AGC | TAA | AGA | ATC | AGA | GGA | ACA | GAA | ATC | 1215 |
| GGA | GCT | GAA | GGA | GCA | | | | | | |
| CCA | TGA | GGA | GAC | GGG | GCA | ACA | AGC | TAA | AGA | 1260 |
| ATC | AGA | GAA | ACA | GAA | | | | | | |
| ATC | GGA | GCT | GAA | GGA | GCG | CCA | TGA | GGA | GAT | 1305 |
| GGC | AGA | ACA | AAC | TGA | | | | | | |
| AGC | AGT | GGT | GGT | AGA | AAC | TGA | AGA | ATA | GGA | 1350 |
| AAA | ACC | ATC | TGA | AGA | | | | | | |
| ATT | GGA | TTG | AGA | GAT | GAA | CTG | CGC | CTC | GCA | 1395 |
| GTA | ACC | ACA | GGA | GTT | | | | | | |
| AAG | CTT | CAT | AGA | TCA | ATA | ACT | GCA | CAG | CAT | 1440 |
| ACA | AAA | CCA | CAA | TAA | | | | | | |

| | | | | | | | | | | |
|---|---|---|---|---|---|---|---|---|---|---|
| CTC | AAA | CAG | GGT | AAG | GAG | GAG | CCA | GTG | TTT | GTG | TTG | AGT | GAG | AAC | 1485 |
| ACT | GCA | GTT | CTG | TCA | GCC | AAA | GCT | GCC | TGA | GGG | ACC | GCC | CAA | TTG | 1530 |
| AGG | GTG | TGC | GAC | CTC | CAA | CTC | AAA | GCC | AAT | TGG | AAG | AAA | GAA | ACC | 1575 |
| ATA | GAA | AGG | AAG | AAA | AGG | GGA | GGA | AGA | CAG | AGA | TCC | TGG | AAG | AGA | 1620 |
| TAT | GGG | CAT | TTG | GGG | AAA | TAG | TGT | GAC | CAT | GTA | TCA | GGC | TTT | GTG | 1665 |
| GAC | ATC | TAA | CGA | ATA | TGT | CAT | GTT | TTT | GTA | AAT | ACA | AGC | ATG | CAC | 1710 |
| GCA | GAA | ACA | AAG | GGA | GAA | AAC | TGC | TTT | GGG | TGT | TAG | CAC | TGT | TCT | 1755 |
| CTG | TCC | CTA | TAT | AAT | AAA | GAA | TAC | CTG | CTG | ATG | GCA | AAA | AAA | AAA | 1800 |
| AAA | AAA | AAA | AAA | AAA | A | | | | | | | | | | 1816 |

( 2 ) INFORMATION FOR SEQ ID NO: 6:

( i ) SEQUENCE CHARACTERISTICS:
        ( A ) LENGTH: 1822
        ( B ) TYPE: Nucleic Acid
        ( C ) STRANDEDNESS: Double
        ( D ) TOPOLOGY: Linear ( i i ) MOLECULE TYPE: DNA ( v i ) ORIGINAL SOURCE: Synthetically Prepared ( v i i ) IMMEDIATE SOURCE: Synthetically Prepared ( x i ) SEQUENCE DESCRIPTION: SEQ ID NO: 6:

| | | | | | | | | | | |
|---|---|---|---|---|---|---|---|---|---|---|
| AAA | TGA | AGA | CTT | CAG | GAT | CCT | TCC | ATA | AAA | GCT | ATC | AGT | TTG | ACT | 45 |
| TCA | GAG | AGG | GCT | ATT | CTC | GGT | GTT | TGC | AAG | AAG | CTT | TCC | ATC | GTC | 90 |
| TCC | TTC | TCA | GAG | TCC | TTC | CTC | TCT | CTC | CCT | AAA | TTC | TTC | CCC | CCT | 135 |
| CCT | CTT | CTC | CAG | CAC | AGA | TGG | CCT | TCA | CAT | CGG | GCT | GCA | ACC | ACC | 180 |
| CCA | GTT | TCA | CCC | TCC | CCT | GGA | GGA | CCC | TCC | TGC | CTT | ATC | TCG | TGG | 225 |
| CTC | TGC | ACC | TCC | TCC | AGC | CGG | GAT | CAG | CCC | AGA | TCA | CGG | TGG | TGG | 270 |
| CAC | CGA | GCC | TCC | GTG | TCA | CTG | CCA | TCG | TGG | GAC | AGG | ATG | TTG | TGC | 315 |
| TGC | GCT | GCC | ACT | TGT | CCC | CAT | GCA | AGG | ATG | TTC | GGA | ATT | CAG | ACA | 360 |
| TCA | GAT | GGA | TCC | AGC | AGC | GGT | CCT | CTC | GGC | TTG | TGC | ACC | ACT | ACC | 405 |
| GAA | ATG | GAG | TGG | ACC | TGG | GGC | AGA | TGG | AGG | AAT | ATA | AAG | GGA | GAA | 450 |
| CAG | AAC | TGC | TCA | GGG | ATG | GTC | TCT | CTG | ATG | GAA | ACC | TGG | ATT | TGC | 495 |
| GCA | TCA | CTG | CTG | TGA | CCT | CCT | CTG | ATA | GTG | GCT | CCT | ACA | GCT | GTG | 540 |
| CTG | TGC | AAG | ATG | GTG | ATG | CCT | ATG | CAG | AAG | CTG | TGG | TGA | ACC | TGG | 585 |
| AGG | TGT | CAG | ACC | CCT | TTT | CTA | TGA | TCA | TCC | TTT | ACT | GGA | CAG | TGG | 630 |
| CTC | TGG | CTG | TGA | TCA | TCA | CAC | TTC | TGG | TTG | GGT | CAT | TTG | TCG | TCA | 675 |
| ATG | TTT | TTC | TCC | ATA | GAA | AGA | AAG | TGG | CAC | AGA | GCA | GAG | AGC | TGA | 720 |
| AGA | GAA | AAG | ATG | CAG | AGT | TGG | TGG | AGA | AAG | CTG | CAG | CAT | GGA | AGA | 765 |
| GAA | AAG | ATG | CAG | AGT | TGG | CGG | AAC | AAG | CAG | CGC | AAT | CGA | AGC | AAA | 810 |
| GAG | ATG | CAA | TGT | TGG | ACA | AAC | ACG | TTC | TAA | AAC | TGG | AGG | AAA | AGA | 855 |
| CAG | ACG | AAG | TGG | AGA | ATT | GGA | ATT | CAG | TGC | TGA | AAA | AAG | ACA | GTG | 900 |
| AAG | AGA | TGG | GTT | ATG | GCT | TTG | AGA | TCT | GAA | AGA | AAC | TGG | CTG | CAG | 945 |
| AAC | TGG | AGA | AAC | ACT | CTG | AAG | AGA | TGG | GGA | CAA | GGG | ATT | TAA | AGT | 990 |
| TGG | AGC | GAC | TAG | CTG | CCA | AAC | TGG | AAC | ATC | AAA | CTA | AAG | AAT | TGG | 1035 |

| AGA | AAC | AGC | ATT | CAC | AGT | TCC | AGA | GAC | ACT | TTC | AGA | ATA | TGT | ATT | 1080 |
| AAA | GTG | CTG | GAA | AAC | AGA | AGA | AAA | TGG | TTA | CAA | AAC | TGG | AGG | AAC | 1125 |
| ACT | GTG | AAT | GGA | TGG | TGA | GAA | GGA | ATG | TAA | AGT | TGG | AGA | TAC | CAG | 1170 |
| CTG | TAA | AAG | TGG | GGC | AAC | AAG | CTA | AAG | AAT | CAG | AGG | AAC | AGA | AAT | 1215 |
| CGG | AGC | TGA | AGG | AGC | ACC | ATG | AGG | AGA | CGG | GGC | AAC | AAG | CTA | AAG | 1260 |
| AAT | CAG | AGA | AAC | AGA | AAT | CGG | AGC | TGA | AGG | AGC | GCC | ATG | AGG | AGA | 1305 |
| TGG | AAC | AAA | CTG | AAG | CAG | TGG | TGG | TAG | AAA | CTG | AAG | AAT | AGG | AAA | 1350 |
| AAC | CAT | CTG | AAG | AAT | TGG | ATT | GAG | AGA | TGA | ACT | GCG | CCT | CGC | AGT | 1395 |
| AAC | CAC | AGG | AGT | TAA | GCT | TCA | TAG | ATC | AAT | AAC | TGC | ACA | GCA | TAC | 1440 |
| AAA | ATC | ACA | ATA | ACT | CAA | ACA | GGG | TAA | GGA | GGA | GCC | AGT | GTT | TGT | 1485 |
| GTT | GAG | TGA | GAA | CAC | TGC | AGT | TCT | GTC | AGC | CAA | AGC | TGC | CTG | AGG | 1530 |
| GAC | CGC | CCA | ATT | GAG | GGT | GTG | CGA | CCT | CCA | ACT | CAA | AGC | CAA | TTG | 1575 |
| GAA | GAA | AGA | AAC | CAT | AGA | AAG | GAA | GAA | AAG | GGG | AGG | AAG | ACA | GAG | 1620 |
| ATC | CTG | GAA | GAG | ATA | TGG | GCA | TTT | GGG | GAA | ATA | GTG | TGA | CCA | TGT | 1665 |
| ATC | AGG | CTT | TGT | GGA | CAT | CTA | ACG | AAT | ATG | TCA | TGT | TTT | TGT | AAA | 1710 |
| TAC | AAG | CAT | GCA | CGC | AGA | AAC | AAA | GGG | AGA | AAA | CTG | CTT | TGG | GTG | 1755 |
| TTA | GCA | CTG | TTC | TCT | GTC | CCT | ATA | TAA | TAA | AGA | ATA | CCT | GCT | GAT | 1800 |
| GGC | AAT | GGA | AAA | AAA | AAA | AAA | A | | | | | | | | 1822 |

( 2 ) INFORMATION FOR SEQ ID NO: 7:

( i ) SEQUENCE CHARACTERISTICS:
        ( A ) LENGTH: 3134
        ( B ) TYPE: Nucleic Acid
        ( C ) STRANDEDNESS: Double
        ( D ) TOPOLOGY: Linear ( i i ) MOLECULE TYPE: DNA ( v i ) ORIGINAL SOURCE: Synthetically Prepared ( v i i ) IMMEDIATE SOURCE: Synthetically Prepared ( x i ) SEQUENCE DESCRIPTION: SEQ ID NO: 7:

| ATC | CGC | TCG | AGC | TCT | CTC | CTC | CTA | CAG | TTT | CTG | CCC | TCA | TAT | TCT | 45 |
| CCC | CAC | ACT | TCT | TCC | CCA | TAT | TCT | TTC | CAA | ATC | CTC | TTC | CCC | ATC | 90 |
| TCC | TCC | ATC | GTC | TCC | TTC | TCA | GAG | TCC | TTC | CTC | TCT | CTC | CCT | AAA | 135 |
| TTC | TTC | CCC | CCT | CCT | CTT | CTC | CAG | CAC | AGA | TGG | CCT | TCA | CAT | CGG | 180 |
| GCT | GCA | ACC | ACC | CCA | GTT | TCA | CCC | TCC | CCT | GGA | GGA | CCC | TCC | TGC | 225 |
| CTT | ATC | TCG | TGG | CTC | TGC | ACC | TCC | TCC | AGC | CGG | GAT | CAG | CCC | AGA | 270 |
| TCA | CGG | TGG | TGG | CAC | CGA | GCC | TCC | GTG | TCA | CTG | CCA | TCG | TGG | GAC | 315 |
| AGG | ATG | TTG | TGC | TGC | GCT | GCC | ACT | TGT | CCC | CAT | GCA | AGG | ATG | TTC | 360 |
| GGA | ATT | CAG | ACA | TCA | GAT | GGA | TCC | AGC | AGC | GGT | CCT | CTC | GGC | TTG | 405 |
| TGC | ACC | ACT | ACC | GAA | ATG | GAG | TGG | ACC | TGG | GGC | AGA | TGG | AGG | AAT | 450 |
| ATA | AAG | GGA | GAA | CAG | AAC | TGC | TCA | GGG | ATG | GTC | TCT | CTG | ATG | AA | 495 |
| ACC | TGG | ATT | TGC | GCA | TCA | CTG | CTG | TGA | CCT | CCT | CTG | ATA | GTG | GCT | 540 |
| CCT | ACA | GCT | GTG | CTG | TGC | AAG | ATG | GTG | ATG | CCT | ATG | CAG | AAG | CTG | 585 |
| TGG | TGA | ACC | TGG | AGG | TGT | CAG | ACC | CCT | TTT | CTA | TGA | TCA | TCC | TTT | 630 |
| ACT | GGA | CAG | TGG | CTC | TGG | CTG | TGA | TCA | TCA | CAC | TTC | TGG | TTG | GGT | 675 |

```
CAT TTG TCG TCA ATG TTT TTC TCC ATA GAA AGA AAG TGG CAC AGA    720
GCA GAG AGC TGA GTG AGT CCT TCC ATC CCC ATC CAC CAA CCA AAG    765
TCC CTT TAA TGG AAC TGA CAG CAG ACT GCA GAG TGC TGG GTT ATG    810
CCA TGT GCT GGG GCC ATG AGC TAT GTT GAG GCT TTG GAA TGT GTT    855
GGG GTT GTG GGA TGT ACT GGG GTC GTG GGA TGT GTT ATT CCT GGC    900
TGA TTC ACG TGG AAA AAC CTT TCA CAA TCG GTT CCT TCC AGT TTG    945
TTT AAT TCC TTC TTG GGC CCA AAG TGG TCA TTG GAC TCC TCC CAG    990
AAA AAA GGG TTT GGG GTC AGG GTG TGA GAG CTG ATG GCA CGG AAA   1035
CGT GTC CCC TCT GAC CAT GCA TTT CAT TTG CTT CTA TTT GCA AGA   1080
GAG AAA AGA TGC AGA GTT GGG TAA GTC TCC TTC CCT AAA GCG AGG   1125
GAA TTC AGG GTG TCC CCA TGG CAT CAG CCG TGG AAT TAG TAG CTG   1170
TCC TCT CTG ACA ATT CAC TGC TCT GCT CTT TCC TTT CCA GTG GAG   1215
AAA GCT GCA GCA TTG GGT GAG TTA TAT TCC CCA AGC CAA AGT ACT   1260
TTG GGT CTT CCC ATT GGA AGT TAT TTC CTC AGA CCA TCC TTT CTG   1305
TTG TGT TTG CTT TGG CAT CAT GTT AGT AAA ATG CCT TCT TGG GAC   1350
CAA AGT GGT CAT TGG CCA CTT CCC AGA AAA AAA GGT TTG GGG TCA   1395
GGG TGT GGG AGC TGA TGG CAT GGA AAC ATG TTC CCT CTG ACC ATG   1440
CAT TTC CTT TGC TTC TTT TTC CAG AGA GAA AAG ATG CAG AGT TGG   1485
CGG AAC AAG CAG CGC AAT CGA GTG AGT CTC CCC CTC CAT TTT TAT   1530
TAT TTT TAA ATG TTC AGC CTC CGG TAG CTG TGG GAT GAG ATG TTC   1575
CTC TCA TCA TAC ACT GAC TCT GCT TTT CCT TTG CAG AGC AAA GAG   1620
ATG CAA TGT TGG ACA AAC ACG TTC TAA AAC TGG GTG AGT CCT CAC   1665
TCC CAA ATT ATA AAG CAA AGG GTT CTG CCT GTG TGA GCT GTG GGA   1710
TCA GAC GTT CCT CTC ATC GTG CAT TGC TTT TCT CTT TCT TTT TCA   1755
GAG GAA AAG ACA GAC GAA GTG GAG AAT TGG AAT TCA GTG CTG AGT   1800
AAG TTG CAG TCA CTG AAC TGA GGG AAT GTG GGG TCT TCC TAA GGG   1845
ACT GCG TAG GGG AGA AGT TCC CAT GCA CTG CTT TCT CTT CTT T     1890
TCC AGA AAA AGA CAG TGA AGA GAT GGG TTA TGG CTT TGG AGA TCT   1935
GAG TAA GTC TCC CTC CCA ACA TGG AAG GAA TTT ATG GTC TTA GCA   1980
TGG GAT CAG CCA TGG GAT GAT CAT CTG ACC CCT CTC ATC ATG CAA   2025
TTC ATA TTT GTT CCT TTT GCA GAG AAA CTG GCT GCA GAA CTG GAG   2070
AAA CAC TCT GAA GAG ATG GGG ACA AGG GAT TTA AAG TTG GAG CGA   2115
CTA GCT GCC AAA CTG GAA CAT CAA ACT AAA GAA TTG GAG AAA CAG   2160
CAT TCA CAG TTC AGA GAC ACT TTC AGA ATG TAT TTA AGT GCT       2205
GGA AAA CAG AGT AAG TCT CCC TCC CTG CAC AGA AGG AAC TTA CGG   2250
TTT TCC CAT GGG ATC AGC CAT GGG ACG ATC ATC CGA CTC TTC TCA   2295
TCA TGA ATT TCG TCT TTC TTT CTT TTG CAG AGA AAA TGG TTA CAA   2340
AAC TGG AGG AAC ACT GTG AAT GGA TGG TGA GAA GGA ATG TAA AGT   2385
TGG AGA TAC CAG CTG TAA AAG TGG GGC AAC AAG CTA AAG AAT CAG   2430
AGG AAC AGA AAT CGG AGC TGA AGG AGC ACC ATG AGG AGA CGG GGC   2475
AAC AAG CTA AAG AAT CAG AGA AAC AGA AAT CGG AGC TGA AGG AGC   2520
```

```
GCC ATG AGG AGA TGG CAG AAC AAA CTG AAG CAG TGG TGG TAG AAA      2565
CTG AAG AAT AGG GTG AGT CTT TCC CAA ACC AAA GCA ATA CGG GGT      2610
TTC CCA TGG CAT GAC AAG CTG TCC CAC CTC AGC ATC CGT TCC TTT      2655
TTC TTT CTT TTC CAG AAA AAC CAT CTG AAG AAT TGG ATT GAG AGA      2700
TGA ACT GCG CCT CGC AGT AAC CAC AGG AGT TAA GCT TCA TAG ATC      2745
AAT AAC TGC ACA GCA TAC AAA ACC ACA ATA ACT CAA ACA GGG TAA      2790
GGA GGA GCC AGT GTT TGT GTT GAG TGA GAA CAC TGC AGT TCT GTC      2835
AGC CAA AGC TGC CTG AGG GAC CGC CCA ATT GAG GGT GTG CGA CCT      2880
CCA ACT CAA AGC CAA TTG GAA GAA AGA AAC CAT AGA AAG GAA GAA      2925
AAG GGG AGG AAG ACA GAG ATC CTG GAA GAG ATA TGG GCA TTT GGG      2970
GAA ATA GTG TGA CCA TGT ATC AGG CTT TGT GGA CAT CTA ACG AAT      3015
ATG TCA TGT TTT TGT AAA TAC AAG CAT GCA CGC AGA AAC AAA GGG      3060
AGA AAA CTG CTT TGG GTG TTA GCA CTG TTC TCT GTC CCT ATA TAA      3105
TAA AGA ATA CCT GCT GAT GGC AAA AAA AA                           3134
```

( 2 ) INFORMATION FOR SEQ ID NO: 8:

( i ) SEQUENCE CHARACTERISTICS:
        ( A ) LENGTH: 1449
        ( B ) TYPE: Nucleic Acid
        ( C ) STRANDEDNESS: Double
        ( D ) TOPOLOGY: Linear ( i i ) MOLECULE TYPE: DNA ( v i ) ORIGINAL SOURCE: Synthetically Prepared ( v i i ) IMMEDIATE SOURCE: Synthetically Prepared ( x i ) SEQUENCE DESCRIPTION: SEQ ID NO: 8:

```
CGA TGT TCG GAA TTC AGA CAT CAG ATG GAT CCA GCT GCG GTC CTC       45
TAG GAT TGT GCA CCA CTA CCA AAA TGG AGA GGA CCT GGA TCA GAT       90
GGA GGA ATA TGA AGG GAG AAC AGA ACT GCT CAG GGA TGG TCT CTC      135
TGA TGG AAA CCT GGA TTT GCG CAT CAC TGC TGT GAG CTC CTC TGA      180
CAG TGG CTC GTA CAG CTG TGC TGT GCA AGA TGA TGG CTA TGC          225
AGA AGC TGT GGT GAA CCT GGA GGT GTC AGA TCC CTT TTC CCA GAT      270
CGT CCA TCC CTG GAA GGT GGC TCT GCC TGT GGT CGT CAC AAT TCT      315
CGT TGG GTC ATT TGT CAT CAT TGT TTT TCT CTA TAG GAA GAA AGT      360
GGC ACA GAG CAG AGA GCT GAA GGG AAA AGA TGC AGC ACT GGC GGA      405
ACT ACC TGC GAT ATT GGG TGT ATG TAC TGC AAA TTT GAA GAT CCT      450
AGC TTC AAA ACT GAT GAA ACA AAT GGA AAA ATT GGA GAT TCA GAA      495
TTC ACT CTT GAA GAA ACG GTA TGA GAT TAC GGA GGA ACT GGC TGC      540
AGA TCT GGA GGA ACA TCT TGC TGA GAA GGA TTT AAG CAC TGC AGA      585
TCT GAA GCT ACT AGC TGC AAA ACT GGT GGA ACA AAG AGA AGC AGT      630
GGA GGA ACG GGA TTC ACA GCT GAG GAA ACA GTA TGA AAA GTT GGG      675
TTC GCG TGC TAC AAA TCT GAA GAC ACA ACT AAA AGT TGG AGA A        720
CGA AAT TGA AGA AGT GGA GAA ACA CCT AAA AAG ATG GTA T ACG        765
TGC TCC TAA TCT GAA GCT ACA CAT GGC AGA ACT GGT GGA TCA AGC      810
```

| | | | | | | | | | | | | | | |
|---|---|---|---|---|---|---|---|---|---|---|---|---|---|---|
| TGA | AGC | AGT | GGA | GAA | ACG | GAA | ATC | AGA | GCT | GAA | GAG | CTA | TTT | GAC | 855 |
| AAA | TAT | AGG | TTT | ACG | TGC | TGC | AGA | GCT | GAA | AAA | ATA | CAT | TGC | AGC | 900 |
| ACT | GGA | GAA | ACG | AAT | TGA | AGC | ATT | GGA | AAC | TAA | AGA | ATT | GGA | ACA | 945 |
| ACC | ATC | TAA | AGA | ACA | GGA | TTG | AAA | GAT | GAA | CTG | CGC | CTC | ACA | GTA | 990 |
| ACC | ACA | GGA | GTT | AAG | CTT | CAT | AGA | CTG | CAG | ACT | GCA | CAG | GAT | AGC | 1035 |
| AAC | ATC | GCC | ATA | ACG | CAA | AGC | AAG | CAA | GGA | AAT | CCA | CAC | GGG | GAA | 1080 |
| CAA | GAG | GAG | CCA | GTG | TTT | GTA | TTG | AGT | GAG | AAC | ACT | GCA | GTT | CTG | 1125 |
| CAA | GCC | ACA | GCT | GCC | TGA | GGG | ACC | AGC | AAA | CTG | AGG | GTG | TGT | GAC | 1170 |
| CTC | CAT | CTC | AAA | TCC | AGT | TGG | AAG | AAA | GAC | ACC | ATA | GAA | AAG | AAG | 1215 |
| ACT | ACA | AGA | GGA | AGA | CAG | AGA | TCC | TGG | AAA | AGG | GAC | AGA | CAT | TTT | 1260 |
| GGG | AAT | GAA | CAT | GGC | CAT | GTA | TCA | GGG | TTT | GAG | GAA | TTC | TAA | TGA | 1305 |
| ATA | TGT | AAG | GCT | TCT | GGA | AAT | ATA | AAC | ATG | CAC | ACA | GAA | GTA | AAG | 1350 |
| GTA | GAA | AAC | TGC | TTT | GGG | TGT | TAA | CAC | TGT | TCT | CTA | TCA | CAA | TAT | 1395 |
| AAT | AAA | GAA | ATA | CCT | GCT | GAT | GGC | GAT | GGA | AAA | GAA | AAA | AAA | AAA | 1440 |
| AAA | AAA | AAA | | | | | | | | | | | | | 1449 |

(2) INFORMATION FOR SEQ ID NO: 9:

(i) SEQUENCE CHARACTERISTICS:
        (A) LENGTH: 2217
        (B) TYPE: Nucleic Acid
        (C) STRANDEDNESS: Double
        (D) TOPOLOGY: Linear (ii) MOLECULE TYPE: DNA (vi) ORIGINAL SOURCE: Synthetically Prepared (vii) IMMEDIATE SOURCE: Synthetically Prepared (xi) SEQUENCE DESCRIPTION: SEQ ID NO: 9:

| | | | | | |
|---|---|---|---|---|---|
| GCTCCTTCTG | CATATTCTTC | CTGAACTTTT | TCTAAATCTT | CTTTCCAGAT | 50 |
| CTTCTTCCCC | ATCTGCTCCA | GCACCTCCTC | CTTGTATCCC | CTTCCCCAAT | 100 |
| CTTCCCTTCC | CCACCTCCTT | CTCCTATCAT | CTCTCATCTT | TTACCCATTT | 150 |
| TCTACCCACC | TTCTGCCCCA | TCTCCTCCAT | CATCTCCTTC | TCAGTCTCCT | 200 |
| TCCTCTCTCT | CCTTTCCCCA | ACTCCTCCCC | CCCTCCTCTT | CTCCAGCACA | 250 |

| | | | | | | | | | | | | | |
|---|---|---|---|---|---|---|---|---|---|---|---|---|---|
| | GA | TGC | ACT | TCA | CAT | CGG | GCT | GCA | ACC | ACC | CCA | GTT | TCA | CCC | 291 |
| | | Xaa<br>1 | Xaa | Xaa | Xaa | Xaa<br>5 | Xaa | Xaa | Xaa | Xaa | Xaa<br>10 | Xaa | Xaa | Xaa | |
| TCC | CCT | GGA | GGA | CCC | TCC | TGC | CTT | ATC | TCA | TGG | CTC | TGC | ACC | | 333 |
| Xaa | Xaa | Xaa | Xaa | Xaa | Xaa | Xaa | Xaa | Xaa | Xaa | Xaa | Xaa | Xaa | Xaa | | |
| | 15 | | | | 20 | | | | | 25 | | | | | |
| TCC | TCC | AGC | CGG | GAT | CAG | CCC | AGC | AAA | GGG | TGG | TGG | CAC | CGA | | 375 |
| Xaa | Xaa | Xaa | Xaa | Xaa | Xaa | Xaa | Xaa | Xaa | Xaa | Xaa | Xaa | Xaa | Xaa | | |
| | | 30 | | | | 35 | | | | | 40 | | | | |
| GCC | TCC | GTG | TCA | CTG | CCA | TCG | TGG | GAC | AGG | ATG | TTG | TGC | TGC | | 417 |
| Xaa | Xaa | Xaa | Xaa | Xaa | Xaa | Xaa | Xaa | Xaa | Xaa | Xaa | Xaa | Xaa | Xaa | | |
| | | | 45 | | | | 50 | | | | 55 | | | | |
| GCT | GCC | AGT | TGT | CCC | CTT | GCA | AGG | AAG | CTT | GGA | GAT | CAG | ACA | | 459 |
| Xaa | Xaa | Xaa | Xaa | Xaa | Xaa | Xaa | Xaa | Xaa | Xaa | Xaa | Xaa | Xaa | Xaa | | |
| | | | | 60 | | | | 65 | | | | | | | |
| ACA | GAT | GGA | TCC | AGC | TGC | GGT | CCT | CTC | GGC | TTG | TGC | ACC | ACT | | 501 |
| Xaa | Xaa | Xaa | Xaa | Xaa | Xaa | Xaa | Xaa | Xaa | Xaa | Xaa | Xaa | Xaa | Xaa | | |
| 70 | | | | | 75 | | | | | 80 | | | | | |
| ATC | AAT | ATG | GAT | TGG | ACC | TGG | GGC | AGA | TGG | AGG | AAT | ATA | AAG | | 543 |

|  |  |  |  |  | Xaa 85 | Xaa | Xaa | Xaa | Xaa | Xaa 90 | Xaa | Xaa | Xaa | Xaa 95 | Xaa | Xaa |  |
|---|---|---|---|---|---|---|---|---|---|---|---|---|---|---|---|---|---|

```
GGA GGA CAG AAC TAC TCA GGA AGG GTC TCT CTG ATG GAA ACC           585
Xaa Xaa Xaa Xaa Xaa Xaa Xaa Xaa Xaa Xaa Xaa Xaa Xaa Xaa
        100                 105                 110

TGG ATT TGC GCT TCA CTG CTG TGA GCA CCT CCG ATA ATG GCT           627
Xaa Xaa Xaa Xaa Xaa Xaa Xaa Xaa Xaa Xaa Xaa Xaa Xaa Xaa
        115                 120                 125

CAT ACA GCT GTG CTG TGC AAG ATG ATG ATG GCT ACG GAG ACG           669
Xaa Xaa Xaa Xaa Xaa Xaa Xaa Xaa Xaa Xaa Xaa Xaa Xaa Xaa
        130                 135

CTG TTG TGG AGC TGG AGG TGT CAG ATC CCT TTT CCC AGA TCG           711
Xaa Xaa Xaa Xaa Xaa Xaa Xaa Xaa Xaa Xaa Xaa Xaa Xaa Xaa
140                 145                 150

TCC ATC CCT GGA AGG TGG CTC TGG CTG TGG TTG TCA CAA TTC           753
Xaa Xaa Xaa Xaa Xaa Xaa Xaa Xaa Xaa Xaa Xaa Xaa Xaa Xaa
        155                 160                 165

TGG TTG GGT CAT CTG TCA TCA ATG TTT TTC TCT ATA GAA AGA           795
Xaa Xaa Xaa Xaa Xaa Xaa Xaa Xaa Xaa Xaa Xaa Xaa Xaa Xaa
        170                 175                 180

AAG CTG CAC AGA GCA GAG AGC TGA GTG AGT CCT TCC AGC ACC           837
Xaa Xaa Xaa Xaa Xaa Xaa Xaa Xaa Xaa
        185                 190

TTCCACCACC AAAGTCCCTT TAATGGAACT GATAGAAGAC TGCAGAGTGC            887

TGGGTTTATG CCATGGGCTG GGGCTGTGGG ATCTTTGGGG CTTGGGATGT            937

GTTGGGGCCG TGGGATGTGC TGGGGTCGTG GGATCTGTCA ATCCTGATTG            987

CTCCTCTTCA GAACTCTTGC CCAATCGGTT CCTTCCGATT CATTTAACTC           1037

CTTCTTGGAC CAAAGTGGTC ATTGGCCTCT TACTAGAAAG AAAAGATTTG           1087

GGGTCTGGGT ATGGGAGCAG CCATGGGATG AGAAGGTGTT CCCTCTGACC           1137

ATACATTTCT TTTGCTTCTA TTTTGCA                                    1164

GAG AGA AAA GAT GCA ATG TTG GGT CCC GGT GCT GAA AAG CTG          1206
Xaa Xaa Xaa Xaa Xaa Xaa Xaa Xaa Xaa Xaa Xaa Xaa Xaa Xaa
        195                 200

AAG AAA TTA GCT TCA AAA CTG AAC GAA AAT GCT GAC GAA GTG          1248
Xaa Xaa Xaa Xaa Xaa Xaa Xaa Xaa Xaa Xaa Xaa Xaa Xaa Xaa
205                 210                 215

GAG AAT TGC AAT TTA GAG CTG AAA AAA GAC TGT GAC GAG ATG          1290
Xaa Xaa Xaa Xaa Xaa Xaa Xaa Xaa Xaa Xaa Xaa Xaa Xaa Xaa
        220                 225                 230

AGT TCT GCC GTT GCA GAT CTG AAG AAA TTG GCT GCA GTG ATT          1332
Xaa Xaa Xaa Xaa Xaa Xaa Xaa Xaa Xaa Xaa Xaa Xaa Xaa Xaa
        235                 240                 245

TGG ATA TGG GAT TTA AAG TTG TAT AAT CTA GCT GCC AAA CTG          1374
Xaa Xaa Xaa Xaa Xaa Xaa Xaa Xaa Xaa Xaa Xaa Xaa Xaa Xaa
        250                 255                 260

GGA CAA CAA ACT AAA GAA CTG GAG GAA CAG CAT TCA CAG TTC          1416
Xaa Xaa Xaa Xaa Xaa Xaa Xaa Xaa Xaa Xaa Xaa Xaa Xaa Xaa
        265                 270

CAG GGT CAC TTT CAG CAT ATG GAT TTA AGT GCT GTA AAA CAG          1458
Xaa Xaa Xaa Xaa Xaa Xaa Xaa Xaa Xaa Xaa Xaa Xaa Xaa Xaa
275                 280                 285

AAG AAA CTG GTT ACA AAA CTG GAG GAA CAC TGT AAT CAG ATG          1500
Xaa Xaa Xaa Xaa Xaa Xaa Xaa Xaa Xaa Xaa Xaa Xaa Xaa Xaa
        290                 295                 300

GTG AGA AGG AAT GTA AAG TTG GAG GCA GCA GCT GTA AAA CTG          1542
Xaa Xaa Xaa Xaa Xaa Xaa Xaa Xaa Xaa Xaa Xaa Xaa Xaa Xaa
        305                 310                 315

GGG CAA CAA GCT AAA GAA TCA GAG GAA CAG AAA TCG GAG CTG          1584

| Xaa | Xaa | Xaa | Xaa 320 | Xaa | Xaa | Xaa | Xaa | Xaa 325 | Xaa | Xaa | Xaa | Xaa | Xaa 330 | | |
|---|---|---|---|---|---|---|---|---|---|---|---|---|---|---|---|

AAG GAG CGC CAT GAG GAG ATG GCA GAA CAA ACT GAA GCA GTG        1626
Xaa Xaa Xaa Xaa     Xaa Xaa Xaa Xaa     Xaa Xaa Xaa Xaa
            335                 340

GTG GTA GAT ACT GAA GAA TAG GGT GAG TCT TCC CCA AAC CAA        1668
Xaa Xaa Xaa Xaa Xaa Xaa
345             350

AGCAATACGG GGTTTCCCAT GGCATGACAA GCTGTCCCAC CTCAGCATCC         1718

GTTGCTTTTT ATTTCTTTTC CAGAAAAACC ATCTGAAGAA TTGGATTGAG         1768

AGATGAACTG CGCCTCACAG TAACCACAGG AGTTAAGCTT CATAGATCAA         1818

TTACTACACA GCATAAAAAA CCACGATTCC ACAAACAGAG CAAGGAAATC         1868

CACAGCGAGA ACAAGAGGAG CCAGTGTTTG TGTTGAGTGA AACACTGCA          1918

GTTCTGTGAG CCAAAGCTGC CTGAGGGACC GCCGAACTGA GGGTGTGCGA         1968

CCTCCAACTC AAAGCAATTG GAAGAAGAA ACCATAGAAA GGAAGGAAAG          2018

GGGAGGAAGA CAGAGATCCT GGAAGAGATA TGGGCATTTG GGGAAATAGT         2068

GTGACCATGT ATCAGGCTTT GTGGACATCT AATGAGTATG TAATGCTTAT         2118

GGAAGTAGAA GCATGCACGC AGAAACAAAG GTAGAAAACT GCTTTGGGTG         2168

TTAACACTGT TCTCTGTCAC TATATAATAA AGAATACCTG CTGATGGCA          2217

( 2 ) INFORMATION FOR SEQ ID NO: 10:

( i ) SEQUENCE CHARACTERISTICS:
        ( A ) LENGTH: 2188
        ( B ) TYPE: Nucleic Acid
        ( C ) STRANDEDNESS: Double
        ( D ) TOPOLOGY: Linear ( i i ) MOLECULE TYPE: DNA ( v i ) ORIGINAL SOURCE: Synthetically Prepared ( v i i ) IMMEDIATE SOURCE: Synthetically Prepared ( x i ) SEQUENCE DESCRIPTION: SEQ ID NO: 10:

AAAGGAGTGA GTTGTGTACA GGGGGGTTAA ATGCTTTATA GACAAGAAAG           50

AAATTGCTCT AAAAGAGACT TATTCATCAT CATCATCATC TTCCTCCTCC          100

TCTTCTTCCT CTTCTTCGTC CTCTTCATCC TCTTCGTCTT CGTCCTCATC          150

TTCCTCTTCT TCCTTCTTCT TCTTGCTCTT CTCGGCCTTG GCAACTACTT          200

TTTTGCCTGC ATCAACTTC CCTTTGGCCC GGTATGCAGC GATATCCTTC           250

TCAGTCTCCT TCCTCTCTCT CCTTGGCCCA ACTCCTCCCC CCTCCTCTTC          300

TCCAGCACAG ATGGCCTTCA CATCGAGCTG CAACCACCCC AGTTTCACCC          350

TCCCCTGGAG GACCCTCCTG CCTTATCTCG TGGCTCTGCA CCACCTCCAG          400

CCGGGATCAG CCCAGCTCAG GGTGGTGGCA CCGAGCCTCC GTGTCACTGC          450

CATTGTGGGA CAGGACGTCG TCTGCGCTGT CACTTGTCTC CTTGCAAGAA          500

TGCTTGGAAT TCAGACATCA GATGGATCCA GCACCGTTCC TCTAGGATTG          550

TGCACCACTA CCAAGACGGA GTGGACCTGG AGCAGATGGA GGAATATAAA          600

GGGAGGACAG AACTGCTCAG GGATGGTCTC TCTGATGGAA ACCTGGATTT          650

GCGCATCACT GCTGTGAGCA CCTCTGATAG TGGCTCATAC AGCTGTGCTG          700

TGCAGGATGA TGATGGCTAT GCAGAAGCTT TGGTGGAGCT GGAGGTGTCA          750

GATCCCTTTT CCCAGATCGT CCATCCCTGG AAGGTGGCTC TGGCTGTGAT          800

| | | | | | |
|---|---|---|---|---|---|
| CGTCACAATT | CTGGTTGGGT | CATCGGTCAT | CATTGTTTTT | CTCTGTAGAA | 850 |
| AGAAAGAGAG | AAAAGATGGA | GAGTTGGCGG | AACAAGCTGA | AATACTGGAG | 900 |
| AGAAAAGATG | CAATGTTGAC | GGAACAAGCT | GAAACACTGG | AGAAAAAAGA | 950 |
| TGTAATGTTG | AAGGAACAAG | CTATGATAGC | GGAATCAAAT | GCTGAAGATC | 1000 |
| TGAAGAAACT | GGCTGCGAAA | CTGGAGAAAC | ACTCTGAAGA | GATGGGGACA | 1050 |
| AGGGATTTAA | AGTTGGATAA | ATTAGCTGCC | AAACTGGAAC | ATCAAACTAA | 1100 |
| AGAATTGGAG | AAACAGAAAT | CGGAGCTGAA | GAGTCACTTT | CAGTATATGG | 1150 |
| ATTTCAATGC | TGGAAAACAG | AAGAAAATGG | TTACAAAACT | GGAGGAACAC | 1200 |
| TATGAATGGA | TGGTGACAAG | GAATGTAAAA | TTGGAGATAC | CAGCTATAAA | 1250 |
| AGTGGGGCAA | CAAGCTAAAG | AATCAGAGGA | ACAGAAATCG | GAGCTGAAGG | 1300 |
| AGCACCATGA | GGAGATGGGG | CAACAAGCTA | AGAATCAGA | GGAACAGAAA | 1350 |
| TCGGAGCTGA | AGGAGCACCA | TGAGGAGATG | GGCAACAAG | CTAAAGAATC | 1400 |
| AGAGGAACAG | AAATCGGAGC | TGAAGGAGCA | CCATGAGGAG | ATGGGGCAAC | 1450 |
| AAGCTAAAGA | ATCAGAGGAA | CAGAAATCGG | AGCTGAAGGA | GCACCATGAG | 1500 |
| GAGATGGGGC | AACAAGCTAA | AGAATCAGAG | AACAGAAAT | CGGAGCTGAA | 1550 |
| GGAGCACCAT | GAGGAGATGG | GGCAACAAGC | TAAAGAATCA | GAGGAACAGA | 1600 |
| AATCGGAGCT | GAAGGAGCAC | CATGAGGAGA | TGGGGCAACA | AGCTAAAGAA | 1650 |
| TCAGAGGAAC | AGAAATCGGA | GCTGATGGTA | GAAACTGAAG | AAGCAGAAAA | 1700 |
| ACCATCTGAA | GAATCAGATT | GAGAGATGAA | CTGCGCCTCC | AATAAGCAC | 1750 |
| AGGAGTTAAG | CTTCATAGAT | CAATGACTGT | ACAGCAAACA | AAAACCACGA | 1800 |
| TAACTCAAAC | AGAGCAAGGA | AATCCACAGC | GAGAACAAGA | AGAGCCAGTG | 1850 |
| TTTGTGTTGA | GTGAGAACAC | TGCAGTTCTG | TCAGCCAAAG | CTGTCTGAGG | 1900 |
| GACCGCCAAA | TTGAGGGTGT | CGAACCTCCA | ACTCAAAGCC | AATTGGAAGA | 1950 |
| AAGAAACCAT | AGAAAGGAAG | AAAAGGGGAG | GGAGACAGAG | ATCCTGGAAA | 2000 |
| AGATATGGGC | ATTTGGGGAA | ATAGTGTGAC | CATGTATCAG | GCTTTATGGA | 2050 |
| AATCTAACAA | ATATGTCATG | GTTTTGTAAA | TACAAGCATG | CACGCAGAAA | 2100 |
| CAAAGGTAGA | AAACTGCTTT | GGGTGTTAGC | ACTGTTCTCT | GTCCCTATAT | 2150 |
| AATAAAGAAT | ACCTGCTGAT | GGCAAAAAAA | AAAAAAAA | | 2188 |

( 2 ) INFORMATION FOR SEQ ID NO: 11:

( i ) SEQUENCE CHARACTERISTICS:
    ( A ) LENGTH: 1487
    ( B ) TYPE: Nucleic Acid
    ( C ) STRANDEDNESS: Double
    ( D ) TOPOLOGY: Linear ( i i ) MOLECULE TYPE: DNA ( v i ) ORIGINAL SOURCE: Synthetically Prepared ( v i i ) IMMEDIATE SOURCE: Synthetically Prepared ( x i ) SEQUENCE DESCRIPTION: SEQ ID NO: 11:

| | | | | | |
|---|---|---|---|---|---|
| TTGCAAGAAT | GCTTGGAGCT | TAGATATCAG | ATGGATCCAG | CTGCGGTCCT | 50 |
| CTGGTTTTGT | GCACCACTAC | CGAAATGGAG | AGGACCTGGA | GCAGATGACA | 100 |
| GAATATAAAG | GGAGAACAGA | ACTGCTCAGG | AAGGGTCTTT | CTGATGGAAA | 150 |
| CCTGGATTTG | CGCATCACTG | CTGTGAGCAC | CTCCGATAGT | GGCTCATACA | 200 |
| GCTGTGTTGT | GCAAGACGAT | GATGGCTATG | CAGAAGCGTT | GGTGGAGCTG | 250 |

| | | | | |
|---|---|---|---|---|
| GAGGTGTCAG | ATCCCTTTTC | CCAGATCGTC | CATCCCTGGA | AGGTGGCTCT | 300
| GGCTGTGATC | GTCACAATTC | TGGTTGGGTC | ATTTGTCATC | ATTGCTTTTC | 350
| TCTATAGGAA | GAAAGCGACA | CAGAGCAGAG | AGCTGAAAAG | AAAAGATGCA | 400
| ATGTTGGGAA | GAAAAGATGC | AGTGCTGGAG | GAACTACCTG | CGATATTAGA | 450
| TTCAAGTGCT | GCAAATCTGA | AGATACTAGC | TTCAAAACTG | GTGAAACAAA | 500
| CTGAAAAATT | GGACATACGG | AATTCACTAA | TGAAGAAACA | GTATGAAATG | 550
| ACAGAGAAAC | AAGCTGCAGA | ACTGGAGAAA | CACTTAATAA | ATACCGATTT | 600
| AAGTGCTGCA | GATCTGAAGA | TAGCAGCTGC | AAAACTGGAC | AAACAAACTG | 650
| AAGAACTGGA | CAAATGGAAA | TCAGCACTGA | AGATACAATA | TGAAAAGTTG | 700
| GGTTTACGTG | CTGCAAATCT | GAAGACACAA | GTTACAGAAC | TGGCGAAACA | 750
| AACTGAAGAA | GTGGAAAATC | ACTATGAAGA | GATGGGTTTA | CGTGCTCCTA | 800
| ATCTGAAGAA | AAATATAGTA | GAACTGGAGA | AACAAACTGA | GCACGTGGAC | 850
| AATCGGAAAT | CAGAGCTGAA | GAAACAGTAT | GAAAATTTGG | CTTCACATGC | 900
| TTCAGAGCTG | AAGAAACAAG | CTGAAGTACT | GGAGGAACAA | GCTGAACAAC | 950
| TGGAGATTCA | GAATTCACTG | TTGAAGATAC | GCAATAAACA | TAGGGAGAGA | 1000
| AAGAATGAAA | TGTTGGAGAA | ACAAACTGTA | GAACAGGAAC | AAACTGAAGA | 1050
| ATGGGCAGAA | TCTAAAAAAT | CGGTGGTTGA | AACTAAAGAA | TTGGAACAAC | 1100
| CATCTAAAGA | ACAGGATTGA | GAGATGAACT | GCGCCTCACA | GTAACCACAG | 1150
| GAGTTAAGCT | TCATGGACTG | CTGACTGCAC | AGGATAGCAA | CACCGCCATA | 1200
| ATGCAAAGCG | AGCAAGGAAA | TCCACAGCGA | AAACAAGAGG | AGCCAGTGTT | 1250
| TGTGTTGAGT | GAGAACACTG | CAGTTCCATG | AGCCAAACCT | GCCTGAGGGA | 1300
| CCGCCCAATT | GAGGGTGTGC | GACCTCCAAC | TCAAAGCCAA | TTGGAAGAAA | 1350
| GAAACCATAG | AAAGGAAGAC | TACAAGAGGA | AGACAGAGAT | CCTGGAAAAG | 1400
| GGATAGACAT | TTTGGGATTT | AACATGGCCA | TGTATCAGGG | TTTGAGGAAT | 1450
| TCTAACGTAT | ATATAAGGCT | TTTGGAAATA | TAAACAT | | 1487

( 2 ) INFORMATION FOR SEQ ID NO: 12:

( i ) SEQUENCE CHARACTERISTICS:
        ( A ) LENGTH: 4757
        ( B ) TYPE: Nucleic Acid
        ( C ) STRANDEDNESS: Double
        ( D ) TOPOLOGY: Linear ( i i ) MOLECULE TYPE: DNA ( v i ) ORIGINAL SOURCE: Synthetically Prepared ( v i i ) IMMEDIATE SOURCE: Synthetically Prepared ( x i ) SEQUENCE DESCRIPTION: SEQ ID NO: 12:

| | | | | |
|---|---|---|---|---|
| GGATGATCAT | CCGACTCTTC | TCATCATAAA | TTCGTCTTCT | TCTTTGCAGA | 50
| GAAACTGGTT | ACAAAACTGG | GTGAGTCCAA | CCTCCCAAAC | TAAATTAAAA | 100
| GCAGTCAGAC | TTTGTGAGCT | GTGGGATGAG | ACGTTCTTCT | CATCATGTGC | 150
| TGCTTTCCTT | TTACTTTTCC | AGAGGAACAC | TTTGAATGGA | TGGGTGAGTC | 200
| TCCCCTCCCA | AATTAAAAAT | GTTGGGGTCT | TCCTGTGTGA | GCTGTGGGAT | 250
| GAGCTGTTCC | TCCCATCATG | CACTGGTTCT | AATTTCCTT | TGCAGAGAGA | 300
| AGGAATGTAA | AGTTGGGTGA | GTCTTCTTCC | CCAACCAAAG | GGATTTGGGG | 350

-continued

| | | | | | |
|---|---|---|---|---|---|
| TCTTCCATGG | GATCAGCCAT | GGGATGATAA | CCTGAACCTT | ATCACATATT | 400 |
| TCTTATTTGT | TCTTTTTGCA | GAGATACCAG | ATCTGTAATA | CTGGGTGAGT | 450 |
| CCTCCCTCCC | AAATTAAATA | CAAAGGGGA | TCTGCCTGTG | TGAGCTGTGG | 500 |
| GATGAGATGT | TCCTCTCATC | ACGCATTATT | TTCTCTTTCT | TTTCCAGGGC | 550 |
| AACAAGCTAA | AGAATCAGGT | GAGTCTTCTT | CCCTGTCCCA | AAGGACTATG | 600 |
| GGTTTCCCAT | GGGATGACAA | GCTGTGCCAC | CTCCTCACGA | GGTGCTTCTT | 650 |
| CTTTCTTTTT | TGCAGAGAAA | CAGAAATCGG | AGCTGAGTAA | GTTGCAGTCA | 700 |
| CTGAACTGAG | GGAATGTGGG | GTCTTCCCAA | AGTCTTGTGT | ATGGGATGAA | 750 |
| AAATCCCCTC | TGACCATGCA | CTGCTTTTCT | CCTCCTTTGC | CAGAGGAGCG | 800 |
| CCATGAGGAG | ATGGGTGAGT | CTCCCTCCC | ATATTAAAAT | CGTTGGGGTC | 850 |
| TTCCTGTGTG | AGCTGTGAGA | TGAGATGTTC | CTCTCATCAT | GCGATGCTTT | 900 |
| TCTCTCTTTT | CCAGCAGAAC | AAACTGAAGC | AGTGGGTGAG | TCTTTGTCCC | 950 |
| CAACCCAAAG | GAATATGGGG | CAATCCATGG | GATGACAAGC | TGTCCCATCT | 1000 |
| CATCGTGCAT | TGCTTTCCTA | TTCCTTTTTT | CTAGTGGTAG | ATACTGAAGA | 1050 |
| AGCGGGTGAG | TCTTTCCCAA | ACCAAAGCAA | TACGGGGTTT | CCCATGGCAT | 1100 |
| GACAAGCTGT | CCCACCTCAG | CATCCGTTGT | TTTTCTCTTT | CTTTTCCAGA | 1150 |
| AAAACCATCT | GAAGAATTGG | ATTGAGAGAT | GAACTGCGCC | TCACAGTAAC | 1200 |
| CACAGGAGTT | AAGCTTCATA | GATCAATGAC | TGCACAGCAT | ACAAAAACCA | 1250 |
| CGATACCTCA | AACAGAGCAA | GGAAATCCAC | AGCGAGAACA | AGAGGAGCCA | 1300 |
| GTGTTTGTGT | TGAGTGAGAA | CACTGCAGTT | CTGTCAGCCA | AAGCTGCCTG | 1350 |
| AGGGACCGCC | AAACTGAGGG | TGTGCGACCT | CCAACTCAAA | GCCAATTGGA | 1400 |
| AGAAAGAAAC | CATAGAAAGG | AAGGAAGGG | GAGGAAGACA | GAGATCCTGG | 1450 |
| AAGAGATATG | GGCATTTGGG | GAAATAGTGT | GACCATGTAT | CAGGCTGTGT | 1500 |
| GGACATCTAA | CGAATATGTC | ATGTTTTGT | AAATACAAGC | ATGCACTCAG | 1550 |
| AAACAAAGGT | AGAAAACTGC | TTTGGGTGGT | AACACTGTTC | TCTGTCAAAA | 1600 |
| TATAATAAAG | AATACCTGCT | GATGGTAATG | GATCATTGAT | TGTGAGCAGT | 1650 |
| TATTGGGGTT | TGGTTCCATG | AAACAGGCTG | AGTCTTCTTC | CCAGAAACAA | 1700 |
| AGCAACGTGG | GCTCTATCGG | ATAACAAGCC | GACCCTTCTC | ACCATGCACT | 1750 |
| GCTATTCCAG | CACAACAAGG | CTCTCTCCAG | GAAGCTAAAA | AGGGATAAAA | 1800 |
| TAAATTAATA | GGAAAGAAAT | ACACAAAAAC | AAGAAAATTT | AAAAAGAAT | 1850 |
| ACTCCAAAAA | ATCTATAATT | ATTACAATAA | AAACTTTAAA | AAAACACACC | 1900 |
| AACCTTCCAC | CCTGGGGGAG | CACCAATGAC | AGCCTTTTGT | GCCCCATCGC | 1950 |
| GGTTTTATGA | GAACAGCCAC | ACACTTCAGA | GCTGACCCCG | TGAGCCCCAC | 2000 |
| AGTGGGGGGA | CCTCCCACAG | TGGGTGGACC | TCCTCCACAA | CCACCCCCAT | 2050 |
| CACTCACATT | GAATGCCCAA | AGAAACAACA | GCCCAAAGG | TTCCTCCTGG | 2100 |
| TGCTTCAGCC | GCGTGTGTTC | CTCATTCTGC | TGTGCTGATG | GTGATCATTA | 2150 |
| ACCCAACAGC | TCATTAACCA | GGTTATGGCT | CAGGTGCGTG | CTGCTGAACA | 2200 |
| AGCTTGGAGC | CTAAAATGGT | TCCTGCACAC | ATCCCAGGGG | ACGGCCCTCC | 2250 |
| ACCTTTCACT | CCCCGCCATT | ACAGCTCTCC | TTAATCAGAG | GAATACAGAT | 2300 |
| TCCATGCACT | GAGTGCACTG | AGCCATCGCC | CACCTTCCCT | ACAAACACCT | 2350 |
| CCTGGTCCCC | ACAAACCCTC | ACTGTGGGAA | GAGGGGCTCT | GGGGGGGTCA | 2400 |

| | | | | | |
|---|---|---|---|---|---|
| CAGGGACAAA | CATTTAATAA | TTCCTGTATT | AATGGTTGAT | TAACTTAAAA | 2450 |
| ATCTGTACTG | ATCAAATAAA | CTGCCACCCC | TTGGGCATAG | CTCAGAGCAT | 2500 |
| GCTCATGGAG | TACAGCCCAC | AGCTTTCCTC | TGTGCTAGGG | CAATGCTTCT | 2550 |
| CCTGGGTCCA | TGTTCATCCT | GGGTGGATGC | AGAGCCCAG | GGTGGTACAT | 2600 |
| GAAACTGCAA | TGGGATGTCA | GTGTTCAGAG | TTCTCCAACC | GTCTGCCCCA | 2650 |
| TTGCCAAAGG | GGTAAAGTTC | CTCGGAGCAG | ATTACCACAC | CTGGAGCTG | 2700 |
| GGCAAAGGTT | GACGCTGGGC | AAAGGTAGAA | GCTGGGCATA | GCTGCACGTT | 2750 |
| TCCTGCAGCT | CAGGTGAGGG | ATTTCTGTCT | CTGTGGGCT | CCTTGTAGGG | 2800 |
| GAAATCCTTG | GGGGGTCATC | TGCTCTGCCT | CACAGCCTGT | GAGGAGCACT | 2850 |
| GGCACTGCCC | AAGGCAGTGG | TGGCTGTGCT | CATGGAACTG | ATGTTTGAGT | 2900 |
| GACCCCATCC | CCTCCTCTCC | TGGTGGCTGT | AACCCTCTGG | CCCCTCTCCT | 2950 |
| CCTACAGCTC | CTTCCTGCAT | ATTCTTCCTC | AACTTTTCT | AAATCTTCTT | 3000 |
| TCCAAATCTT | CTACCCCATC | TGCTCCAGCA | CCTCCTTCTC | CATCTCCTTC | 3050 |
| CCCAAACTCC | TCCTTATATC | CCCTTCCCCA | ATCTCCTTCA | CCCACCTCCT | 3100 |
| TCTCCTATCA | TCTTCTCTCA | TCTTTTACCA | TTTTCTACCC | ACCTTCTGCC | 3150 |
| CCATCTCCTC | CATCATATCC | TTCTCAGTCT | CCTTCCTCTC | TCTCCTTTCC | 3200 |
| CCAACTCCTT | CCCCCCTCCT | CTTCTCCAGC | ACAGATGGCC | TTCACATCGA | 3250 |
| GCTGCAACCA | CCCCAGTTTC | ACCCTCCCCT | GGAGGACCCT | CCTGCCTTAT | 3300 |
| CTCGTGGCTC | TGCACCACCT | CCAGCCGGGA | TCAGGTAGGG | GTCCTGTGGG | 3350 |
| GCTGCTGTGC | CTGGCACACG | TGTTGCTATG | GGTGGGGGA | GCCGCCATGG | 3400 |
| GGCAGGGAGG | ACACAAGTCC | AGCCCCCAGC | CCCACTTGGG | TTTCACTTTC | 3450 |
| ACTTTGGTAA | TTCCATGATA | GATGCCATTT | TGGGTAGAAT | TTCTGTCTCT | 3500 |
| TCTTCACCTC | TGCCACACGG | TGTGAGTGGG | CTCCCACCCC | CAGCAATCCT | 3550 |
| TCCCCCTCTC | TCCTGATCCC | TCCCCACTGC | TTTTACACCA | GATGGAGCAC | 3600 |
| ACACCAACTC | ACCCTGTGCC | GCTCCATGCC | CCCACATTAA | CACAGACACC | 3650 |
| ATCTCACCAT | CTCTCCGTGC | CCTTCGCATT | GCCCAGCCCA | GCTCAGGGTG | 3700 |
| GTGGCACCGA | GCCTCCGTGT | CACTGCCATT | GTGGGACAGG | ACGTCGTCTG | 3750 |
| CGCTGTCACT | TGTCTCCTTG | CAAGAATGCT | TGGAATTCAG | ACATCAGATG | 3800 |
| GATCCAGCAC | CGTTCCTCTA | GGATTGTGCA | CCACTACCAA | GACGGAGTGG | 3850 |
| ACCTGGAGCA | GATGGAGGAA | TATAAAGGGA | GGACAGAACT | GCTCAGGGAT | 3900 |
| GGTCTCTCTG | ATGGAAACCT | GGATTTGCGC | ATCACTGCTG | TGAGCACCTC | 3950 |
| TGATAGTGGC | TCATACAGCT | GTGCTGTGCA | GGATGATGAT | GGCTATGCAG | 4000 |
| AAGCTTTGGT | GGAGCTGGAG | GTGTCAGGTC | AGTGGCTGGG | GTGACGTCTC | 4050 |
| CAGGTGTCCC | TGGGTTTGTG | GGTCCCACCC | AACCTCTGTC | CATCCTCATC | 4100 |
| CTCACGTCCA | TGGATGGAGA | GCTGAAGGAC | AGCAGCCTTT | GGAAGAGGTC | 4150 |
| AGGGCTGAAT | TGTTTTATGA | GATGCTGGAA | TTAGAGCGGA | CACACGGTGT | 4200 |
| GATTTGGGGA | ATAGACTGCA | TGGATGAGGT | GGTTGGGTTG | GATTTCTGGG | 4250 |
| ATGGGTTTCT | CCATGTATCA | GTGGCAGTGG | GCACACGATG | CTGAGCAGCT | 4300 |
| CCTCCGCCTG | TGCCAATATG | GGGACGCTGC | CATTGTGTGT | CACTGTTCCC | 4350 |
| TGCTCACTGC | TCCTTCTGAA | CAGGTGAATT | CCGTTACCTT | TTCCTTGGGA | 4400 |
| ACAGGACTAC | AAAAAAGGTC | TAGGGAAAAG | GGTCTAGCAG | GTAGGGACCT | 4450 |

| | | | | | |
|---|---|---|---|---|---|
| TCCACCGAGA | CCGACACTAG | CAGTGTTAAG | ACCAACCCAG | TAGCCAGTAG | 4500 |
| TAACAAAAAG | AGACATCTTT | CTTTCCACTC | AACTCGTACC | TCCCCTACCT | 4550 |
| CGTGTCCTTC | CACAACACGT | ACCTGTCCTT | ACCAGCCCCA | CCACGACTCG | 4600 |
| AGTCCAGGTG | TCTCCATGTG | TCCTCCTGCT | TCCCTCTAAA | AAGGACTCTA | 4650 |
| AGGGTCACGA | GTAATTTATT | GAAAAGGGAA | AGAAAAACCC | TTACTTCCTT | 4700 |
| CCTTTTTTTC | CCCACACCCA | CCCTTCTATC | CTTACACCGA | CATCCGTCCA | 4750 |
| CCTTTCA | | | | | 4757 |

(2) INFORMATION FOR SEQ ID NO: 13:

(i) SEQUENCE CHARACTERISTICS:
(A) LENGTH: 105
(B) TYPE: Nucleic Acid
(C) STRANDEDNESS: Double
(D) TOPOLOGY: Linear (ii) MOLECULE TYPE: DNA (vi) ORIGINAL SOURCE: Synthetically Prepared (vii) IMMEDIATE SOURCE: Synthetically Prepared (xi) SEQUENCE DESCRIPTION: SEQ ID NO: 13:

| | | | | | |
|---|---|---|---|---|---|
| NAVKVGNNAK | NSNNNKSNNA | VKNGNNAKNS | GKNKSANAVN | NGNNAKNSNN | 50 |
| NKSNNMGTRD | NKNNRNAAKN | NNSGVADNKN | NASNNYDNGS | GVADNKNAAK | 100 |
| NNYNA | | | | | 105 |

(2) INFORMATION FOR SEQ ID NO: 14:

(i) SEQUENCE CHARACTERISTICS:
(A) LENGTH: 7350
(B) TYPE: Nucleic Acid
(C) STRANDEDNESS: Double
(D) TOPOLOGY: Linear (ii) MOLECULE TYPE: DNA (vi) ORIGINAL SOURCE: Synthetically Prepared (vii) IMMEDIATE SOURCE: Synthetically Prepared (xi) SEQUENCE DESCRIPTION: SEQ ID NO: 14:

| | | | | | |
|---|---|---|---|---|---|
| CTGGGTCAGA | TCTCCCGGCT | TCATTTCTCT | CCATCCCTGG | GGTCCCCTCC | 50 |
| TCCCGTCTGA | CTGCTGGAGG | GCGGATGATC | ACCCCCTGTC | TGCACCCCTC | 100 |
| CCTGCGCTAT | CTGCAGCCCT | TCAGATGCAC | CGCACCCCAT | TTGCACTCCC | 150 |
| TGCCCCCCCT | TTGTACACAT | GGGGGGGATA | TCAGCCCTCC | TCCTTCCACC | 200 |
| CACCCGTATC | AGAGCCGCTG | TGCTGCTGAG | GGAGGCGGAT | GGGACGGCTG | 250 |
| CATCGCTCCC | CCTCAGCTTC | ACAGAGCTGC | TTTGCTGCGG | GTTTTGGCTG | 300 |
| CAATTCGGAC | CCTCTAAGAA | TGATCCCTCG | TTGTGAGACT | CCGCTGCAAA | 350 |
| GCTGATCCGT | TCGAGCTCTC | CTCCTACAGC | TGCTGCCCTC | ATATTCTCCC | 400 |
| CACACTTCTT | CCCCATATTC | TTTCCAAATC | CTCTTCCCCA | TCTCCTCCAC | 450 |
| CGTCTCTTTC | TCAGAGTCCT | TCCTCTCTCT | CCCTAAATTC | TTCCCCCCTC | 500 |
| CTCTCCTCCA | GCACAGATGC | GCTTCACATC | GGGATGCAAC | CACCCCAGTT | 550 |
| TCACCCTCCC | CTGGAGGACC | CTCCTGCCTT | ATCTCGTGGC | TCTGCACCTC | 600 |
| CTCCAGCCGG | GATCAGGTAG | GGGTCCTGTG | GGGCTGCTGT | GCCTGGCACA | 650 |
| GGTGTTGCTG | TGGGGTGGGG | GAGCAGCCAT | GGGGCAGGGA | GGACCCATGT | 700 |

```
CCAGCACCCA GCCTCGCTTG GGTTTCTCTT TCACTTGGGC TATTTCATGA        750
AATGTGTGAT TTCGGGTGGA ATTTCTGTCC CTTCTTCACC TCCACCACAC        800
GGTGTGAGTG GGCTCCCACC CCCAGCAATC CTTGCCCACT CCCTCCTGAT        850
CCCTCCCCAC TGCTTTTACA TGGGATGGAG CACACACCAA CTAACCCTGT        900
GCCGCTCCAT GCCCCCACAT TAACACAGCC ACCATCTCAC CATCTCTTCG        950
TGCCCTTCTC ATTGCCCAGC CCAGCTCAGG GTGGTGGCGC CGAGCCTCCG       1000
TGTCACTGCC ATCGTGGGAC AGGATGTCGT GCTGCGCTGC CACTTGTGCC       1050
CTTGCAAGGA TGCTTGGAGA TTGGACATCA GATGGATCCT GCAGCGGTCC       1100
TCTGGTTTTG TGCACCACTA TCAAAATGGA GTGGACCTGG GCAGATGGA        1150
GGAATATAAA GGGAGAACAG AACTGCTCAG GATGGTCTC TATGATGGAA        1200
ACCTGGATTT GCGCATCACT GCTGTGAGCA CCTCCGATAG TGGCTCATAC       1250
AGCTGTGCTG TGCAGGATGG TGATGGCTAT GCAGACGCTG TGGTGGACCT       1300
GGAGGTGTCA GGTCAGTGGC TGGGGTGATG TCTCCAGGTG TCCCTGGGCT       1350
TGTGTGTCCC CTACCGACCT CTGTCCATCC TCATCCTCAC ATCCTAGGAT       1400
GGAGAACTGA AGGACAGCAG CCTTTGGAAG AGCTCAGGGC TGAACAGCTC       1450
CATGAGATGC TGGAGTTGGA TCGGGCACAT GGTGTAATTT GAAAATGGAT       1500
ATGCATGGAT GAGGTGGTTG GGTTGGGTTT CTGGGATGGG TTTCTCCACG       1550
TCTCAGTGGC AGTGGGCACA CGATGCTGAG CAGCTCCTCC GCCTGTGCCA       1600
ATATGGGGAC GCTGCCATTG TGTGTCACTG CTCCCTGGTT GTTGTCCCTT       1650
CGGGTTCTGT GATCTCCAGA AGTCGAAGTC GTGTTTGTCC ACATAAGGCA       1700
GTGGAAAAAG GAACCCTTGT CCTGATGTCT TTTCCAGATC CCTTTTCCCA       1750
GATCGTCCAT CCCTGGAAGG TGGCTCTGGC TGTGGTCGTC ACAATTCTCG       1800
TTGGGTCATT TGTCATCAAT GTTTTTCTCT GTAGGAAGAA AGGTGAGCTG       1850
AGAGCGGAGG GGATGGAGCA CAGGGAGGTG TTGTGCATGG ACAGGGATGG       1900
TCGGGGTGGT GCTGAGCTCT GGTGTACAGA GGTACACAGG AGGAGAAAGG       1950
GAGATTTTTC CTGACATTCC CACTGCCCAT TAAATAACAT TGCCTTTCTT       2000
TTGGGGAAAT GAAGGAGGAA AAAAGAAGT GTGGGTGGGC AGATAGGAAA        2050
GTGGGTGGAC CGTGGGGCAG GTGGAAAGGT CCAGACCTCG GACGTCCCC        2100
AAACCAAGCT GCCCTGCTGA CTACCTCTTC CTCCAATTTG TTTTCCAGCG       2150
GCACAGAGCA GAGAGCTGAG TGAGTCCTTC CAGCCCCTTC CACCACCAAA       2200
GTCCCTTTAA TGGAACTGAT AGAAGACTGC AGAGTGCTGG GTTTATGCCT       2250
TGTGCTGGGG CCATGGGATC TATGGGACCT TGGGATGTGT TGGGGCCGTG       2300
GGATGTGCTG GGTCGTGGG ATCTGTCAAC CCTGATTGAT CCACTTCAGA        2350
ACTCTTGCCC AATCGGTTCC TTCCGATTCA TTTAACTCCT TCTTGAGGCC       2400
AAAGTGGTCA TTGGCCACAT CCCAGAAAAA AGGGTTTGGG GTCAGGGTGT       2450
GGGAGCTGAT CGCATGGAAA CGTGTCCCCT CTGACCATGC ATTTCATTTG       2500
CTTCTATTTT GCAGAGAGAA AACATGCAGC GTTGGGTAAG TCTCCTCCCC       2550
ATATGTGAGG GAATTCAGGG TGTCCCCATG GCATCAGCAG TGGGATGAGC       2600
AGCTGTCCGC TCTGACCATG CACTGCTCTG CTCTTTCTTT TCCAGCGGAA       2650
CTAGATGAGA TATCGGGTGA GTCTCCATTC CCAATTGTAT TCTTTCAAAT       2700
GTTCTGCCTT GGGGAGCTGT GGGATAGGAT GTTCTTCTCA CCATGCACTG       2750
```

| | | | | |
|---|---|---|---|---|
| ATTCTACCTT | TCCATTGCAG | GTTTAAGTGC | TGAAAATCTG | AGTAAGTGTC | 2800 |
| CCTCCTGACA | CTGAAGGAAT | TTGGGGTATT | CCCATGGGAT | CAGCCATTGA | 2850 |
| ATGAAAACAT | GGCCCCTCT | CTTCATGCAT | TTCCTATTTC | TTACCTTTGC | 2900 |
| AGAGCAATTA | GCTTCAAAAC | TGAGTGAGTG | CTCACTCCCA | AACTCAAAGT | 2950 |
| AAAGAGAGTC | TGCCTGTGTG | AGCTGTGGGA | TGAGATGTTC | CACTCATCGT | 3000 |
| GCATTGCTTT | TCTCTTTATT | TTCCAGACGA | AAATGCTGAC | GAGTGGGTGA | 3050 |
| GTCTACATTC | ACTAATGCAA | AGAAATATGG | GGTCTCCCAA | GGGATGACAA | 3100 |
| GCGTGTCCCG | CATCATCATT | TGGTGCTTCT | TCTGTCTTTT | TTTTGCAGA | 3150 |
| GGATTGCAAT | TCAGAGCTGA | GTAAGTTGCA | GTCACTGAAC | TGAGGGAATG | 3200 |
| TGGGGTCTTC | CCAAGGGACA | GTGCATGGGA | TGAAAAATCC | CCTCTGACCA | 3250 |
| TGCACTGCTT | TTCTCTTTCT | TTCCCAGAGA | AAGACTGTGA | AGAGATGGGT | 3300 |
| GAGTCCCCCC | CCCCAAAATT | AAACGTTGGG | GTCCTCATGT | GGAGCTGTGG | 3350 |
| ATGAGATGTC | CTCTCATCAC | GCACTGTTTC | TACATTTCTT | TGCAGGTTCT | 3400 |
| GGCGTTGCAG | ATCTGAGTAA | GTCTCCCCTA | CCAGCACGGA | AGGAATTTGT | 3450 |
| GGTCTTCCCA | TGGGATCAGC | CATGGGACTG | ATCATCTGAG | CCCTCTCATC | 3500 |
| ATGCATTTCA | TATTCGTTCC | TTTTGCAGAG | GAACTGGCTG | CAAAATTGGG | 3550 |
| TGAGTGTTGC | CTCCCAAATT | AAATTAAAAA | AGGGGGTCTG | CCTGGGCTCG | 3600 |
| CTGTGGGATA | GGATCTTCCT | CTCACTGTGT | GTTGCTTTTC | CCTTTCTTTT | 3650 |
| CCAGAGGAAT | ATATTGCAGT | GAATCGTGAG | TCTCCCCTCC | GAAATTATAA | 3700 |
| ATGCTGGGGA | AATCTTGTGT | GCGATCGTGG | GTAGAGCTCT | TCCTCTCATC | 3750 |
| ATGCACTGTT | TCTGCTTTTC | CTTTGCAGGG | AGAAGGAATG | TAAAGTTGAG | 3800 |
| TGAGTCTCTC | TTCCCAAACC | AAACAGATTT | GGGGTCTTCC | CATGGGATCA | 3850 |
| GCCATGGGAT | GATAATCTAA | CCCTACTCAT | CATGCATTTC | TTATTGGTTC | 3900 |
| CTTTGGCAGA | TAATATAGCT | GCCAAACTGG | GTGAGTCCCC | CCTCACAGAT | 3950 |
| TACATAAAAA | ATGGGGTCTG | CCTGTGTGAG | CTGTGGGATG | AGATGTTCCT | 4000 |
| CTCATCATGT | ACTACTTTTC | TCTTCCTTTT | CCAGCACAAC | AAACTAAAGA | 4050 |
| ATTGGGTGAG | TCTTCTTTCC | CCAAACAAAG | AAATACGGGA | TTCCCATGGG | 4100 |
| ATGACAAGCT | GTGCCACCTC | ATCATGCCCT | GTTTTTTCTG | TCCTTTTTGC | 4150 |
| AGAGAAACAG | CATTCACAGT | TCCGTAAGTT | GCAGTCACTA | AACTGAAGGA | 4200 |
| ATGTGGGTC | TTCCCAAAGT | CCTGCATACG | GGATGAAAAA | TCCCCTCTGA | 4250 |
| CCATGCACTG | CTTTTCTCTT | TCTATTCCAG | ACAGACACTT | TCAGCGTATG | 4300 |
| GGTGAGTCTC | TCCCCCCCAA | ATTAAAAACG | CTGGGGGCAT | CCTATGGGAG | 4350 |
| CTGTGGGATG | AGATTTTCCT | CTCATCACAC | ACTCCTTCTG | CTTTTCCATT | 4400 |
| GCAGATTTAA | GTGCTGTAAA | CCAGAGTAAG | TCTCCCTCCC | TGCACAGAAG | 4450 |
| GAACTTCCAG | TTTTCCCATG | GGATCAGCCA | TGGGATGATC | ATCCGACTCT | 4500 |
| TCTCATCATA | AATTCGTCTT | CTTCTTTGCA | GAGAAACTGG | TTACAAAACT | 4550 |
| GGGTGAGTCC | AACCTCCCAA | ACTAAATTAA | AAGCAGTCAG | ACTTTGTGAG | 4600 |
| CTGTGGGATG | AGACGTTCTT | CTCATCATGT | GCTGCTTTCC | TTTTACTTTT | 4650 |
| CCAGAGGAAC | ACTTTGAATG | GATGGGTGAG | TCTCCCCTCC | CAAATTAAAA | 4700 |
| ATGTTGGGGT | CTTCCTGTGT | GAGCTGTGGG | ATGAGCTGTT | CCTCCCATCA | 4750 |
| TGCACTGGTT | CTAATTTTCC | TTTGCAGAGA | GAAGGAATGT | AAAGTTGGGT | 4800 |

```
GAGTCTTCTT CCCCAACCAA AGGGATTTGG GGTCTTCCAT GGGATCAGCC        4850
ATGGGATGAT AACCTGAACC TTATCACATA TTTCTTATTT GTTCTTTTTG        4900
CAGAGATACC AGCTGTAATA CTGGGTGAGT CCTCCCTCCC AAATTAAATA        4950
CAAAAGGGGA TCTGCCTGTG TGAGCTGTGG GATGAGATGT TCCTCTCATC        5000
ACGCATTATT TTCTCTTTCT TTTCCAGGGC AACAAGCTAA AGAATCAGGT        5050
GAGTCTTCTT CCCTGTCCCA AAGGACTATG GGTTTCCCAT GGGATGACAA        5100
GCTGTGCCAC CTCCTCACGA GGTGCTTCTT CTTTCTTTTT TGCAGAGAAA        5150
CAGAAATCGG AGCTGAGTAA GTTGCAGTCA CTGAACTGAG GGAATGTGGG        5200
GTCTTCCCAA AGTCTTGTGT ATGGGATGAA AAATCCCCTC TGACCATGCA        5250
CTGCTTTTCT CCTCCTTTGC CAGAGGAGCG CCATGAGGAG ATGGGTGAGT        5300
CTCCCCTCCC ATATTAAAAT CGTTGGGGTC TTCCTGTGTG AGCTGTGAGA        5350
TGAGATGTTC CTCTCATCAT GCGATGCTTT TCTCTCTTTT CCAGCAGAAC        5400
AAACTGAAGC AGTGGGTGAG TCTTTGTCCC CAACCCAAAG GAATATGGGG        5450
CAATCCATGG GATGACAAGC TGTCCCATCT CATCGTGCAT TGCTTTCCTA        5500
TTCCTTTTTT CTAGTGGTAG ATACTGAAGA AGCGGGTGAG TCTTTCCCAA        5550
ACCAAAGCAA TACGGGGTTT CCCATGGCAT GACAAGCTGT CCCACCTCAG        5600
CATCCGTTGT TTTTCTCTTT CTTTTCCAGA AAAACCATCT GAAGAATTGG        5650
ATTGAGAGAT GAACTGCGCC TCACAGTAAC CACAGGAGTT AAGCTTCATA        5700
GATCAATGAC TGCACAGCAT ACAAAAACCA CGATACCTCA AACAGAGCAA        5750
GGAAATCCAC AGCGAGAACA AGAGGAGCCA GTGTTTGTGT TGAGTGAGAA        5800
CACTGCAGTT CTGTCAGCCA AAGCTGCCTG AGGGACCGCC AAACTGAGGG        5850
TGTGCGACCT CCAACTCAAA GCCAATTGGA AGAAAGAAAC CATAGAAAGG        5900
AAGGAAGGG GAGGAAGACA GAGATCCTGG AAGAGATATG GGCATTTGGG         5950
GAAATAGTGT GACCATGTAT CAGGCTGTGT GGACATCTAA CGAATATGTC        6000
ATGTTTTTGT AAATACAAGC ATGCACTCAG AAACAAAGGT AGAAAACTGC        6050
TTTGGGTGGT AACACTGTTC TCTGTCAAAA TATAATAAAG AATACCTGCT        6100
GATGGTAATG GATCATTGAT TGTGAGCAGT TATTGGGGTT TGGTTCCATG        6150
AAACAGGCTG AGTCTTCTTC CCAGAAACAA AGCAACGTGG GCTCTATCGG        6200
ATAACAAGCC GACCCTTCTC ACCATGCACT GCTATTCCAG CACAACAAGG        6250
CTCTCTCCAG GAAGCTAAAA AGGGATAAAA TAAATTAATA GGAAAGAAAT        6300
ACACAAAAAC AAGAAAATTT AAAAAGAAT ACTCCAAAAA ATCTATAATT         6350
ATTACAATAA AAACTTTAAA AAAACACACC AACCTTCCAC CCTGGGGGAG        6400
CACCAATGAC AGCCTTTTGT GCCCCATCGC GGTTTTATGA GAACAGCCAC        6450
ACACTTCAGA GCTGACCCCG TGAGCCCCAC AGTGGGGGGA CCTCCCACAG        6500
TGGGTGGACC TCCTCCACAA CCACCCCCAT CACTCACATT GAATGCCCAA        6550
AGAAACAACA GCCCCAAAGG TTCCTCCTGG TGCTTCAGCC GCGTGTGTTC        6600
CTCATTCTGC TGTGCTGATG GTGATCATTA ACCCAACAGC TCATTAACCA        6650
GGTTATGGCT CAGGTGCGTG CTGCTGAACA AGCTTGGAGC CTAAAATGGT        6700
TCCTGCACAC ATCCCAGGGG ACGGCCCTCC ACCTTTCACT CCCCGCCATT        6750
ACAGCTCTCC TTAATCAGAG GAATACAGAT TCCATGCACT GAGTGCACTG        6800
AGCCATCGCC CACCTTCCCT ACAAACACCT CCTGGTCCCC ACAAACCCTC        6850
```

-continued

| | | | | | |
|---|---|---|---|---|---|
| ACTGTGGGAA | GAGGGGCTCT | GGGGGGGTCA | CAGGGACAAA | CATTTAATAA | 6900 |
| TTCCTGTATT | AATGGTTGAT | TAACTTAAAA | ATCTGTACTG | ATCAAATAAA | 6950 |
| CTGCCACCCC | TTGGGCATAG | CTCAGAGCAT | GCTCATGGAG | TACAGCCCAC | 7000 |
| AGCTTTCCTC | TGTGCTAGGG | CAATGCTTCT | CCTGGGTCCA | TGTTCATCCT | 7050 |
| GGGTGGATGC | AGAGCCCAG | GGTGGTACAT | GAAACTGCAA | TGGGATGTCA | 7100 |
| GTGTTCAGAG | TTCTCCAACC | GTCTGCCCCA | TTGCCAAAGG | GGTAAAGTTC | 7150 |
| CTCGGAGCAG | ATTACCACAC | CCTGGAGCTG | GGCAAAGGTT | GACGCTGGGC | 7200 |
| AAAGGTAGAA | GCTGGGCATA | GCTGCACGTT | TCCTGCAGCT | CAGGTGAGGG | 7250 |
| ATTTCTGTCT | CTGTGGGGCT | CCTTGTAGGG | GAAATCCTTG | GGGGGTCATC | 7300 |
| TGCTCTGCCT | CACAGCCTGT | GAGGAGCACT | GGCACTGCCC | AAGGCAGTGG | 7350 |

I claim:

1. An isolated, natural or non-natural nucleic acid having the sequence of FIG. 17 (SEQ ID NO. 9).

2. An isolated, natural or non-natural nucleic acid having the sequence of FIG. 25 (SEQ ID NO. 14).

3. The probe gi6.

4. A process for determining whether the haplotype of a chicken is of the B-G subregion of the chicken major histocompatibility complex which comprises:
    (i) providing a DNA sample from said chicken;
    (ii) cleaving said DNA sample with the restriction enzyme Pvu II to provide cleavage reaction products;
    (iii) subjecting said cleavage reaction products to electrophoresis on a gel;
    (iv) thereafter subjecting said cleavage reaction products on said gel to hybridizing conditions with the probe gi6 to provide a pattern of hybridized cleavage reaction products on said gel;
    (v) preparing an autoradiogram of said pattern; and
    (vi) comparing said pattern on said autoradiogram with the pattern known to result from electrophoresis of the Pvu II cleavage reaction products of a known allele of the B-G subregion of the chicken major histocompatibility complex;.
wherein correspondence, as determined by said comparing, between said pattern on said autoradiogram and said pattern known to result from the hybridization of the same probe with said cleavage reaction products produced from a sequence from the B-G subregion of the chicken MHC of said fowl by Pvu II is indicative that the haplotype of said chicken is of the B-G subregion of the chicken major histocompatibility complex.

5. A DNA probe for use in a hybridization reaction to detect a restriction fragment in restriction enzyme digested genomic DNA of a chicken or turkey or a pheasant, which restriction fragment may have a polymorphic portion of the coding region of the B-G subregion of the major histocompatibility complex of said chicken, turkey or pheasant, said probe having a nucleic acid sequence complementary to said coding region of the B-G subregion of the major histocompatibility complex of said chicken, turkey or pheasant, said nucleic acid sequence of said probe being any of FIGS. 6 (SEQ ID NO. 1), 7 (SEQ ID NO. 2), 11 (SEQ ID NO. 3), 12 (SEQ ID NO. 4), 13 (SEQ ID NO. 5), 14 (SEQ ID NO. 6), 15 (SEQ ID NO. 7), 16 (SEQ ID NO. 8), 17 (SEQ ID NO. 9), 18 (SEQ ID NO. 10), 19 (SEQ ID NO. 11), or 25 (SEQ ID NO. 14).

6. A DNA probe as defined by claim 5 wherein said restriction fragment may have a polymorphic portion of the coding region of the B-G subregion of the major histocompatibility complex of a chicken.

7. An isolated, non-naturally occurring nucleic acid having the sequence of FIG. 6 (SEQ ID NO. 1), FIG. 7 (SEQ ID NO. 2), FIG. 11 (SEQ ID NO. 3), FIG. 12 (SEQ ID NO. 4), FIG. 13 (SEQ ID NO. 5), FIG. 14 (SEQ ID NO. 6), FIG. 15 (SEQ ID NO. 7), FIG. 16 (SEQ ID NO. 8), FIG. 18 (SEQ ID NO. 10) or FIG. 19 (SEQ ID NO. 11).

8. A process for determining whether the haplotype of a chicken is of the B-G subregion of the major histocompatibility complex of said chicken which comprises:
    (i) providing a sample of DNA from a chicken;
    (ii) cleaving said sample of DNA with a restriction enzyme to provide cleavage reaction products, said restriction enzyme being Pvu II, Bam HI, EcoRI, Hind III or Pst I;
    (iii) providing a probe, said probe being an isolated and purified nucleic acid having the sequence of any of the FIGS. 6 (SEQ ID NO. 1), 7 (SEQ ID NO. 2), 11 (SEQ ID NO. 3), 12 (SEQ ID NO. 4), 13 (SEQ ID NO. 5), 14 (SEQ ID NO. 6), 15 (SEQ ID NO. 7), 16 (SEQ ID NO. 8), 17 (SEQ ID NO. 9), 18 (SEQ ID NO. 10), or 25 (SEQ ID NO. 14);
    (iv) determining whether said probe hybridizes with any of said cleavage reaction products;
wherein the occurrence of such hybridization indicates that the haplotype of said chicken is of said B-G subregion of the chicken major histocompatibility complex.

* * * * *

UNITED STATES PATENT AND TRADEMARK OFFICE
CERTIFICATE OF CORRECTION

PATENT NO. : 5,451,670
DATED : September 19, 1995
INVENTOR(S) : MARCIA M. MILLER It is certified that error appears in the above-identified patent and that said Letters Patent is hereby corrected as shown below:

Column 1, line 5 insert the following:

This invention was made with government support in the form of Grant No. ROI-AI 21736 from the National Institutes of Health and Grant No. DCB 860932 from the National Science Foundation. The government may have certain rights in the invention.--

Signed and Sealed this

Twenty-eighth Day of April, 1998

Attest:

BRUCE LEHMAN

Attesting Officer

Commissioner of Patents and Trademarks